(12) United States Patent
Spada et al.

(10) Patent No.: US 8,455,656 B2
(45) Date of Patent: *Jun. 4, 2013

(54) KINASE INHIBITORS

(75) Inventors: Lon T. Spada, Walnut, CA (US); Jane Guo Shiah, Irvine, CA (US); Patrick Hughes, Aliso Viejo, CA (US); Thomas C. Malone, Irvine, CA (US); Gerald W. Devries, San Clemente, CA (US); Jeffrey L. Edelman, Irvine, CA (US); Julie A. Wurster, Irvine, CA (US); Xialing Guo, San Clemente, CA (US); Sougato Boral, Santa Ana, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/380,493

(22) Filed: Feb. 26, 2009

(65) Prior Publication Data

US 2009/0286773 A1 Nov. 19, 2009
US 2012/0238558 A9 Sep. 20, 2012

Related U.S. Application Data

(63) Continuation-in-part of application No. 10/837,361, filed on Apr. 30, 2004, now Pat. No. 7,771,742.

(51) Int. Cl.
*A61K 31/40* (2006.01)
*A61F 9/007* (2006.01)
*C07D 213/00* (2006.01)

(52) U.S. Cl.
USPC ............................... 546/339; 514/414; 604/8

(58) Field of Classification Search
USPC ........................................ 546/201; 514/320
See application file for complete search history.

(56) References Cited

U.S. PATENT DOCUMENTS

| | | |
|---|---|---|
| 3,845,770 A | 11/1974 | Theeuwes et al. |
| 3,916,899 A | 11/1975 | Theeuwes et al. |
| 4,052,505 A | 10/1977 | Higuchi |
| 4,057,619 A | 11/1977 | Higuchi et al. |
| 4,063,064 A | 12/1977 | Saunders et al. |
| 4,088,864 A | 5/1978 | Theeuwes et al. |
| 4,144,317 A | 3/1979 | Higuchi |
| 4,158,005 A | 6/1979 | Bodor et al. |
| 4,186,184 A | 1/1980 | Zaffaroni |
| 4,190,642 A | 2/1980 | Gale et al. |
| 4,281,654 A | 8/1981 | Shell et al. |
| 4,285,987 A | 8/1981 | Ayer et al. |
| 4,396,625 A | 8/1983 | Yamamori et al. |
| 4,425,346 A | 1/1984 | Horlington et al. |
| 4,474,451 A | 10/1984 | Mizokami et al. |
| 4,478,818 A | 10/1984 | Shell et al. |
| 4,494,274 A | 1/1985 | Thurlow |
| 4,599,353 A | 7/1986 | Bito |
| 4,649,151 A | 3/1987 | Dougherty et al. |
| 4,656,186 A | 4/1987 | Bommer et al. |
| 4,668,506 A | 5/1987 | Bawa |
| 4,675,338 A | 6/1987 | Bommer et al. |
| 4,693,885 A | 9/1987 | Bommer et al. |
| 4,712,500 A | 12/1987 | Montandon et al. |
| 4,863,457 A | 9/1989 | Lee |
| 4,866,168 A | 9/1989 | Dougherty et al. |
| 4,932,934 A | 6/1990 | Dougherty et al. |
| 4,935,498 A | 6/1990 | Sessler et al. |
| 4,959,217 A | 9/1990 | Sanders et al. |
| 4,968,715 A | 11/1990 | Dougherty et al. |
| 4,981,871 A | 1/1991 | Abelson |
| 5,002,962 A | 3/1991 | Pandey et al. |
| 5,017,579 A | 5/1991 | Gubin et al. |
| 5,019,400 A | 5/1991 | Gombotz et al. |
| 5,028,621 A | 7/1991 | Dougherty et al. |
| 5,034,413 A | 7/1991 | Chan et al. |
| 5,075,115 A | 12/1991 | Brine |
| 5,089,509 A | 2/1992 | Chandraratna |
| 5,093,349 A | 3/1992 | Pandey et al. |
| 5,100,431 A | 3/1992 | Buster et al. |
| 5,169,638 A | 12/1992 | Dennis et al. |
| 5,171,741 A | 12/1992 | Dougherty |
| 5,173,504 A | 12/1992 | Dougherty |
| 5,190,966 A | 3/1993 | Dougherty et al. |
| 5,198,460 A | 3/1993 | Pandey et al. |
| 5,268,178 A | 12/1993 | Calhoun et al. |

(Continued)

FOREIGN PATENT DOCUMENTS

| | | |
|---|---|---|
| EP | 0364417 | 4/1990 |
| WO | 97-34920 | 9/1997 |

(Continued)

OTHER PUBLICATIONS

Hillery et. al., Drug Delivery and Targetting for Pharmacists and Pharmaceutical Scientists, 2001, published by Taylor & Francis, pp. 64-67, 84-96, 99-101.*

Hcaplus 2006:1403, "Preparation of (3Z)-3-(2,3-dihydro-1H-inden-1-ylidene)-1,3-dihydro-2H-indol-2-ones as tyrosine kinase inhibitors", Andrews et. al.*

Plowman et al, "Receptor Tyrosine Kinases as Targets for Drug Intervention",1994, DN&P 7(6): 334-339.

Bolen, "Nonreceptor tyrosine protein kinases", 1993, Oncogen 8: 2025-2031.

(Continued)

*Primary Examiner* — D M Seaman
*Assistant Examiner* — Heidi Reese
(74) *Attorney, Agent, or Firm* — Laura L. Wine; Joel B. German; Debra D. Condino

(57) ABSTRACT

The present invention relates to drug delivery systems comprising ocular implant, which include organic molecules, capable of modulating tyrosine kinase signal transduction in order to regulate, modulate and/or inhibit abnormal cell proliferation, in combination with a polymer, which polymer serves to control, modify, modulate and/or slow the release of the therapeutic component into the environment of the eye in which said composite is placed.

2 Claims, 6 Drawing Sheets

U.S. PATENT DOCUMENTS

| | | | |
|---|---|---|---|
| 5,300,114 A | 4/1994 | Gwon et al. | |
| 5,314,905 A | 5/1994 | Pandey et al. | |
| 5,356,629 A | 10/1994 | Sander et al. | |
| 5,378,475 A | 1/1995 | Smith et al. | |
| 5,385,887 A | 1/1995 | Yim et al. | |
| 5,438,071 A | 8/1995 | Clauss et al. | |
| 5,459,159 A | 10/1995 | Pandey et al. | |
| 5,466,233 A | 11/1995 | Weiner et al. | |
| 5,504,074 A | 4/1996 | D'Amato et al. | |
| 5,587,371 A | 12/1996 | Sessier et al. | |
| 5,587,479 A | 12/1996 | Makovec et al. | |
| 5,597,897 A | 1/1997 | Ron et al. | |
| 5,655,832 A | 8/1997 | Pelka et al. | |
| 5,656,297 A | 8/1997 | Berstein et al. | |
| 5,688,819 A | 11/1997 | Woodward et al. | |
| 5,707,643 A | 1/1998 | Ogura | |
| 5,770,589 A | 6/1998 | Billson et al. | |
| 5,776,699 A | 7/1998 | Klein et al. | |
| 5,792,783 A | 8/1998 | Tang et al. | |
| 5,798,349 A | 8/1998 | Levy et al. | |
| 5,824,074 A | 10/1998 | Koch et al. | |
| 5,834,504 A | 11/1998 | Tang et al. | |
| 5,877,207 A | 3/1999 | Klein et al. | |
| 5,882,682 A | 3/1999 | Rork et al. | |
| 5,883,113 A | 3/1999 | Tang et al. | |
| 5,883,116 A | 3/1999 | Tang et al. | |
| 5,886,020 A | 3/1999 | Tang et al. | |
| 5,906,920 A | 5/1999 | Evans et al. | |
| 5,913,884 A | 6/1999 | Trauner et al. | |
| 5,919,970 A | 7/1999 | Song et al. | |
| 5,922,773 A | 7/1999 | Lipton et al. | |
| 5,958,954 A | 9/1999 | Klein et al. | |
| 6,051,576 A | 4/2000 | Ashton et al. | |
| 6,066,675 A | 5/2000 | Wen et al. | |
| 6,217,869 B1 | 4/2001 | Meyer et al. | |
| 6,217,895 B1 | 4/2001 | Guo et al. | |
| 6,225,303 B1 | 5/2001 | Miller et al. | |
| 6,258,319 B1 | 7/2001 | Hearst et al. | |
| 6,270,492 B1 | 8/2001 | Sinofsky | |
| 6,270,749 B1 | 8/2001 | Blumenkranz et al. | |
| 6,274,614 B1 | 8/2001 | Richter et al. | |
| 6,290,713 B1 | 9/2001 | Russell | |
| 6,306,426 B1 | 10/2001 | Olejnik et al. | |
| 6,317,616 B1 | 11/2001 | Glossop | |
| 6,319,273 B1 | 11/2001 | Chen et al. | |
| 6,331,313 B1 | 12/2001 | Wong et al. | |
| 6,357,568 B1 | 3/2002 | Chen | |
| 6,403,649 B1 | 6/2002 | Woodward et al. | |
| 6,455,062 B1 | 9/2002 | Olejnik | |
| 6,482,854 B1 | 11/2002 | Lipton et al. | |
| 6,537,568 B2 | 3/2003 | Olejnik et al. | |
| 6,541,504 B1 * | 4/2003 | Andrews et al. | 514/414 |
| 6,548,078 B2 | 4/2003 | Guo et al. | |
| 6,559,173 B1 | 5/2003 | Andrews et al. | |
| 6,565,871 B2 | 5/2003 | Roser et al. | |
| 6,573,280 B2 | 6/2003 | Dreyer | |
| 6,595,945 B2 | 7/2003 | Brown | |
| 6,699,863 B1 | 3/2004 | Andrews et al. | |
| 6,726,918 B1 | 4/2004 | Wong | |
| 6,747,025 B1 | 6/2004 | Andrews et al. | |
| 6,765,012 B2 | 7/2004 | Andrews et al. | |
| 7,005,444 B2 | 2/2006 | Andrews et al. | |
| 7,015,220 B2 | 3/2006 | Andrews et al. | |
| 7,060,844 B2 * | 6/2006 | Andrews et al. | 548/464 |
| 7,771,742 B2 * | 8/2010 | Hughes et al. | 424/428 |
| 7,915,443 B2 | 3/2011 | Wurster et al. | |
| 2002/0040015 A1 | 4/2002 | Miller et al. | |
| 2002/0094998 A1 | 7/2002 | Burke et al. | |
| 2003/0119812 A1 | 6/2003 | Brazzell et al. | |
| 2003/0199478 A1 | 10/2003 | Andrews et al. | |
| 2003/0225152 A1 | 12/2003 | Andrews et al. | |
| 2004/0019098 A1 | 1/2004 | Andrews et al. | |
| 2004/0054374 A1 | 3/2004 | Weber | |
| 2005/0244470 A1 | 11/2005 | Hughes et al. | |
| 2005/0244475 A1 | 11/2005 | Edelman et al. | |
| 2005/0244477 A1 | 11/2005 | Hughes et al. | |
| 2006/0004084 A1 | 1/2006 | Andrews et al. | |
| 2007/0066541 A1 | 3/2007 | Hughes et al. | |
| 2008/0241252 A1 | 10/2008 | Lyons et al. | |
| 2009/0286773 A1 | 11/2009 | Spada et al. | |

FOREIGN PATENT DOCUMENTS

| | | |
|---|---|---|
| WO | 02-085248 | 10/2002 |
| WO | 03-084951 A1 | 10/2003 |
| WO | WO 03084951 * | 10/2003 |
| WO | WO2004-112748 | 12/2004 |
| WO | 2005-107706 A2 | 11/2005 |
| WO | 2005-107708 A1 | 11/2005 |
| WO | WO 2005-107706 | 11/2005 |
| WO | WO 2005-107708 | 11/2005 |
| WO | 2008-121665 | 10/2008 |
| WO | 2010-099368 | 9/2010 |

OTHER PUBLICATIONS

Antcliff R., et al Marshall J., The Pathogenesis of Edema in Diabetic Maculopathy, Semin Ophthalmol 1999; 14:223-232.

Allergan, Inc., 2004, TazoracAllergan Product Information, Product Information Sheet, 0, 1-8.

Andrews et al, 2006, Preparation of (3Z)-3-(2,3-dihydro-1H-inden-1-ylidene)-1,3-dihydro-2H-indol-2-ones as tyrosine kinsase inhibitors, 14038, 0, 0.

Anya M. Hillery et al., 2001, Drug Delivery and Targeting for Pharmacists and Pharmaceutical Scientists, ., ., 30 Pages.

Baker, 1987, Controlled Release of Biologically Active Agent, A Wiley-Interscience Publication, 0, 73-75.

Bito, Jan. 1, 1987, Prostaglandins Old Concepts and New Perspectives, Archives of Opthalmology, 105, 1036-1039.

Bito, L. Z., Jan. 1, 1984, Applied Pharmacology in the Medical Treatment of Glaucomas Drance, Glaucoma: Applied Pharmacology, 20, pp. 477-505, S. M. & Neufeld, A. H. eds., New York, Grune & Stratton.

Bito, L. Z., Jan. 1, 1985, Biological Protection with Prostanoids, CRC Press, Inc., 1, pp. 231-252, Cohen, M. M., ed., Boca Raton, Fla., CRC Press Inc.

Bodor et al, 1992, A Comparison of Intraocular Pressure Elevating Activity of Loteprednoletabonate and Dexamethasone in Rabbits, Current Eye Research, 11, 525-530.

Brubaker, 2001, Mechanism of Action of Bimatoprost (LumiganTM), Surv Ophthalmol, 45-Suppl 4, S347-S351.

Busse et al, 2001, Tyrosine Kinase Inhibitors: Rationale, Mechanisms of Action, and Implications for Drug Resistance, Semin Oncol, 28-Suppl 16, 47-55.

Charles et al, Apr. 1991, Use of Bioerodible Polymers Impregnated with Mitomycin in Glaucoma Filtration Surgery in Rabbits, Ophthalmology, 98-4, 503-508.

Chen et al, Jun. 12, 2002, LumiganR: A Novel Drug for Glaucoma Therapy, Optom in Pract., 3, 95-102.

Cheng-Kuo Cheng, et al., 1995, Intravitreal Sustained-Release Dexamethasone Device in the Treatment of Experimental Uveites, Investigative Ophthalmology & Visual Science, 96 (2), 442-453.

Chiang et al, 1996, Pharmacokinetics and Intraocular Pressure Lowering Effect of Timolol Preparations in Rabbit Eyes, Journal of Ocular Pharmacology and Therapeutics, 12-4, 471-480.

Clive, 2002, A New Ocular Hypotensive Agent for Achieving Target Intraocular Pressure, ACTA Ophthalmol Scand Scientific Abstracts, 80-4, 457.

Coleman et al, 2003, A 3-Month Randomized Controlled Trial of Bimatoprost (LUMIGAN) Versus Combined Timolol and Dorzolamide (Cosopt) in Patients with Glaucoma or Ocular Hypertension, Ophthalmology, 110-12, 2362-8.

Di Colo, 1992, Controlled Drug Release From Implantable Matrices Based on Hydrophobic Polymers, Biomaterials, 13-12, 850-856.

Drugs of the Future, 2003, Tazarotene, Drugs of the Future, 2, 208-209.

Enyedi et al, 1995, An Intravitreal Device Providing Sustained Release of Cyclosporins and Dexamethason, Current Eye Research, 0, 549-557.

Epstein, 1986, Primary Open-Angle Glaucoma, Chandler and Grant's Glaucoma, 0, 129-181.

Fabbro et al, 2002, Protein Tyrosine Kinase Inhibitors: New Treatment Modalities?, Current Opinion in Pharmacology, 2, 374-381.

Fotsis et al, 1994, The Endogenous Oestrogen Metabolite 2-methoxyoestradiol inhibits Angiogeneses and Suppresses Tumour Growth, Current Opinion in Pharmacology, 237, 368.

Gilman et al, 1990, The Pharamceutical Basis of Therapeutics, Goodman and Gilman's, 8th Edition, 1447-1451.

Goel et al, 2002, Tyrosine Kinase Inhibitors: A Clinical Perspective, Current Oncology Reports, 4, 9-19.

Guenther, 2003, Optimizing Treatment with Topical Tazarotene, Am. J. Clin. Dermotol, 4-3, 197-202.

Hainsworth et al, 1996, Sustained Release Intravitreal Dexamethasone, Journal of Ocular Pharmacology and Therapeutics, 12-1, 57-63.

Haluska et al, 2001, Receptor tyrosine kinase inhibitors, Current Opinion in Investigational Drugs, 2-2, 280-286.

Hare et al, 2001, Efficacy and Safety of Memantine, an NMDA-Type Open-Channel Blocker, from Reduction of Retinal Injury associated with Experimental Glaucoma in Rat and Monkey, Sur Ophthalmol, 45-Suppl. 3, S284-S289.

Hashizoe et al, 1994, Scleral Plugof Biodegradable Polymers for Controlled Drug Release in the Vitreous, Arch Ophthalmol, 112, 1380-1384.

Heller, 1987, Hydrogels in Medicine and Pharmacy, N.A. Peppes ed., III, 137-149.

Hubbard et al, 2000, Protein Tyrosine Kinase Structure and Function, Annu. Rev. Biochem., 69, 373-98.

Jackanicz et al, 1973, Polyactic Acid as a Biodegradable Carrier for Contraceptive Steroids, Contraception, 8-3, 227-235.

Jampel et al, Mar. 1990, Glaucoma Filtration Surgery in Monkeys Using 5-Fluorouridine in Polyanhydride Disks, Arch Ophthalmol, 108, 430-435.

Jorge Heller, 1987, Biodegradable Polymers in Controlled Drug Delivery, Critical Reviews in Therapeutic Drug Carrier Systems, 1 (1), 39-90.

Kochinke et al, 1994, A New Vitreal Drug Delivery System Using an Implantable Biodegradable Polymeric Device, Invest Ophthalmol Vis Sci, 35, 2815-2819.

Kwak et al, 1992, Evaluation of the Retinal Toxicity and Pharmacokinetics of Dexamethasone After Intravitreal Injection, Arch. Ophthalmol, 110, 259-66.

Lai et al, 2002, Alpha-2 Adrenoceptor Agonist Protects Retinal Function After Acute Retinal Ischemic Injury in the Rat, Vis Neurosci, 19, 175-185.

Lee et al, Dec. 1987, Glaucoma Filtration Surgery in Rabbits Using Bioerodible Polymers and 5-Fluorouacil, Ophthalmol, 94-12, 1523-1530.

Lee et al, Nov. 1988, The Use of Bioerodible Polymers and 5-Fluorouracils in Glaucoma Filtration Surgery, Ophthalmology & Visual Science, 29-11, 1692-1697.

Marks, 2001, Topical Tazarotene:Review and Re-Evaluation, Retinoids, 17(3), 72-74.

Maurice, 1983, Micropharmaceutics of the Eye, Ocular Inflammation Ther., 1, 97-102.

Miller et al, 1977, Degradation Rats of Oral Resorbable Implants (Polyactates and Polyglycolates): Rate Modification with Changes in PLA/PGA Copolymer Ratios, J. Biomed Materials Res, 11, 711-719.

Miller et al, 1997, Synthesis and Structure-Activity Profiles of A-Homoestranes, the Estratopones, J. Med. Chem., 40, 3836-3841.

Oculex, Aug. 6, 2002, Oculex Announces Positive Clinical Results for Posurdex(r) the first biodegradable ocular implant, PR Newswire, ., 1-2.

Olsen et al, 1995, Human Scleral Permeability: Effects of Age, Cryotherapy, Transcleral Diode Laser, and Surgical Thinning, Invest. Ophthalmol. Vis. Sci., 36, 1893-1903.

Philip E.J. Hoyng, 2000, Pharmacological Therapy for Glaucoma, Drugs 2000, 59 (3), 411-434,.

Phillips et al, Nov. 2002, Efficacy of 0.1% Tazarotene Cream for the treatment of Photodamage, Arch Dermatol, 138(11), 1486-1493.

Phillips et al, 1985, Penetration of Timolol Eye Drops into Human Aqueous Humor: The First Hour, British Journal of Ophthalmology, 69, 217-218.

Pribluda et al, 2000, 2-Methoxyestradiol: An Endogenous Antiangionic and Antiproliferative Drug Candidate, Cancer and Metastasis Reviews, 19, 173-179.

Quigley et al, 1980, The Mechanism of Optic Nerve Damage in Experimental Acute Intraocular Pressure Elevation, Invest. Ophthalmol. Vis. Sci., 19, 505-517.

Allergan, Alphagan Product Information, Product Sheet, 2005, 1-10, 0.

Anderson et al, An Injectable Sustained Release Fertility Control System, Contraception, 1976, 375-384, 13.

Database Registry, XP-002336813, May 19, 1989, RN-120685-11-2, 2 pages.

Laird et al, Small molecule tyrosine kinase inhibitors: clinical development of anticancer agents, Expert Opinion on Investigational Drugs, Jan. 2003, 51-64, 12-1.

Merkli et al, "Use of Insoluble Biodegradable Polymers in Ophthalmic Systems for the Sustained Release of Drugs*", Eur. J. Pharm. Biopharm., 41(5), 271-281, (1985).

* cited by examiner

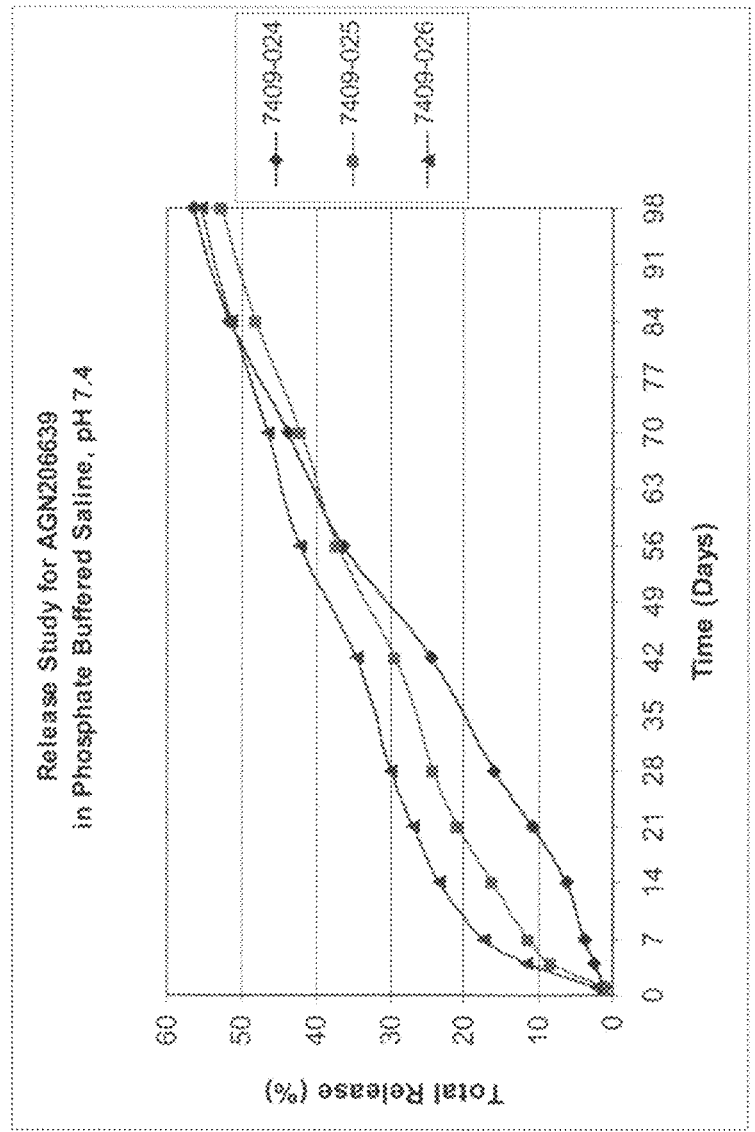
Figure 1: Release rate plot for AGN206639 in phosphate buffered saline release medium, pH 7.4

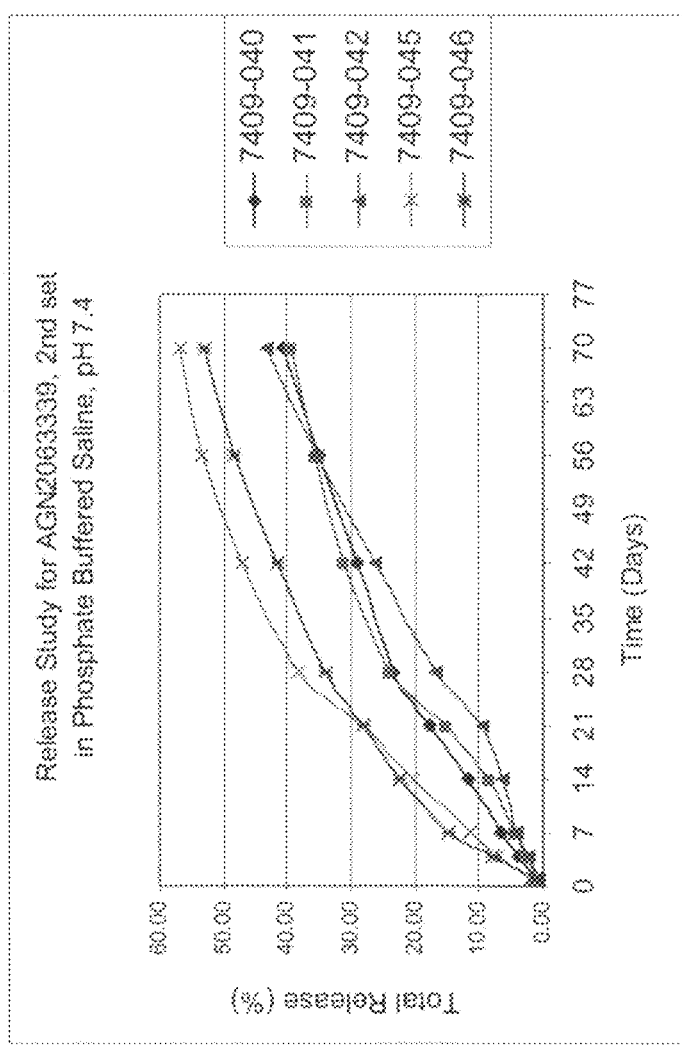
Figure 2. Release rate plot for AGN206639 reformulated series in phosphate buffered saline release medium, pH 7.4.

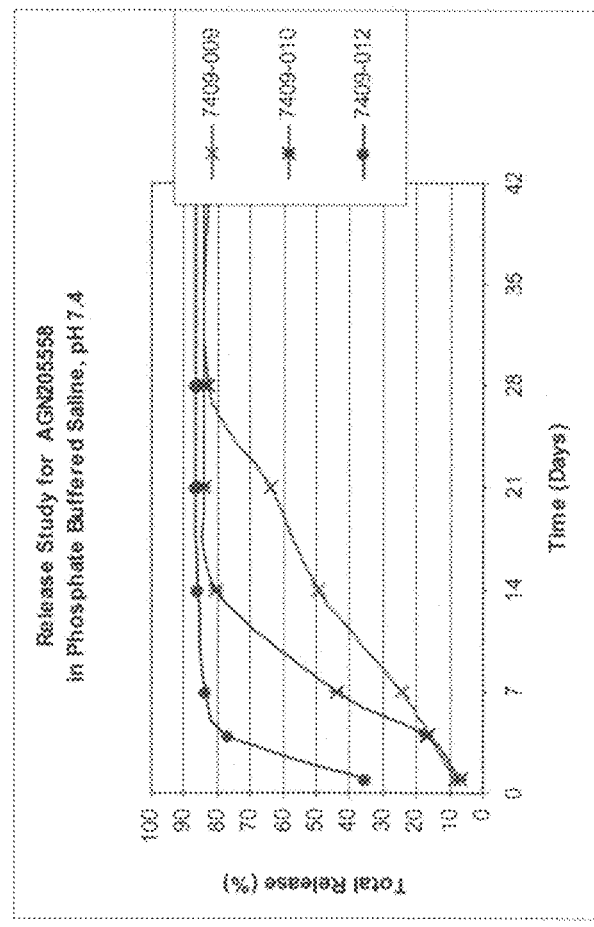
Figure 3: Release rate plot for AGN205558 in phosphate buffered saline release medium, pH 7.4.

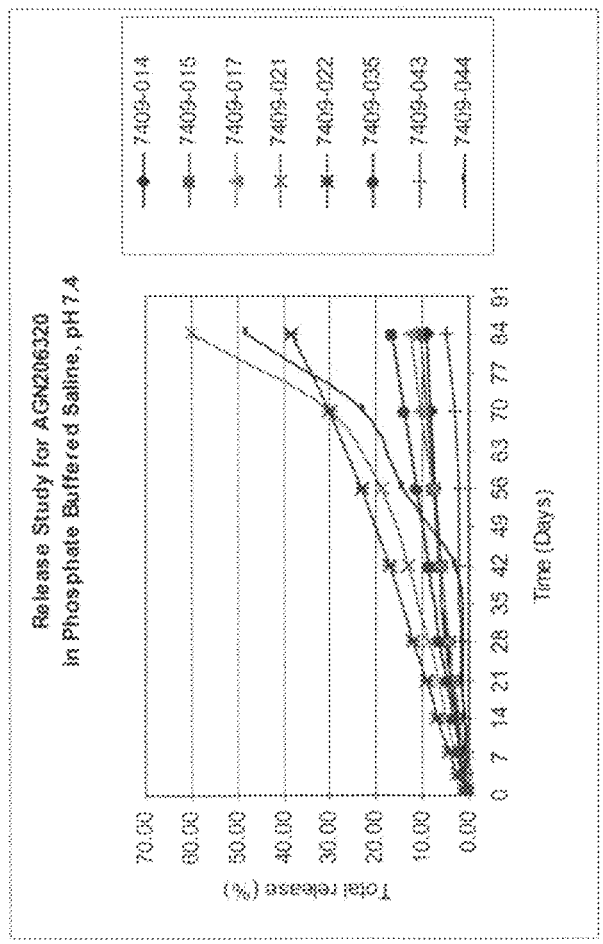
Figure 4. Release rate plot for AGN206320 in phosphate buffered saline release medium, pH 7.4.

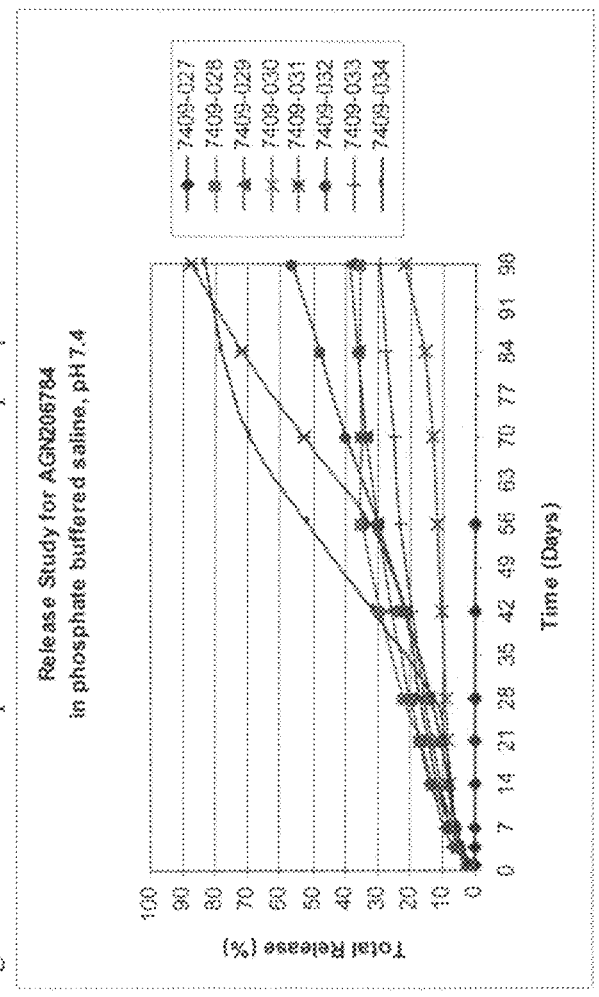
Figure 5: Release rate plot for AGN206784 in phosphate buffered saline release medium, pH 7.4.

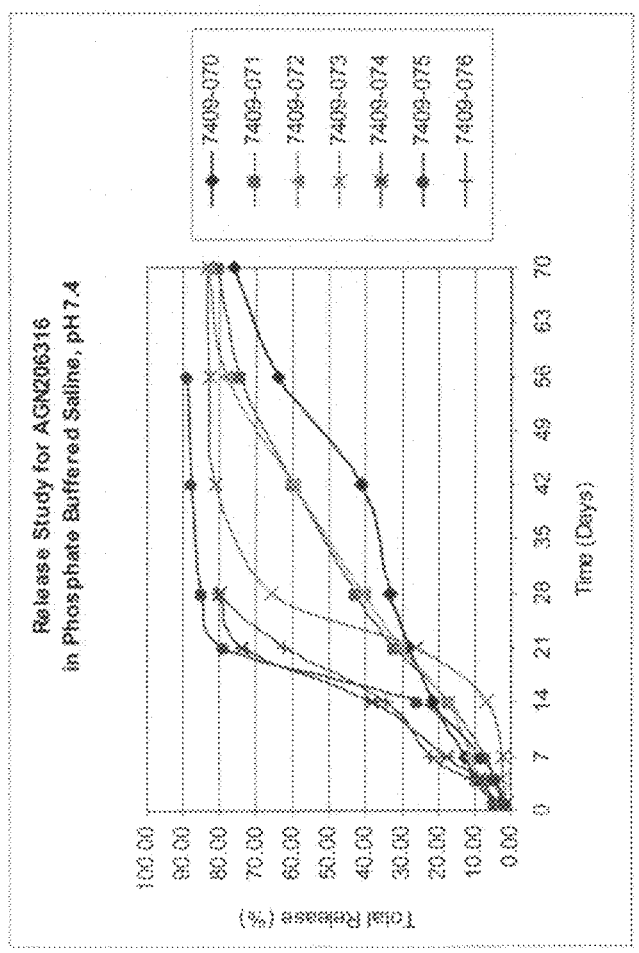
Figure 6. Release rate plot for AGN206316 in phosphate buffered saline release medium, pH 7.4.

KINASE INHIBITORS

CROSS-REFERENCE TO RELATED APPLICATIONS

This application is a continuation in part of application Ser. No. 10/837,361, filed on April 30, 2004 now U.S. Pat. No. 7,771,742.

BACKGROUND OF THE INVENTION

1. Field of the Invention

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders.

2. Description of the Related Art

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The RTKs comprise a large family of transmembrane receptors with diverse biological activities. The intrinsic function of RTKs is activated upon ligand binding, which results in phosphorylation of the receptor and multiple cellular substrates, and subsequently in a variety of cellular responses.

At present, at least nineteen (19) distinct RTK subfamilies have been identified. One RTK subfamily, designated the HER subfamily, is believed to be comprised of EGFR, HER2, HER3 and HER4. Ligands to the HER subfamily of receptors include epithelial growth factor (EGF), TGF-α, amphiregulin, HB-EGF, betacellulin and heregulin.

A second family of RTKs, designated the insulin subfamily, is comprised of the INS-R, the IGF-1R and the IR-R. A third family, the "PDGF" subfamily includes the PDGF α and β receptors, CSFIR, c-kit and FLK-II. Another subfamily of RTKs, identified as the FLK family, is believed to be comprised of the Kinase insert Domain-Receptor fetal liver kinase-1 (KDR/FLK-1), the fetal liver kinase 4 (FLK-4) and the fms-like tyrosine kinase 1 (flt-1). Each of these receptors was initially believed to be receptors for hematopoietic growth factors. Two other subfamilies of RTKs have been designated as the FGF receptor family (FGFR1, FGFR2, FGFR3 and FGFR4) and the Met subfamily (c-met and Ron).

Because of the similarities between the PDGF and FLK subfamilies, the two subfamilies are often considered together. The known RTK subfamilies are identified in Plowman et al, 1994, DN&P 7(6): 334-339, which is incorporated herein by reference.

The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and includes Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, Oncogene 8: 2025-2031, which is incorporated herein by reference.

Many of the tyrosine kinases, whether an RTK or non-receptor tyrosine kinase, have been found to be involved in cellular signaling pathways leading to cellular signal cascades leading to pathogenic conditions, including cancer, psoriasis and hyper immune response.

In view of the surmised importance of PTKs to the control, regulation and modulation of cell proliferation the diseases and disorders associated with abnormal cell proliferation, many attempts have been made to identify receptor and non-receptor tyrosine kinase "inhibitors" using a variety of approaches, including the use of mutant ligands soluble receptors and antibodies RNA ligands and tyrosine kinase inhibitors.

More recently, attempts have been made to identify small molecules which act as tyrosine kinase inhibitors. For example, bis monocyclic, bicyclic or heterocyclic aryl compounds, vinylene-azaindole derivatives and 1-cyclopropyl-4-pyridyl-quinolones have been described generally as tyrosine kinase inhibitors. Styryl compounds, styryl-substituted pyridyl compounds certain quinazoline derivatives seleoindoles and selenides, tricyclic polyhydroxylic compounds and benzylphosphonic acid compounds have been described as compounds for use as tyrosine kinase inhibitors for use in the treatment of cancer.

The identification of effective small compounds which specifically inhibit signal transduction by modulating the activity of receptor and non-receptor tyrosine kinases to regulate and modulate abnormal or inappropriate cell proliferation is therefore desirable and one object of this invention.

Finally, certain small compounds are disclosed in U.S. Pat. Nos. 5,792,783; 5,834,504; 5,883,113; 5,883,116 and 5,886,020 as useful for the treatment of diseases related to unregulated TKS transduction. See also, U.S. Pat. Nos. 6,541,504; 6,559,173; 6,765,012; 6,747,025; 6,699,863; 7,005,444; 7,015,220 and 7,060,844. These patents are hereby incorporated by reference in its entirety for the purpose of disclosing starting materials and methods for the preparation thereof, screens and assays to determine a claimed compound's ability to modulate, regulate and/or inhibit cell proliferation, indications which are treatable with said compounds, formulations and routes of administration, effective dosages, etc.

DESCRIPTION OF THE DRAWING FIGURES

FIG. 1 shows the release rate plot for 3-[5-(3-Diethylamino-propyl)-3,3-dimethyl-3H-isobenzofuran-1-ylidene]-5-fluoro-1,3-dihydro-indol-2-one from a polymeric matrix into phosphate buffered saline release medium.

FIG. 2 shows the release rate plot for a reformulation of 3-[5-(3-Diethylamino-propyl)-3,3-dimethyl-3H-isobenzofuran-1-ylidene]-5-fluoro-1,3-dihydro-indol-2-one from a polymeric matrix into phosphate buffered saline release medium.

FIG. 3 shows the release rate plot for 3-[5-(3-Diethylamino-propyl)-3-methyl-3H-isobenzofuran-1-ylidene]-5-fluoro-1,3-dihydro-indol-2-one from a polymeric matrix into phosphate buffered saline release medium.

FIG. 4 shows the release rate plot for 1-(2-Oxo-1,2-dihydro-indol-3-ylidene)-1,3-dihydro-isobenzofuran-5-carboxylic acid (2-diethylamino-ethyl)-amide from a polymeric matrix into phosphate buffered saline release medium.

FIG. 5 shows the release rate plot for 5-Fluoro-3-{5-[2-(4-hydroxy-piperidin-1-yl)-ethyl]-3,3-dimethyl-3H-isobenzofuran-1-ylidene}-1,3-dihydro-indol-2-one from a polymeric matrix into phosphate buffered saline release medium.

FIG. 6 shows the release rate plot for 3-[1-(5-Fluoro-2-oxo-1,2-dihydro-indol-3-ylidene)-1,3-dihydro-isobenzofuran-5-yl]-propionic acid into from a polymeric matrix phosphate buffered saline release medium.

BRIEF SUMMARY OF THE INVENTION

The present invention relates to composites of organic molecules capable of modulating, regulating and/or inhibiting tyrosine kinase signal transduction and a polymer, e.g. a bioerodible polymer. Such composites are useful for the treatment of diseases related to unregulated TKS transduction, including cell proliferative diseases such as cancer, restenosis, conditions associated with metabolic diseases such as diabetes, inflammatory diseases vascular proliferative disorders such as diabetic retinopathy, age-related macular degeneration and retinopathy of prematurity, autoimmune diseases and transplant rejection. The TKI compounds utilized in the composites, i.e. the ocular implants, of this invention are selected from the compounds represented by formula I, below

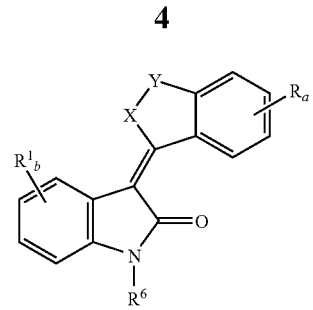

wherein X is O;

Y is $[C(R^2)_2]_c$;

$R^1$ is selected from the group consisting of halogen, aryl, $C_1$ to $C_8$ alkyl, $CF_3$, $OCF_3$, $OCF_2H$, $S(O)_fR^2$, $(CR^3R^4)_dC(O)OR^2$, $O(CR^3R^4)_eC(O)OR^2$, $NR^2(CR^3R^4)_dC(O)R^2$, $NR^2(CR^3R^4)_dC(O)OR^2$, $OP(O)(OR^2)_2$, $OC(O)OR^2$, $OCH_2O$, $NR^2(CH_2)_eN(R^2)_2$, $O(CH_2)_eN(R^2)_2$, $(CR^3R^4)_dCN$, $O(CR^3R^4)_eCN$, $(CR^3R^4)_dAr$, $NR^2(CR^3R^4)_dAr$, $O(CR^3R^4)_dAr$, $S(O)_f CR^3R^4)_dAr$, $(CR^3R^4)_dSO_2R^2$, $(CR^3R^4)_dC(O)N(R^2)_2$, $NR^2(CR^3R^4)_dC(O)N(R^2)_2$, $O(CR^3R^4)_dC(O)N(R^2)_2$, $S(O)_fCR^3R^4)_eC(O)N(R^2)_2$, $(CR^3R^4)_dOR^2$, $NR^2(CR^3, R^4)_eOR^2$, $O(CR^3, R^4)_eOR^2$, $S(O)_fCR^3, R^4)_eOR^2$, $C(O)(CR^3R^4)_dR^3$ $NR^2C(O)(CR^3R^4)_d R^3$, $OC(O)(CR^3R^4)_dN(R^2)_2$, $C(O)(CR^3R^4)_dN(R^2)_2$, $NR^2C(O)(CR^3R^4)_dN(R^2)_2$, $OC(O)(CR^3R^4)_dN(R^2)_2$, $(CR^3R^4)_d R^3$, $NR^2(CR^3R^4)_dR^3$, $O(CR^3R^4)_dR^3$, $S(O)_fCR^3R^4)_dR^3$, $(CR^3R^4)_dN(R^2)_2$, $NR^2(CR^3R^4)_eN(R^2)_2$, $O(CR^3R^4)_eN(R^2)_2$, $S(O)f (CR^3R^4)_dN(R^2)_2$, $N(R^5)_2$, $OR^5$, $C(O)R^5$, $S(O)_fR^5$;

$R^2$ is selected from the group consisting of hydrogen, $C_1$ to $C_8$ alkyl, $C_1$ to $C_8$ alkenyl, $C_1$ to $C_8$ alkynyl, $C_1$ to $C_4$ alkylol, lower alkylphenyl, phenyl, $(CR^3R^4)_dAr$, $(CR^3R^4)_dC(O)OR^2$, $(CR^3R^4)_dSO_2R^2$, $(CR^3, R^4)_dOR^2$ $(CR^3, R^4)_dOSO_2R$, $(CR^3R^4)_dP(O)(OR^2)_2$, $(CR^3R^4)_dR^2$, $(CR^3R^4)_eN(R^2)_2$, $(CR^3R^4)_eNR^2C(O)N(R^2)_2$;

$N(R^2)_2$ may form a 3-7 membered heterocyclic ring, for example, pyrrolidine, 3-fluoropyrrolidine, piperidine, 4-fluoropiperidine, N-methylpiperazine, morpholine, 2,6-dimethylmorpholine, thiomorpholine. Said heterocyclic ring may be substituted with one or more of $R^3$;

$[C(R^2)_2]_c$ may form a 3-7 membered carbocyclic or heterocyclic ring;

R is selected from the group consisting of halogen, $C_1$ to $C_8$ alkyl, $CF_3$, $OCF_3$, $OCF_2H$, $(CR^3R^4)_dCN$, $NR^2(CR^3R^4)_e$ $CN$, $O(CR^3R^4)_eCN$, $S(O)_fR^2$, $(CR^3R^4)_dC(O)OR^2$, $NR^2(CR^3R^4)_dC(O)OR^2$, $O(CR^3R^4)_dC(O)OR^2$, $S(O)_fCR^3R^4)_d C(O)OR^2$, $(CR^3R^4)_dAr$, $NR^2(CR^3R^4)_dAr$, $O(CR^3R^4)_dAr$, $S(O)_fCR^3R^4)_dAr$, $(CR^3R^4)_dSO_2R^2$, $NR^2(CR^3R^4)_dS(O)_f R^2$, $O(CR^3R^4)d S(O)_fR^2$, $S(O)_fCR^4R^4)_eS(O)_fR^2$, $(CR^3R^4)_d C(O)N(R^2)_2$, $NR^2(CR^3R^4)_dC(O)N(R^2)_2$, $O(CR^3R^4)_dC(O)N(R^2)_2$, $S(O)_fCR^3R^4)_eC(O)N(R^2)_2$, $(C R^4)_dOR^2$, $NR^2(CR^3R^4)_eOR^2$, $O(CR^3, R^4)_eOR^2$, $S(O)C R^4)_dOR^2$, $(C^3R^4)_d OSO_2R^2$, $NR(CR^3R^4)_eOSO_2R^2$, $O(CR^3, R^4)_eOSO_2R^2$, $S(O)CR^3R^4)_eOSO_2R^2(CR^3, R^4)_dP(O)(OR^2)_2$, $NR^2 (CR^3, R^4)_dP(O)(OR^2)_2$, $O(CR^3, R^4)_dP(O)(OR^2)_2$, $S(O)_f (CR^3R^4)_eP(O)(OR^2)_2$, $C(O)(CR^3R^4)_dR^3$, $NR^2C(O)(CR^3R^4)_dR^3$, $HNC(O)R^2$, $HN-C(O)OR^2$, $(CR^3R^4)_dN(R^2)_2$, $NR^2(CR^3R^4)_eN(R^2)_2$, $O(CR^3R^4)_eN(R^2)_2$, $S(O)_f (CR^3R^4)_dN(R^2)_2$, $OP(O)(OR^2)_2$, $OC(O)OR^2$, $OCH_2O$, $HN-CH=CH$, $-N(COR^2)CH_2CH_2$, $HC=N-NH$, $N=CH-S$, $(CR^3R^4)_dC=C(CR^3R^4)_dR^2$, $(CR^3R^4)_dC=C(CR^3R^4)_dOR$ $(CR^3R^4)_dC=C(CR^3R^4)_dN(R^2)_2$, $(CR^3R^4)_d CC(CR^3R^4)_dR^2$, $(C^3R^4)_dCC(CR^3R^4)_eOR^2$, $(CR^3R^4)_dCC (CR^3R^4)_eN(R^2)_2$, $(CR^3R^4)_dC(O)(CR^3R^4)_dR^2$, $(CR^3R^4)_dC(O)(CR^3R^4)_dOR^2$, $(CR^3R^4)_dC(O)(CR^3R^4)_dN(R^2)_2$, $R^3$ and $R^4$ may be selected from the group consisting of H, F, hydroxy, and $C_1$-$C_4$ alkyl or $CR^3R^4$ may represent a carbocyclic or heterocyclic ring of from 3 to 6 carbons, alternatively $(CR^3R^4)d$ and $(CR^3R^4)e$ may form a 3-7 membered carbocyclic or heterocyclic ring, preferably $R^3$ and $R^4$ are H, F, $CH_3$ or hydroxy;

$R^5$ is Ar—$R^1{}_b$;

$R^6$ is selected from hydrogen, $C_1$-$C_8$ alkyl, hydroxylmethyl and phenyl;

b is 0 or an integer of from 1 to 2;

a is 0 or an integer of from 1 to 3;

c is an integer of from 1 to 2;

d is 0 or an integer of from 1 to 5;

e is an integer of from 1 to 4;

f is 0 or an integer of from 1 to 2, and further provided said alkyl or aryl radicals may be substituted with one or two halo, hydroxy, lower alkyloxy, lower alkyl amino or cycloalkylamino radicals wherein the cycloalkyl ring can include an enchained oxygen, sulfur or additional nitrogen atom and may be substituted with one or two halo or lower alkyl radicals;

and pharmaceutically acceptable salts thereof.

DETAILED DESCRIPTION OF THE INVENTION

Compounds of the general formula I, above, are useful as kinase inhibitors in the composites of this invention. As such, said composites will be useful for treating ocular diseases, i.e. diseases of the eye, related to unregulated tyrosine kinase signal transduction.

Broadly speaking, the eye includes the eyeball and the tissues and fluids which constitute the eyeball, the periocular muscles (such as the oblique and rectus muscles) and the portion of the optic nerve which is within or adjacent to the eyeball. An anterior ocular condition is a disease, ailment or condition which affects or which involves an anterior (i.e. front of the eye) ocular region or site, such as a periocular muscle, an eyelid or an eyeball tissue or fluid which is located anterior to the posterior wall of the lens capsule or ciliary muscles. Thus, an anterior ocular condition primarily affects or involves, the conjunctiva, the cornea, the conjunctiva, the anterior chamber, the iris, the posterior chamber (anterior to the retina but posterior to the posterior wall of the lens capsule), the lens or the lens capsule and blood vessels and nerve which vascularize or innervate an anterior ocular region or site.

A condition of the posterior segment (posterior ocular condition) of the eye is a disease, ailment or condition which significantly affects or involves a tissue or cell type in a posterior ocular region or site (that is, in a position posterior to a plane through the posterior wall of the lens capsule), such as the accordingly located parts of the choroid or sclera, vitreous, vitreous chamber, retina, optic nerve (i.e. the optic disc), and blood vessels and nerves which vascularize or innervate a posterior ocular (or posterior segment) region or site.

Thus, a posterior ocular condition can include a disease, ailment or condition, such as for example, macular degeneration (such as non-exudative age-related macular degeneration and exudative age-related macular degeneration); choroidal neovascularization; acute macular neuroretinopathy; macular edema (such as cystoid macular edema and diabetic macular edema); Behcet's disease, retinal disorders, diabetic retinopathy (including proliferative diabetic retinopathy); retinal arterial occlusive disease; central retinal vein occlusion; uveitis (including intermediate and anterior uveitis); retinal detachment; ocular trauma which affects a posterior ocular site or location; a posterior ocular condition caused by or influenced by an ocular laser treatment; posterior ocular conditions caused by or influenced by a photodynamic therapy; photocoagulation; radiation retinopathy; epiretinal membrane disorders; branch retinal vein occlusion; anterior ischemic optic neuropathy; non-retinopathy diabetic retinal dysfunction, retinitis pigmentosa and glaucoma. Glaucoma can be considered a posterior ocular condition because a therapeutic goal can be to prevent the loss of or reduce the occurrence of loss of vision due to damage to or loss of retinal cells or optic nerve cells (i.e. neuroprotection). The infiltrative growth of new blood vessels can disrupt or destroy nervous tissue; thus the inhibition of angiogenesis can also be considered to provide protection to affected neurons.

Macular edema is a major cause of visual loss in patients, and can accompany a number of pathological conditions, including, without limitation, diabetes, central retinal vein occlusion (CRVO) and branch retinal vein occlusion (BRVO). Although laser photocoagulation can reduce further vision loss in patients with diabetic macular edema (DME), vision that has already been decreased by macular edema through neural cell death usually does not improve appreciably by use of laser photocoagulation. Currently, there is no FDA (U.S. Food and Drug Administration) approved treatment for macular edema associated with CRVO. For macular edema associated with BRVO, grid laser photocoagulation may be an effective treatment for some patients.

Diabetic macular edema is characterized abnormal leakage of macromolecules, such as lipoproteins, from retinal capillaries into the extravascular space followed by an oncotic influx of water into the extravascular space. The leakage may be caused by or exacerbated by the growth of new blood vessels (angiogenesis). Abnormalities in the retinal pigment epithelium (RPE) may also cause or contribute to diabetic macular edema. These abnormalities can allow increased fluid from the choriocapillaris to enter the retina or they may decrease the normal efflux of fluid from the retina to the choriocapillaris. The breakdown of the blood-retina barrier at the level of the retinal capillaries and the retinal pigment epithelium may also be accompanied or caused by changes to tight junction proteins. Antcliff R., et al Marshall J., *The Pathogenesis Of Edema In Diabetic Maculopathy*, Semin Opthalmol 1999; 14:223-232.

Macular edema from venous occlusive disease can result from thrombus formation at the lamina cribrosa or at an arteriovenous crossing. These changes can result in an increase in retinal capillary permeability and accompanying retinal edema. The increase in retinal capillary permeability and subsequent retinal edema can ensue from of a breakdown of the blood retina barrier mediated in part by vascular endothelial growth factor (VEGF), a 45 kD glycoprotein. It is known that VEGF can increase vascular permeability; possibly by increasing phosphorylation of tight junction proteins such as occludin and zonula occluden. Similarly, in human non-ocular disease states such as ascites, VEGF has been characterized as a potent vascular permeability factor (VPF).

Ocular conditions which can be treated or addressed in accordance with the present invention include, without limitation, the following:

Maculopathies/retinal degeneration: macular degeneration, including age related macular degeneration (ARMD), such as non-exudative age related macular degeneration and exudative age related macular degeneration, choroidal neovascularization, retinopathy, including diabetic retinopathy, acute and chronic macular neuroretinopathy, central serous chorioretinopathy, and macular edema, including cystoid macular edema, and diabetic macular edema. Uveitis/ retinitis/choroiditis: acute multifocal placoid pigment epitheliopathy, Behcet's disease, birdshot retinochoroidopathy, infectious (syphilis, lyme, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpiginous choroiditis, subretinal fibrosis, uveitis syndrome, and Vogt-Koyanagi-Harada syndrome. Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, Eales disease. Traumatic/surgical: sympathetic ophthalmia, uveitic retinal disease, retinal detachment, trauma, laser, PDT, photocoagulation, hypoperfusion during surgery, radiation retinopathy, bone marrow transplant retinopathy. Proliferative disorders: proliferative vitreal retinopathy and epiretinal membranes, proliferative diabetic retinopathy. Infectious disorders: ocular histoplasmosis, ocular toxocariasis, presumed ocular histoplasmosis syndrome (POHS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis. Genetic disorders: retinitis pigmentosa, systemic disorders with associated retinal dystrophies, congenital stationary night blindness, cone dystrophies, Stargardt's disease and fundus flavimaculatus, Bests disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum. Retinal tears/holes: retinal detachment, macular hole, giant retinal tear. Tumors: retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors. Miscellaneous: punctate inner choroidopathy, acute posterior multifocal placoid pigment epitheliopathy, myopic retinal degeneration, acute retinal pigment epithelitis and the like.

Regarding the TKI compounds utilized in the composites of this invention:

In one embodiment, $R^1$ is selected from the group consisting of H, i.e. b is 0; $CH_3$, F and Cl; preferably $R^1$ is H, F or Cl.

Preferably, a is 0 or R is selected from the group consisting of $NHCOR^7$ and $N(R^7)_2$ wherein $R^7$ is selected from the group consisting of hydrogen, $C_1$ to $C_4$ alkyl and phenyl, wherein said alkyl or phenyl may be substituted with hydroxy, methylol or amino substituents and more preferably $R^7$ is selected from the group consisting of hydrogen, methyl, ethyl, hydroxypropyl, and aminomethylol phenyl.

Preferably $R^6$ is H.

Preferably c is 1.

In another preferred embodiment, $R^1$ is selected from the group consisting of H, i.e. b is 0, F and Cl.

Preferably, a is 1 and R is selected from the group consisting of $(CR^3R^4)_dN(R^2)_2$, $NR^2(CR^3R^4)_dN(R^2)_2$, $O(CR^3R^4)_dN(R^2)_2$, $(CR^3R^4)_dCC(CR^3R^4)_dN(R^2)_2$, $NR^2C(O)(CR^3R^4)_dN(R^2)_2$.

Preferably $R^6$ is H.

Preferably c is 1.

In particular, the compounds of the present invention are selected from the compounds of Tables 1 through 11 and the Examples, below.

TABLE 1

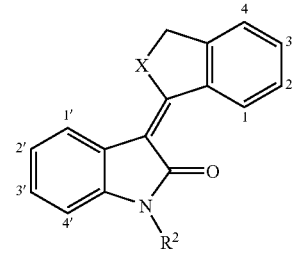

| Example Number | $R^2$ | 1 | 2 | 3 | 4 | 1' | 2' | 3' | 4' | X |
|---|---|---|---|---|---|---|---|---|---|---|
| Example 1 | H | H | H | H | H | H | H | H | H | O |
| Example 2 | H | H | H | H | H | H | Cl | H | H | O |
| Example 3 | H | H | H | H | H | $CH_3$ | H | H | H | O |
| Example 4 | H | H | H | H | H | H | F | H | H | O |
| Example 5 | H | H | $NH_2$ | H | H | H | H | H | H | O |
| Example 6 | H | H | $NHCOCH_3$ | H | H | H | H | H | H | O |
| Example 7 | H | H | $NHCOCH_2CH_2CH_3$ | H | H | H | H | H | H | O |
| Example 8 | H | H | NHCO-cyclopropyl | H | H | H | H | H | H | O |
| Example 9 | H | H | $NHCOCH_2CH_2Cl$ | H | H | H | H | H | H | O |
| Example 10 | H | H | $NHCOCH_2Ph$-4-$OCH_3$ | H | H | H | H | H | H | O |
| Example 11 | H | H | $NHCH_2CH_3$ | H | H | H | H | H | H | O |
| Example 12 | H | H | H | $NH_2$ | H | H | H | H | H | O |
| Example 13 | H | H | $NHCOPh$-3-$NH_2$,6-$CH_2OH$ | H | H | H | H | H | H | O |
| Example 14 | H | H | $NHCH_2CH_2CH_2OH$ | H | H | H | H | H | H | O |

TABLE 1-continued

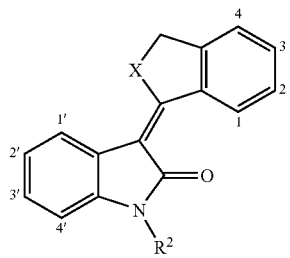

| Example Number | R² | 1 | 2 | 3 | 4 | 1' | 2' | 3' | 4' | X |
|---|---|---|---|---|---|---|---|---|---|---|
| Example 15 | H | H | H | NHCH₂CH₃ | H | H | H | H | H | O |
| Example 16 | H | H | NH₂ | H | H | H | Cl | H | H | O |
| Example 17 | H | H | H | NH₂ | H | H | Cl | H | H | O |
| Example 18 | H | H | H | NHCOCH₃ | H | H | H | H | H | O |
| Example 19 | H | H | H | NHCOCH₃ | H | H | Cl | H | H | O |
| Example 20 | H | H | NHCOCH₃ | H | H | H | Cl | H | H | O |
| Example 21 | H | H | N(CH₃)₂ | H | H | H | H | H | H | O |
| Example 22 | H | H | NHCH₃ | H | H | H | H | H | H | O |
| Example 23 | H | H | H | N(CH₃)₂ | H | H | H | H | H | O |
| Example 24 | H | H | H | NHCH₃ | H | H | H | H | H | O |
| Example 26 | H | H | NHCOCH₂CH₂CH₂Cl | H | H | H | H | H | H | O |
| Example 27 | H | H | N(CH₂CH₃)₂ | H | H | H | H | H | H | O |

In the present invention there is provided a drug delivery system comprising a therapeutic component, comprising one or more of the above compounds, in combination with a polymer to form a composite of said therapeutic component and said polymer, said composite being configured and suitable for insertion into the eye of a patient suffering from an ocular disease or condition, wherein said polymer serves to control, modify, modulate and/or slow the release of the therapeutic component into the environment of the eye in which said composite is placed.

Intraocular Implant

In a first aspect of the ocular composite of this invention there is provided an intraocular implant in accordance with the disclosure herein which comprises a therapeutic component, i.e. a tyrosine kinase inhibitor, and a drug release sustaining polymer component associated with the therapeutic component. The implants may be solid, semisolid, or viscoelastic. In accordance with the present invention, the therapeutic component comprises, consists essentially of, or consists of, a tyrosine kinase inhibitor (TKI), for example, an agent or compound that inhibits or reduces the activity of tyrosine kinase. The TKI may also be understood to be a small molecule TKI. The drug release sustaining component is associated with the therapeutic component to sustain release of an amount of the TKI into an eye in which the implant is placed. TKIs may be released from the implant by diffusion, erosion, dissolution or osmosis. The drug release sustaining component may comprise one or more biodegradable polymers or one or more non-biodegradable polymers. Examples of biodegradable polymers of the present implants may include poly-lactide-co-glycolide (PLGA and PLA), polyesters, poly (ortho ester), poly(phosphazine), poly(phosphate ester), polycaprolactone, natural polymers such as gelatin or collagen, or polymeric blends. The amount of the TKI is released into the eye for a period of time greater than about one week after the implant is placed in the eye and is effective in reducing or treating an ocular condition.

In one embodiment, the intraocular implants comprise a TKI and a biodegradable polymer matrix. The TKI is associated with a biodegradable polymer matrix that degrades at a rate effective to sustain release of an amount of the TKI from the implant effective to treat an ocular condition. The intraocular implant is biodegradable or bioerodible and provides a sustained release of the TKI in an eye for extended periods of time, such as for more than one week, for example for about one month or more and up to about six months or more. The implants may be configured to provide release of the therapeutic agent in substantially one direction, or the implants may provide release of the therapeutic agent from all surfaces of the implant.

The biodegradable polymer matrix of the foregoing implants may be a mixture of biodegradable polymers or the matrix may comprise a single type of biodegradable polymer. For example, the matrix may comprise a polymer selected from the group consisting of polylactides, poly(lactide-co-glycolides), polycaprolactones, and combinations thereof.

In another embodiment, intraocular implants comprise a therapeutic component that comprises a TKI, and a polymeric outer layer covering the therapeutic component. The polymeric outer layer includes one or more orifices or openings or holes that are effective to allow a liquid to pass into the implant, and to allow the TKI to pass out of the implant. The therapeutic component is provided in a core or interior portion of the implant, and the polymeric outer layer covers or coats the core. The polymeric outer layer may include one or more non-biodegradable portions. The implant can provide an extended release of the TKI for more than about two months, and for more than about one year, and even for more than about five or about ten years. One example of such a polymeric outer layer covering is disclosed in U.S. Pat. No. 6,331,313.

Advantageously, the present implants provide a sustained or controlled delivery of therapeutic agents at a maintained level despite the rapid elimination of the TKIs from the eye. For example, the present implants are capable of delivering therapeutic amounts of a TKI for a period of at least about 30 days to about a year despite the short intraocular half-lives associated with TKIs. Plasma TKI levels obtained after implantation are extremely low, thereby reducing issues or risks of systemic toxicity. The controlled delivery of the TKIs from the present implants permits the TKIs to be administered into an eye with reduced toxicity or deterioration of the blood-aqueous and blood-retinal barriers, which may be associated with intraocular injection of liquid formulations containing TKIs.

A method of making the present implants involves combining or mixing the TKI with a biodegradable polymer or polymers. The mixture may then be extruded or compressed to form a single composition. The single composition may then be processed to form individual implants suitable for placement in an eye of a patient. Another method of making the present implants involves providing a polymeric coating around a core portion containing a TKI, wherein the polymeric coating has one or more holes.

The implants may be placed in an ocular region to treat a variety of ocular conditions, such as treating, preventing, or reducing at least one symptom associated with non-exudative age related macular degeneration, exudative age related macular degeneration, choroidal neovascularization, acute macular neuroretinopathy, cystoid macular edema, diabetic macular edema, Behcet's disease, diabetic retinopathy, retinal arterial occlusive disease, central retinal vein occlusion, uveitic retinal disease, retinal detachment, trauma, conditions caused by laser treatment, conditions caused by photodynamic therapy, photocoagulation, radiation retinopathy, epiretinal membranes, proliferative diabetic retinopathy, branch retinal vein occlusion, anterior ischemic optic neuropathy, non-retinopathy diabetic retinal dysfunction, retinitis pigmentosa, ocular tumors, ocular neoplasms, and the like.

Kits in accordance with the present invention may comprise one or more of the present implants, and instructions for using the implants. For example, the instructions may explain how to administer the implants to a patient, and types of conditions that may be treated with the implants.

Intravitreal Implant

In a second aspect of the present invention, there is provided a biodegradable intravitreal implant comprising: a plurality of biodegradable polymer microspheres encapsulating a tyrosine kinase inhibitor (TKI), the microspheres releasing the TKI at a rate effective to sustain release of the TKI from the microspheres for at least about one week after the implant is placed in the vitreous of an eye. By encapsulating it is meant that the active agent is associated with, dispersed within, mixed with and/or embedded in the polymer.

The microspheres of this biodegradable intravitreal implant can release the TKI at a rate effective to sustain release of an amount of the TKI from the implant for more than one month from the time the implant is placed in the vitreous of the eye. The TKI can be present in the implant (i.e. the plurality of microspheres) in an amount of from about 5% by weight to about 70% by weight, preferably from about 40% by weight to about 60% by weight of the implant, and the biodegradable polymer matrix can comprise a poly(lactide-co-glycolide) in an amount from about 30% by weight to about 95% by weight, preferably from about 40% by weight to about 60% by weight of the implant.

A process for making biodegradable active agent microspheres includes the following steps:
(a) preparing an organic phase, which comprises, an active agent, a biodegradable polymer, and a solvent for the active agent and the polymer;
(b) preparing a first aqueous phase; containing at least one emulsifier, e.g. the emulsifier can be polyvinyl alcohol (PVA), polysorbate, poloxamer, etc.;
(c) combining the organic and the aqueous phase to form an emulsion;
(d) preparing a second aqueous phase;
(e) adding the second aqueous phase to the emulsion to form a solution;
(f) stirring the solution, and;
(g) evaporating the solvent, thereby making biodegradable active agent microspheres.

The organic phase can be a viscous fluid. This method can also have the step of crystallizing active agent in the organic phase and/or the further step of crystallizing active agent in the emulsion.

Preferably, the pH of the first aqueous phase is between about pH 6 and about pH 8 and the pH of the second aqueous phase is between about pH 4 and about pH 9.

A detailed process for making biodegradable active agent microspheres can have the steps of:
(a) preparing a viscous organic phase, which comprises, a TKI, a biodegradable PLGA (or PLA) polymer, and a solvent for the active agent and the PLGA (or PLA) polymer;
(b) crystallizing active agent in the viscous organic phase;
(c) preparing a first aqueous phase with a pH between about pH 6 and about pH 8;
(d) combining the organic and the aqueous phase to form an emulsion;
(e) crystallizing active agent in the emulsion;
(f) preparing a second aqueous phase with a pH between about pH 4 and about pH 9;
(g) adding the second aqueous phase to the emulsion to form a suspension;
(h) stirring the suspension, and;
(i) evaporating the solvent, thereby making biodegradable active agent microspheres. The active agent can be a TKI.

The presently disclosed invention also encompasses a method for treating an ocular condition of an eye of a patient by placing biodegradable intraocular microspheres into the vitreous of an eye of the patient, the microspheres comprising a TKI and a biodegradable polymer, wherein the microspheres degrades at a rate effective to sustain release of an amount of the TKI from the microspheres effective to treat the ocular condition. The ocular condition can be, for example, a retinal ocular, glaucoma or a proliferative vitreoretinopathy.

In an alternative embodiment a biodegradable intravitreal implant comprising a tyrosine kinase inhibitor (TKI) and a biodegradable polymer can be prepared by a method comprising the step of: extruding a mixture of a TKI and a biodegradable polymer to form a biodegradable implant that degrades at a rate effective to sustain release of an amount of the TKI from the implant for at least about one week after the implant is placed in the vitreous of an eye. The mixture can consist essentially of the TKI and the biodegradable polymer. The polymer can be a polylactide, poly(lactide-co-glycolide), polycaprolactone, or a derivative thereof, or a mixture thereof. The polymer can release the TKI at a rate effective to sustain release of an amount of the TKI from the implant for more than one month from the time the implant is placed in the vitreous of the eye. The TKI can be provided in an amount from about 5% by weight to about 70% by weight, preferably from about 30% by weight to about 70% by weight of the implant, and the biodegradable polymer matrix can comprise a poly(lactide-co-glycolide) in an amount from about 30% by weight to about 95% by weight, preferably from about 30% by weight to about 70% by weight of the implant. More preferably, the TKI can be provided in an amount from about 40% by weight to about 60% by weight of the implant, and the biodegradable polymer matrix can comprise a poly(lactide-co-glycolide) in an amount from about 40% by weight to about 60% by weight of the implant.

The microspheres of the present invention may range in size from 1-100 um and may include additives, e.g. cholesterol, PEG, etc, to modify the release rate of the TKI from the microsphere or reduce inflammation etc.

The TKI can be present in the microspheres in various forms, e.g. in a dispersed molecular form, or as crystalline aggregates.

The microspheres of the present invention can be administered by injection, i.e. as a suspension in an appropriate vehicle, e.g. a viscous vehicle, such as a hyaluronic acid gel, containing up to 30% by weight of the microspheres, by means of a 22G-30G needle, preferably to form a depot comprising said microspheres.

Finally, the polymer may be selected to have a degradation rate, whereby the microparticles partially or completely disappear before next injection.

The most preferred TKIs for utilization in the ocular implants of this invention, wherein the Example Nos. refer to the Example Nos. of the compounds disclosed and claimed in U.S. patent application Ser. Nos. 10/405,577 and 11/180,496, which are hereby incorporated by reference, are:

EXAMPLE 474

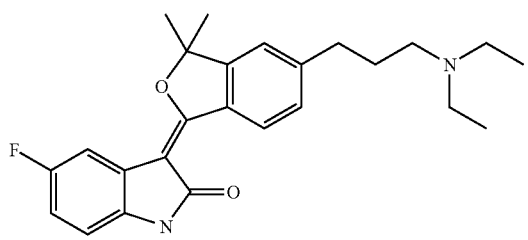

3-[5-(3-Diethylamino-propyl)-3,3-dimethyl-3H-isobenzofuran-1-ylidene]-5-fluoro-1,3-dihydro-indol-2-one

EXAMPLE 481

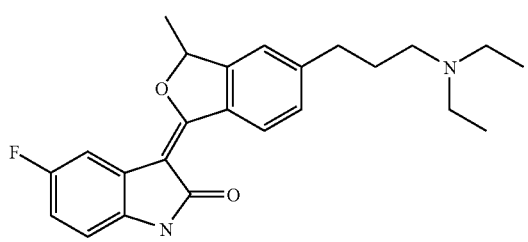 [SMILES: CCN(CC)CCCc1ccc2c(c1)C(C)(C)O/C2=C1/C(=O)Nc2ccc(F)cc21]

3-[5-(3-Diethylamino-propyl)-3-methyl-3H-isobenzofuran-1-ylidene]-5-fluoro-1,3-dihydro-indol-2-one

EXAMPLE 508

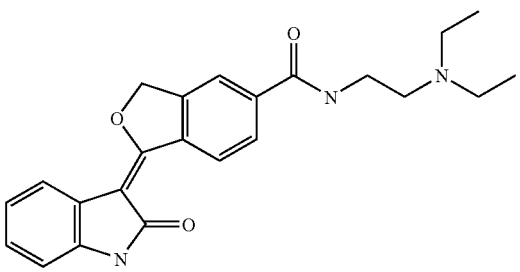 [SMILES: CCN(CC)CCNC(=O)c1ccc2c(c1)CO/C2=C1/C(=O)Nc2ccccc21]

1-(2-Oxo-1,2-dihydro-indol-3-ylidene)-1,3-dihydro-isobenzofuran-5-carboxylic acid (2-diethylamino-ethyl)-amide

EXAMPLE 426

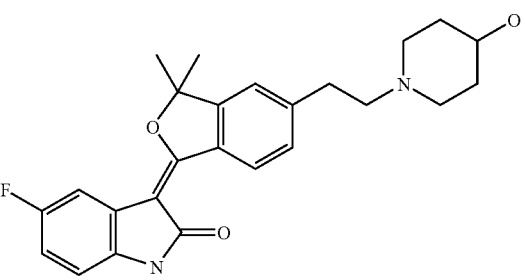 [SMILES: CC1(C)O/C(=C2/C(=O)Nc3ccc(F)cc32)c2ccc(CCN3CCC(O)CC3)cc21]

5-Fluoro-3-{5-[2-(4-hydroxy-piperidin-1-yl)-ethyl]-3,3-dimethyl-3H-isobenzofuran-1-ylidene}-1,3-dihydro-indol-2-one

EXAMPLE 521

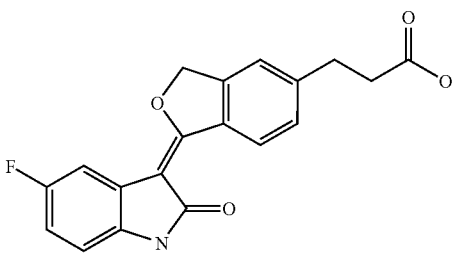 [SMILES: O=C(O)CCc1ccc2c(c1)CO/C2=C1/C(=O)Nc2ccc(F)cc21]

3-[1-(5-Fluoro-2-oxo-1,2-dihydro-indol-3-ylidene)-1,3-dihydro-isobenzofuran-5-yl]-propionic acid The following abbreviations may be used throughout this specification.

"Ac" refers to acetyl.
"Ar" refers to aryl.
"Tf" refers to triflate.
"Me" refers to methyl.
"Et" refers to ethyl.
"tBu" refers to t-butyl.
"iPr" refers to I-propyl.
"Ph" refers to phenyl.

"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutically acceptable salt" may also refer to those salts which retain the biological effectiveness and properties of the free acid and which are obtained by reaction with inorganic bases such as sodium hydroxide, potassium hydroxide or calcium hydroxide and the like or organic bases such as lysine, arginine, ethanolamine and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino, and SH.

"Alkenyl" refers to a straight-chain, branched or cyclic unsaturated hydrocarbon group containing at least one carbon-carbon double bond. Preferably, the alkenyl group has 1 to 12 carbons. More preferably it is a lower alkenyl of from 1 to 7 carbons, most preferably 1 to 4 carbons. The alkenyl group may be optionally substituted with one or more substituents selected from the group consisting of hydroxyl, cyano, alkoxy, =O, =S, $NO_2$, halogen, dimethyl amino, and SH.

"Alkynyl" refers to a straight-chain, branched or cyclic unsaturated hydrocarbon containing at least one carbon-carbon triple bond. Preferably, the alkynyl group has 1 to 12 carbons. More preferably it is a lower alkynyl of from 1 to 7 carbons, most preferably 1 to 4 carbons. The alkynyl group may be optionally substituted with one or more substituents selected from the group consisting of hydroxyl, cyano, alkoxy, =O, =S, $NO_2$, halogen, dimethyl amino, and SH.

"Alkoxyl" refers to an "O-alkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino.

"Alkaryl" refers to an alkyl that is covalently joined to an aryl group. Preferably, the alkyl is a lower alkyl.

"Carbocyclic aryl" refers to an aryl group wherein the ring atoms are carbon.

"Heterocyclic aryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Amide" refers to —C(O)—NH—R', wherein R' is alkyl, aryl, alkylaryl or hydrogen.

"Thioamide" refers to —C(S)—NH—R', wherein R' is alkyl, aryl, alkylaryl or hydrogen.

"Amine" refers to a —N(R")R'" group, wherein R" and R'" are independently selected from the group consisting of alkyl, aryl, and alkylaryl.

"Thioether" refers to —S—R", wherein R" is alkyl, aryl, or alkylaryl.

"Sulfonyl" refers to —S(O)$_2$—R"", where R"" is aryl, C(CN)=C-aryl, $CH_2CN$, alkylaryl, sulfonamide, NH-alkyl, NH-alkylaryl, or NH-aryl.

The compounds of Tables 3 through 7 are prepared by procedures analogous to the procedures used to prepare the compounds of Examples 1 through 27, which procedures are disclosed in U.S. Ser. Nos. 10/405,577 and 11/180,496. The synthesis of compounds of Examples 28 through 539 is, also, specifically described in U.S. patent application Ser. Nos. 10/405,577 and 11/180,496. These compounds, like the compounds of Examples 1 through 27, show activity as VEGF inhibitors.

TABLE 3

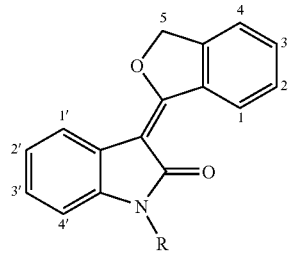

| Example Number | 1 | 2 | 3 | 4 | 5 | 1' | 2' | 3' | 4' | R |
|---|---|---|---|---|---|---|---|---|---|---|
| 28 | H | H | H | H | H,H | H | OMe | H | H | H |
| 29 | H | 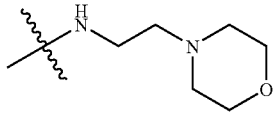 [SMILES: *NCCN1CCOCC1] | | | H | H | H,H | H | H | H | H |

TABLE 3-continued

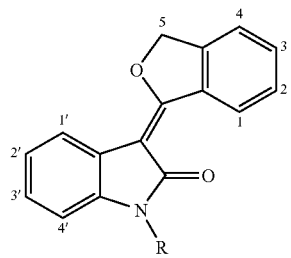

| Example Number | 1 | 2 | 3 | 4 | 5 | 1' | 2' | 3' | 4' | R |
|---|---|---|---|---|---|---|---|---|---|---|
| 28 | H | H | H | H | H, H | H | OMe | H | H | H |
| 30 | H | NHCOCH$_2$Br | H | H | H, H | H | Cl | H | H | H |
| 31 | H | ![morpholine acetamide] | H | H | H, H | H | Cl | H | H | H |
| 32 | H | ![piperidine acetamide] | H | H | H, H | H | Cl | H | H | H |
| 33 | H | ![diethylamino acetamide] | H | H | H, H | H | Cl | H | H | H |
| 34 | H | ![methylpiperazine acetamide] | H | H | H, H | H | Cl | H | H | H |
| 35 | H | NHCO$_2$C(CH$_3$)$_3$ | H | H | H, H | H | H | H | H | H |
| 36 | H | NHCO$_2$C(CH$_3$)$_3$ | H | H | H, H | H | Cl | H | H | H |
| 37 | H | ![2,4-dimethoxybenzylamino] | H | H | H, H | H | H | H | H | H |
| 38 | H | ![N-methyl-2,4-dimethoxybenzylamino] | H | H | H, H | H | H | H | H | —CH$_2$OH |
| 39 | H | NHCH$_3$ | H | H | H, H | H | H | H | H | —CH$_2$OH |
| 40 | H | NMe$_2$ | H | H | H, H | H | H | H | H | —CH$_2$OH |
| 41 | H | NHSO$_2$CH$_3$ | H | H | H, H | H | Cl | H | H | H |
| 42 | H | NHCOCH=CH$_2$ | H | H | H, H | H | Cl | H | H | H |

TABLE 4
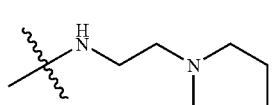
| Example Number | 1 | 2 | 3 | 4 | 5 | 1' | 2' | 3' | 4' | R |
|---|---|---|---|---|---|---|---|---|---|---|
| 43 | H | H | $NH_2$ | H | H, H | H | H | F | H | H |
| 44 | H | H | $NH_2$ | H | H, H | H | F | H | H | H |
| 45 | H | H | $NH(CH_2)_2Cl$ | H | H, H | H | H | H | H | H |
| 46 | H | H | $NH(CH_2)_2Cl$ | H | H, H | H | H | F | H | H |
| 47 | H | H | $NH(CH_2)_2Cl$ | H | H, H | H | F | H | H | H |
| 48 | H | H | 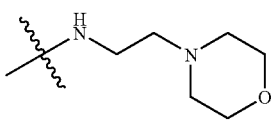 [SMILES: *NCCN1CCOCC1] | H | H, H | H | H | H | H | H |
| 49 | H | H | 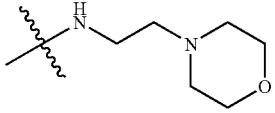 [SMILES: *NCCN1CCOCC1] | H | H, H | H | H | H | H | H |
| 50 | H | H | 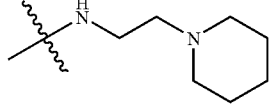 | H | H, H | H | H | F | H | H |
| 51 | H | H | 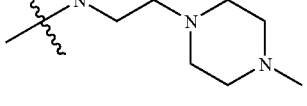 | H | H, H | H | H | F | H | H |
| 52 | H | H | 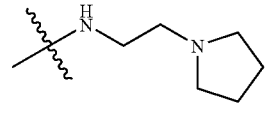 [SMILES: *NCCN1CCCC1] | H | H, H | H | H | H | H | H |
| 53 | H | H | 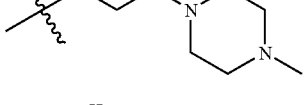 | H | H, H | H | H | H | H | H |
| 54 | H | H | 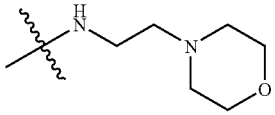 [SMILES: *NCCN1CCOCC1] | H | H, H | H | H | F | H | H |
| 55 | H | H | 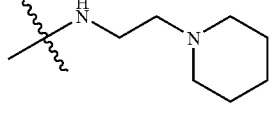 | H | H, H | H | F | H | H | H |
| 56 | H | H | 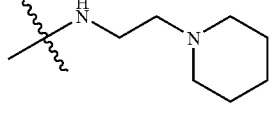 | H | H, H | H | F | H | H | H |

TABLE 4-continued

| Example Number | 1 | 2 | 3 | 4 | 5 | 1' | 2' | 3' | 4' | R |
|---|---|---|---|---|---|---|---|---|---|---|
| 57 | H | H | -NH-CH2CH2-N(piperazine-N-Me) | H | H,H | H | F | H | H | H |
| 58 | H | H | -NH-CH2CH2-N(2,6-dimethylmorpholine) | H | H,H | H | H | H | H | H |
| 59 | H | H | -NH-CH2CH2-N(2,6-dimethylmorpholine) | H | H,H | H | F | H | H | H |
| 60 | H | H | -NH-CH2CH2-N(2,6-dimethylmorpholine) | H | H,H | H | H | F | H | H |
| 61 | H | H | -NH-CH2CH2-N(3-fluoropyrrolidine) | H | H,H | H | H | H | H | H |
| 62 | H | H | -NH-CH2CH2-N(4-fluoropiperidine) | H | H,H | H | H | H | H | H |
| 63 | H | H | -NH-CH2CH2-N(Et)2 | H | H,H | H | F | H | H | H |
| 64 | H | H | -NH-CH2-(2,4-dimethoxyphenyl) | H | H,H | H | H | H | H | H |

TABLE 4-continued

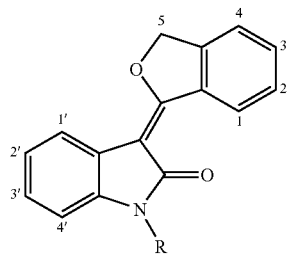

| Example Number | 1 | 2 | 3 | 4 | 5 | 1' | 2' | 3' | 4' | R |
|---|---|---|---|---|---|---|---|---|---|---|
| 65 | H | H | ![morpholinoethyl-N-(2,4-dimethoxybenzyl)] | H | H,H | H | H | H | H | H |
| 66 | H | H | ![N-methyl-N-(2,4-dimethoxybenzyl)] | H | H,H | H | H | F | H | H |
| 67 | H | H | ![N-methyl-N-(2,4-dimethoxybenzyl)] | H | H,H | H | H | H | H | H |
| 68 | H | H | ![N-methyl-N-(2,4-dimethoxybenzyl)] | H | H,H | H | Cl | H | H | H |
| 69 | H | H | ![N-methyl-N-(2,4-dimethoxybenzyl)] | H | H,H | H | H | H | F | H |
| 70 | H | H | ![N-methyl-N-(2,4-dimethoxybenzyl)] | H | H,H | H | F | H | H | H |
| 71 | H | H | ![N-methyl-N-(2,4-dimethoxybenzyl)] | H | H,H | H | H | Cl | H | H |
| 72 | H | H | NHCH$_3$ | H | H,H | H | H | F | H | H |
| 73 | H | H | NHCH$_3$ | H | H,H | H | F | H | H | H |

TABLE 4-continued

| Example Number | 1 | 2 | 3 | 4 | 5 | 1' | 2' | 3' | 4' | R |
|---|---|---|---|---|---|---|---|---|---|---|
| 74 | H | H | NHCH$_3$ | H | H,H | H | Cl | H | H | H |
| 75 | H | H | NHCH$_3$ | H | H,H | H | H | Cl | H | H |
| 76 | H | H | NHCH$_3$ | H | H,H | H | H | H | F | H |
| 77 | H | H | N(CH$_3$)$_2$ | H | H,H | H | Cl | H | H | H |
| 78 | H | H | NHC(C$_6$H$_5$)$_3$ | H | H,H | H | Cl | H | H | H |
| 79 | H | H | N(CH$_2$C$_6$H$_5$)$_2$ | H | H,H | H | Cl | H | H | H |
| 80 | H | H | ~~~CH(CH$_3$)(CH$_2$)$_3$OH | H | H,H | H | H | H | H | H |
| 81 | H | H | ~~~CH(CH$_3$)(CH$_2$)$_3$OSO$_2$Me | H | H,H | H | H | H | H | H |
| 82 | H | H | ~~~CH(CH$_3$)(CH$_2$)$_3$-morpholino | H | H,H | H | H | H | H | H |
| 83 | H | H | ~~~CH(CH$_3$)(CH$_2$)$_3$-thiomorpholino | H | H,H | H | H | H | H | H |
| 84 | H | H | ~~~C(CH$_3$)N(CH$_3$)CH$_2$CH$_2$Cl | H | H,H | H | H | H | H | H |
| 85 | H | H | ~~~C(CH$_3$)N(CH$_3$)CH$_2$CH$_2$-morpholino | H | H,H | H | H | H | H | H |
| 86 | H | H | ~~~C(CH$_3$)N(CH$_3$)CH$_2$CH$_2$-morpholino | H | H,H | H | F | H | H | H |
| 87 | H | H | ~~~C(CH$_3$)NHC(O)CH$_2$Br | H | H,H | H | Cl | H | H | H |
| 88 | H | H | ~~~C(CH$_3$)NHC(O)CH$_2$-morpholino | H | H,H | H | Cl | H | H | H |

TABLE 4-continued

| Example Number | 1 | 2 | 3 | 4 | 5 | 1' | 2' | 3' | 4' | R |
|---|---|---|---|---|---|---|---|---|---|---|
| 89 | H | H | ⸺NH-C(O)-CH₂-morpholinyl | H | H,H | H | H | H | H | H |
| 90 | H | H | ⸺NH-C(O)-CH₂-N(Et)₂ | H | H,H | H | Cl | H | H | H |
| 91 | H | H | ⸺NH-C(O)-CH₂-(4-methylpiperazinyl) | H | H,H | H | Cl | H | H | H |
| 92 | H | H | ⸺NH-C(O)-CH₂-piperidinyl | H | H,H | H | Cl | H | H | H |
| 93 | H | H | NH(CH₂)₂OH | H | H,H | H | H | H | H | H |
| 94 | H | H | NH(CH₂)₂OH | H | H,H | H | H | F | H | H |
| 95 | H | H | NH(CH₂)₂OCOCH₃ | H | H,H | H | H | H | H | H |
| 96 | H | H | NH(CH₂)₂OCOCH₃ | H | H,H | H | H | F | H | H |
| 97 | H | H | ⸺NH-(CH₂)₂-O-C(O)-CH₂Br | H | H,H | H | H | H | H | H |
| 98 | H | H | ⸺NH-(CH₂)₂-O-C(O)-CH₂-morpholinyl | H | H,H | H | H | H | H | H |
| 99 | H | H | ⸺NH-(CH₂)₂-O-C(O)-CH₂-N(Et)₂ | H | H,H | H | H | H | H | H |
| 100 | H | H | ⸺NH-(CH₂)₂-O-C(O)-CH₂-(4-methylpiperazinyl) | H | H,H | H | H | H | H | H |

TABLE 4-continued

| Example Number | 1 | 2 | 3 | 4 | 5 | 1' | 2' | 3' | 4' | R |
|---|---|---|---|---|---|---|---|---|---|---|
| 101 | H | H | ~NH-CH₂CH₂-O-C(O)-CH₂-N(piperidine) | H | H,H | H | H | H | H | H |
| 102 | H | H | Br | H | H,H | H | H | H | H | H |
| 103 | H | H | ~C≡C-CH₂-NMe₂ | H | H,H | H | H | H | H | H |
| 104 | H | H | ~(CH₂)₃-NMe₂ | H | H,H | H | H | H | H | H |
| 135 | H | H | ~NH-CH₂CH₂-N(morpholine) | H | H,H | H | Cl | H | H | H |

TABLE 5

| Example Number | 1 | 2 | 3 | 4 | 5 | 1' | 2' | 3' | 4' | R |
|---|---|---|---|---|---|---|---|---|---|---|
| 105 | H | H | H | H | —(CH₂)₂NH(CH₂)₂— | H | H | H | H | H |
| 106 | H | H | H | H | —CH₂COOH | H | H | H | H | H |
| 107 | H | H | H | H | —CH₂COOH | H | Cl | H | H | H |
| 108 | H | H | H | H | —CH₂COOH | H | H | F | H | H |
| 109 | H | H | H | H | —CH₂CH₂OH | H | H | H | H | H |
| 110 | H | H | H | H | —(CH₂)₂OSO₂CH₃ | H | H | H | H | H |
| 111 | H | H | H | H | ~C(CH₃)₂-CH₂CH₂-N(pyrrolidine) | H | H | H | H | H |

TABLE 5-continued

| Example Number | 1 | 2 | 3 | 4 | 5 | 1' | 2' | 3' | 4' | R |
|---|---|---|---|---|---|---|---|---|---|---|
| 112 | H | H | H | H | -CH2CH2-morpholine | H | H | H | H | H |
| 113 | H | H | H | H | -CH2CH2-N(Et)2 | H | H | H | H | H |
| 114 | H | H | H | H | -CH2CH2-N(propyl)(CH2CH2OCH3) | H | H | H | H | H |
| 115 | H | H | H | H | -CH2CH2-azetidinyl | H | H | H | H | H |
| 116 | H | H | H | H | —CH$_2$N(CH$_3$)$_2$ | H | H | H | H | H |
| 117 | H | H | H | H | —CH$_2$NCO | H | H | H | H | H |
| 118 | H | H | H | H | —CH$_2$NHCONH$_2$ | H | H | H | H | H |
| 119 | H | H | H | H | —CH$_2$NHCO$_2$C$_2$H$_5$ | H | H | H | H | H |
| 120 | H | H | H | H | -CH2-NHC(O)NH-CH2CH2-morpholine | H | H | H | H | H |
| 121 | H | H | H | H | -CH2-NHC(O)-piperidine | H | H | H | H | H |
| 122 | H | H | H | H | -CH2-NHC(O)NH-CH2CH2-OH | H | H | H | H | H |
| 123 | H | H | H | H | -CH2-C(O)O-CH2CH2-morpholine | H | H | H | H | H |

TABLE 5-continued

[Structure: isobenzofuran-indolin-2-one core with positions 1-5 on benzofuran ring and 1'-4' on indolinone ring, N-R substituent]

| Example Number | 1 | 2 | 3 | 4 | 5 | 1' | 2' | 3' | 4' | R |
|---|---|---|---|---|---|---|---|---|---|---|
| 124 | H | H | H | H | [CH₂C(O)OCH₂CH₂-piperidine] | H | H | F | H | H |
| 125 | H | H | H | H | —CH₂CO₂CH₃ | H | H | F | H | H |
| 126 | H | H | H | H | —COOH | H | H | H | H | H |
| 127 | H | H | H | H | [CH₂-tetrazole] | H | H | H | H | H |
| 128 | H | H | H | H | —CH₂CONH₂ | H | H | H | H | H |
| 129 | H | H | H | H | Me | H | H | H | H | H |
| 130 | H | H | H | H | 2xMe | H | H | H | H | H |
| 131 | H | H | OMe | H | —CH₂COOH | H | H | H | H | H |
| 132 | H | OMe | H | H | —CH₂COOH | H | H | H | H | H |
| 133 | H | H | H | H | —CH₂COONa | H | H | H | H | H |
| 134 | H | H | H | H | —CH₂COONa | H | H | F | H | H |

TABLE 6

[Structure: isobenzofuran-indolin-2-one core with positions 1-5 on benzofuran ring and 1'-4' on indolinone ring, N-R substituent]

| Example Number | 1 | 2 | 3 | 4 | 5 | 1' | 2' | 3' | 4' | R |
|---|---|---|---|---|---|---|---|---|---|---|
| 136 | H | H | —O-CH₂CH₂-morpholine | H | H, H | H | OMe | F | H | H |
| 137 | H | H | —O-CH₂CH₂-morpholine | H | H, H | H | F | H | H | H |
| 138 | H | H | —O-CH₂CH₂-morpholine | H | H, H | H | Cl | H | H | H |

TABLE 6-continued

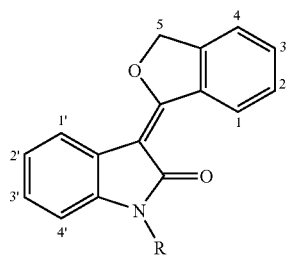

| Example Number | 1 | 2 | 3 | 4 | 5 | 1' | 2' | 3' | 4' | R |
|---|---|---|---|---|---|---|---|---|---|---|
| 139 | H | H | ⸺O⸺CH₂CH₂⸺N(morpholine) | H | H,H | H | ⸺NH⸺CH₂⸺(2,4-diOMe-phenyl) | OMe F | H | H |

TABLE 7

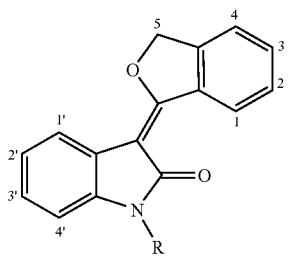

| Example Number | Chemical Structure | Chemical Name | Molecular Weight |
|---|---|---|---|
| 140 | 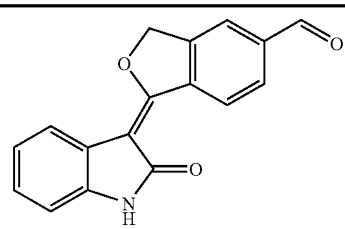 | 1-(2-Oxo-1,2-dihydro-indol-3-ylidene)-1,3-dihydro-isobenzofuran-5-carbaldehyde | 277.278 |
| 141 | 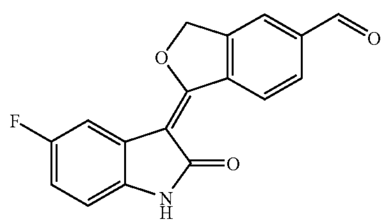 [SMILES: O=Cc1ccc2c(c1)CO/C2=C1/C(=O)Nc2ccc(F)cc21] | 1-(5-Fluoro-2-oxo-1,2-dihydro-indol-3-ylidene)-1,3-dihydro-isobenzofuran-5-carbaldehyde | 295.268 |
| 142 | 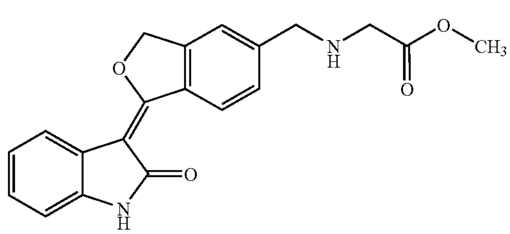 [SMILES: COC(=O)CNCc1ccc2c(c1)CO/C2=C1/C(=O)Nc2ccccc21] | {[1-(2-Oxo-1,2-dihydro-indol-3-ylidene)-1,3-dihydro-isobenzofuran-5-ylmethyl]-amino}-acetic acid methyl ester | 350.372 |

TABLE 7-continued

| Example Number | Chemical Structure | Chemical Name | Molecular Weight |
|---|---|---|---|
| 143 | 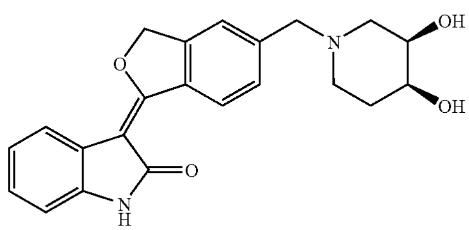 [SMILES: O=C1Nc2ccccc2/C1=C1\OCc2cc(CN3CC[C@H](O)[C@H](O)C3)ccc21] | cis-3-[5-(3,4-Dihydroxy-piperidin-1-ylmethyl)-3H-isobenzofuran-1-ylidene]-1,3-dihydro-indol-2-one | 378.426 |
| 144 | 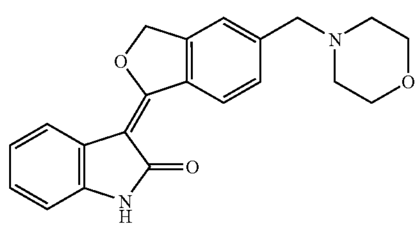 [SMILES: O=C1Nc2ccccc2/C1=C1\OCc2cc(CN3CCOCC3)ccc21] | 3-(5-Morpholin-4-ylmethyl-3H-isobenzofuran-1-ylidene)-1,3-dihydro-indol-2-one | 348.4 |
| 145 | 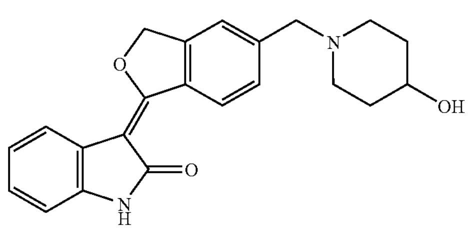 [SMILES: O=C1Nc2ccccc2/C1=C1\OCc2cc(CN3CCC(O)CC3)ccc21] | 3-[5-(4-Hydroxy-piperidin-1-ylmethyl)-3H-isobenzofuran-1-ylidene]-1,3-dihydro-indol-2-one | 362.427 |
| 146 | 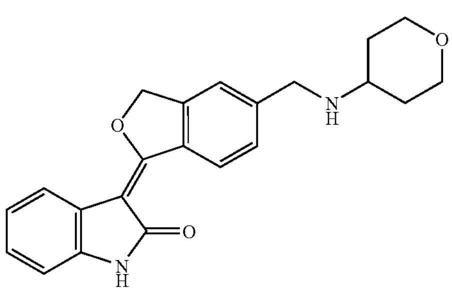 [SMILES: O=C1Nc2ccccc2/C1=C1\OCc2cc(CNC3CCOCC3)ccc21] | 3-{5-[(Tetrahydro-pyran-4-ylamino)-methyl]-3H-isobenzofuran-1-ylidene}-1,3-dihydro-indol-2-one | 362.427 |
| 147 | 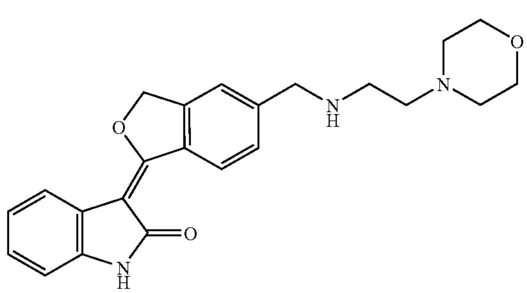 [SMILES: O=C1Nc2ccccc2/C1=C1\OCc2cc(CNCCN3CCOCC3)ccc21] | 3-{5-[(2-Morpholin-4-yl-ethylamino)-methyl]-3H-isobenzofuran-1-ylidene}-1,3-dihydro-indol-2-one | 391.469 |

TABLE 7-continued

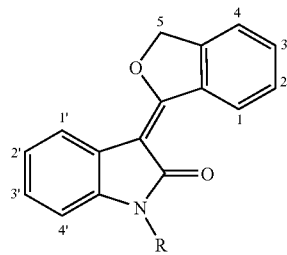

| Example Number | Chemical Structure | Chemical Name | Molecular Weight |
|---|---|---|---|
| 148 | 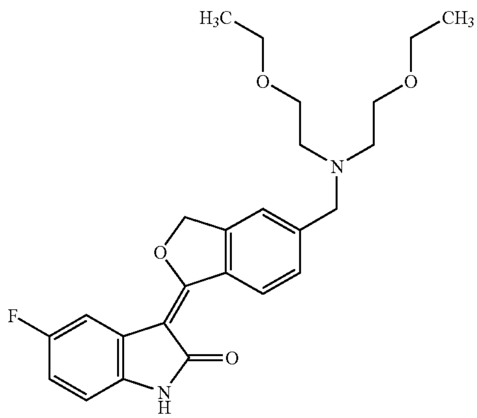 [SMILES: CCOCCN(CCOCC)Cc1ccc2c(c1)CO/C2=C1/C(=O)Nc2ccc(F)cc21] | 3-(5-{[Bis-(2-ethoxy-ethyl)-amino]-methyl}-3H-isobenzofuran-1-ylidene)-5-fluoro-1,3-dihydro-indol-2-one | 440.512 |
| 149 | 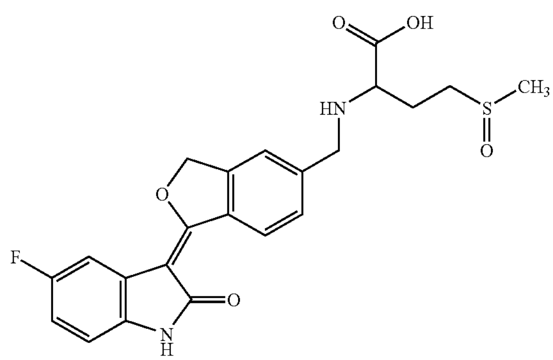 [SMILES: CS(=O)CCC(NCc1ccc2c(c1)CO/C2=C1/C(=O)Nc2ccc(F)cc21)C(=O)O] | 2-{[1-(5-Fluoro-2-oxo-1,2-dihydro-indol-3-ylidene)-1,3-dihydro-isobenzofuran-5-ylmethyl]-amino}-4-methanesulfinyl-butyric acid | 444.481 |
| 150 | 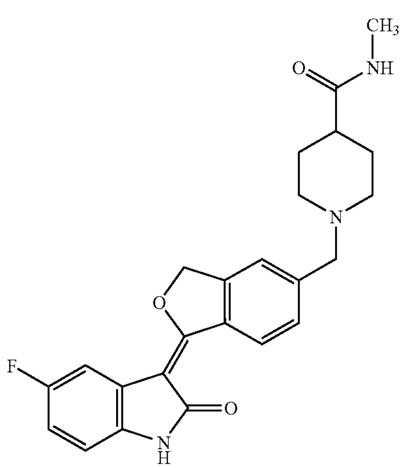 [SMILES: CNC(=O)C1CCN(Cc2ccc3c(c2)CO/C3=C2/C(=O)Nc3ccc(F)cc32)CC1] | 1-[1-(5-Fluoro-2-oxo-1,2-dihydro-indol-3-ylidene)-1,3-dihydro-isobenzofuran-5-ylmethyl]-piperidine-4-carboxylic acid methylamide | 421.47 |

TABLE 7-continued
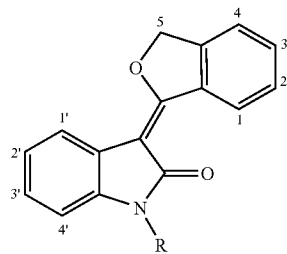
| Example Number | Chemical Structure | Chemical Name | Molecular Weight |
|---|---|---|---|
| 151 | 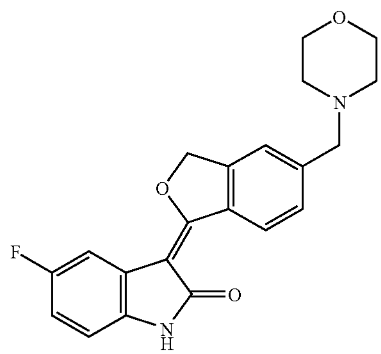 [SMILES: O=C1Nc2ccc(F)cc2/C1=C1\OCc2cc(CN3CCOCC3)ccc21] | 5-Fluoro-3-(5-morpholin-4-ylmethyl-3H-isobenzofuran-1-ylidene)-1,3-dihydro-indol-2-one | 366.39 |
| 152 | 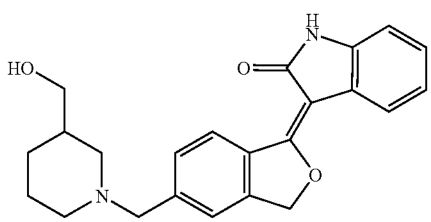 [SMILES: O=C1Nc2ccccc2/C1=C1\OCc2cc(CN3CCCC(CO)C3)ccc21] | 3-[5-(3-Hydroxymethyl-piperidin-1-ylmethyl)-3H-isobenzofuran-1-ylidene]-1,3-dihydro-indol-2-one | 376.454 |
| 153 | 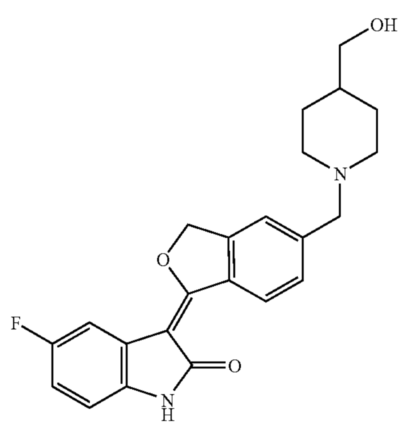 [SMILES: O=C1Nc2ccc(F)cc2/C1=C1\OCc2cc(CN3CCC(CO)CC3)ccc21] | 5-Fluoro-3-[5-(4-hydroxymethyl-piperidin-1-ylmethyl)-3H-isobenzofuran-1-ylidene]-1,3-dihydro-indol-2-one | 394.444 |

TABLE 7-continued

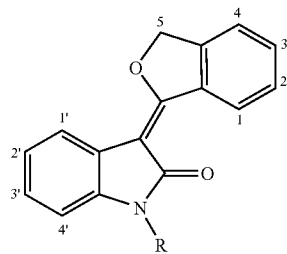

| Example Number | Chemical Structure | Chemical Name | Molecular Weight |
|---|---|---|---|
| 154 | 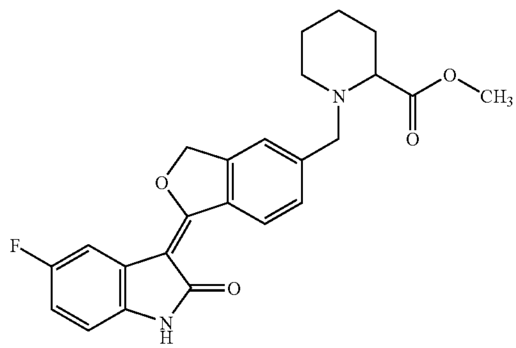 [SMILES: COC(=O)C1CCCCN1Cc1ccc2c(c1)CO/C2=C1/C(=O)Nc2ccc(F)cc21] | 1-[1-(5-Fluoro-2-oxo-1,2-dihydro-indol-3-ylidene)-1,3-dihydro-isobenzofuran-5-ylmethyl]-piperidine-2-carboxylic acid methyl ester | 422.454 |
| 155 | 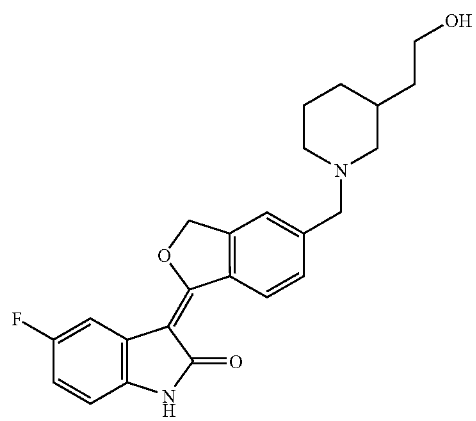 [SMILES: O=C1Nc2ccc(F)cc2/C1=C1\OCc2cc(CN3CCCC(CCO)C3)ccc21] | 5-Fluoro-3-{5-[3-(2-hydroxy-ethyl)-piperidin-1-ylmethyl]-3H-isobenzofuran-1-ylidene}-1,3-dihydro-indol-2-one | 408.47 |
| 156 | 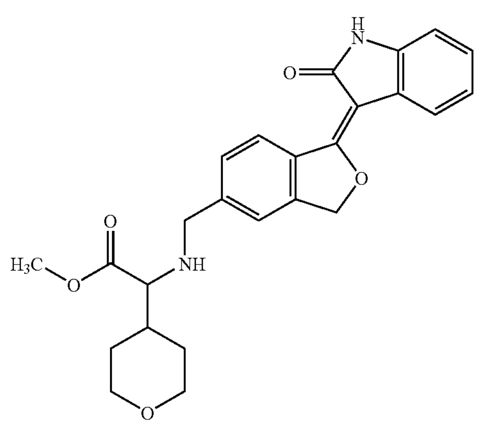 [SMILES: COC(=O)C(NCc1ccc2c(c1)CO/C2=C1/C(=O)Nc2ccccc21)C1CCOCC1] | {[1-(2-Oxo-1,2-dihydro-indol-3-ylidene)-1,3-dihydro-isobenzofuran-5-ylmethyl]-amino}-(tetrahydro-pyran-4-yl)-acetic acid methyl ester | 434.489 |

US 8,455,656 B2
TABLE 7-continued
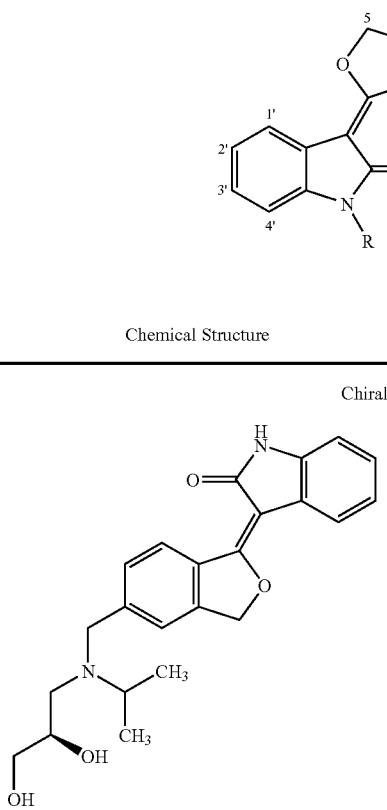
| Example Number | Chemical Structure | Chemical Name | Molecular Weight |
|---|---|---|---|
| 157 | Chiral 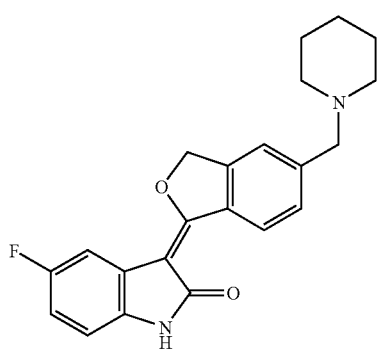 [SMILES: O=C1Nc2ccc(F)cc2/C1=C1\OCc2cc(CN3CCCCC3)ccc21] | 3-(5-{[((2S)-2,3-Dihydroxy-propyl)-isopropyl-amino]-methyl}-3H-isobenzofuran-1-ylidene)-1,3-dihydro-indol-2-one | 394.468 |
| 158 | 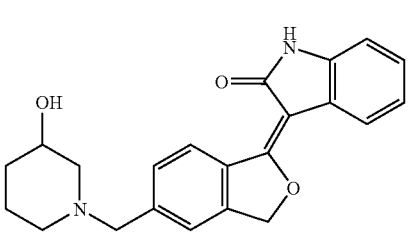 | 5-Fluoro-3-(5-piperidin-1-ylmethyl-3H-isobenzofuran-1-ylidene)-1,3-dihydro-indol-2-one | 364.418 |
| 159 | 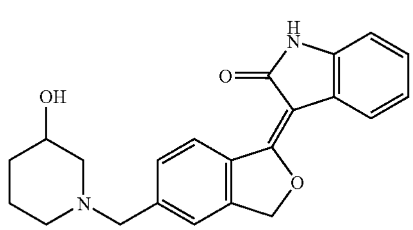 [SMILES: O=C1Nc2ccccc2/C1=C1\OCc2cc(CN3CCCC(O)C3)ccc21] | 3-[5-(3-Hydroxy-piperidin-1-ylmethyl)-3H-isobenzofuran-1-ylidene]-1,3-dihydro-indol-2-one | 362.427 |

TABLE 7-continued

| Example Number | Chemical Structure | Chemical Name | Molecular Weight |
|---|---|---|---|
| 160 | 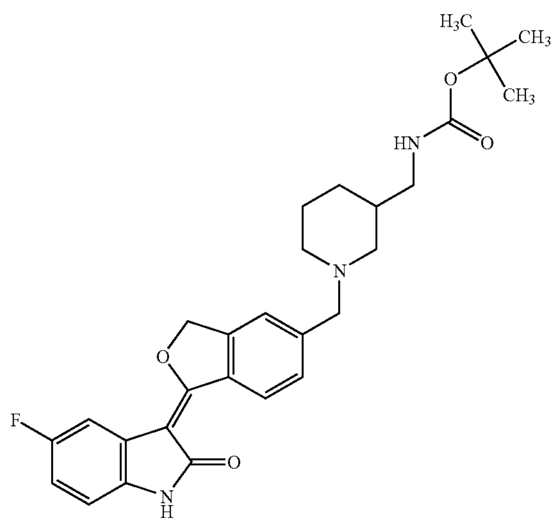 [SMILES: CC(C)(C)OC(=O)NCC1CCCN(Cc2ccc3c(c2)CO/C3=C2/C(=O)Nc3ccc(F)cc32)C1] | {1-[1-(5-Fluoro-2-oxo-1,2-dihydro-indol-3-ylidene)-1,3-dihydro-isobenzofuran-5-ylmethyl]-piperidin-3-ylmethyl}-carbamic acid tert-butyl ester | 493.576 |
| 161 | 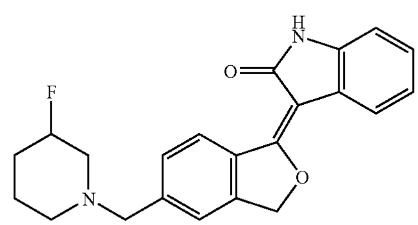 [SMILES: O=C1Nc2ccccc2/C1=C1\OCc2cc(CN3CCCC(F)C3)ccc21] | 3-[5-(3-Fluoro-piperidin-1-ylmethyl)-3H-isobenzofuran-1-ylidene]-1,3-dihydro-indol-2-one | 364.418 |
| 162 | 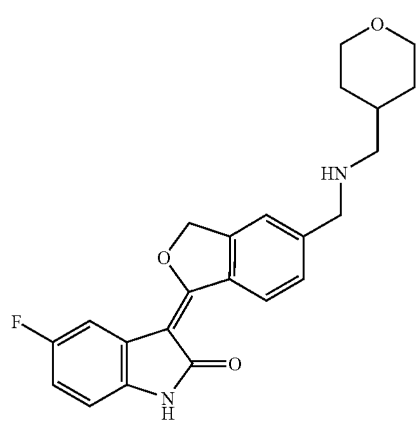 [SMILES: O=C1Nc2ccc(F)cc2/C1=C1\OCc2cc(CNCC3CCOCC3)ccc21] | 5-Fluoro-3-(5-{[(tetrahydro-pyran-4-ylmethyl)-amino]-methyl}-3H-isobenzofuran-1-ylidene)-1,3-dihydro-indol-2-one | 394.444 |

TABLE 7-continued

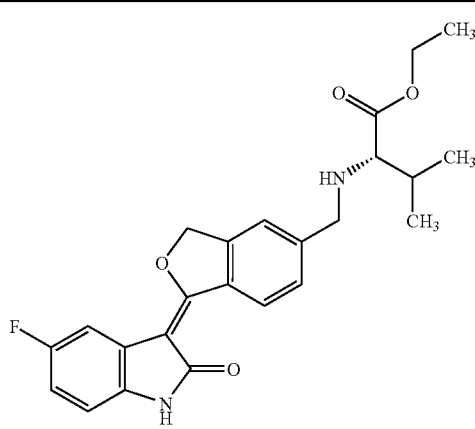

| Example Number | Chemical Structure | Chemical Name | Molecular Weight |
|---|---|---|---|
| 163 | 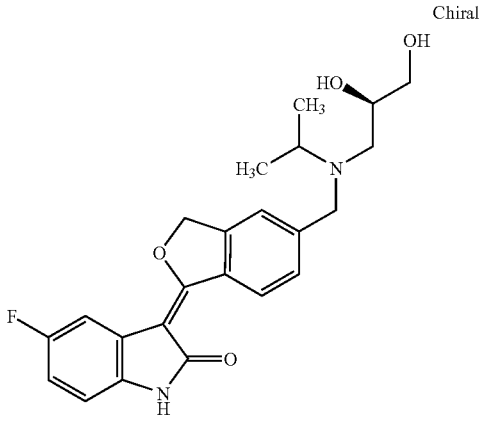 [SMILES: CC(C)N(Cc1ccc2c(c1)CO/C2=C1/C(=O)Nc2ccc(F)cc21)C[C@@H](O)CO] | (S)-2-{[1-(5-Fluoro-2-oxo-1,2-dihydro-indol-3-ylidene)-1,3-dihydro-isobenzofuran-5-ylmethyl]-amino}-3-methyl-butyric acid ethyl ester | 424.47 |
| 164 | 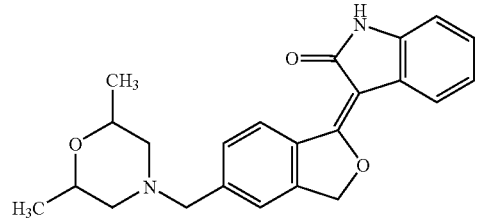 Chiral | 3-(5-{[((2R)-2,3-Dihydroxy-propyl)-isopropyl-amino]-methyl}-3H-isobenzofuran-1-ylidene)-5-fluoro-1,3-dihydro-indol-2-one | 412.458 |
| 165 | 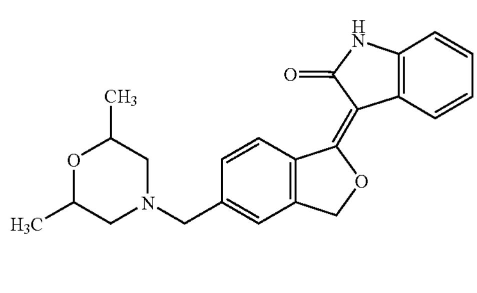 [SMILES: CC1CN(Cc2ccc3c(c2)CO/C3=C2/C(=O)Nc3ccccc32)CC(C)O1] | 3-[5-(2,6-Dimethyl-morpholin-4-ylmethyl)-3H-isobenzofuran-1-ylidene]-1,3-dihydro-indol-2-one | 376.454 |

TABLE 7-continued

| Example Number | Chemical Structure | Chemical Name | Molecular Weight |
|---|---|---|---|
| 166 | 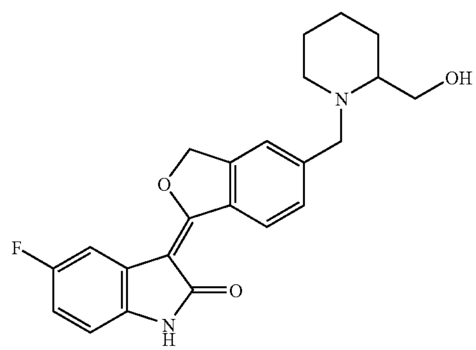 [SMILES: O=C1Nc2ccc(F)cc2/C1=C1\OCc2cc(CN3CCCCC3CO)ccc21] | 5-Fluoro-3-[5-(2-hydroxymethyl-piperidin-1-ylmethyl)-3H-isobenzofuran-1-ylidene]-1,3-dihydro-indol-2-one | 394.444 |
| 167 | 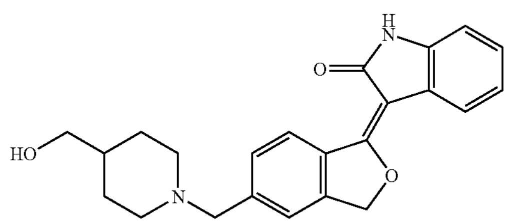 [SMILES: O=C1Nc2ccccc2/C1=C1\OCc2cc(CN3CCC(CO)CC3)ccc21] | 3-[5-(4-Hydroxymethyl-piperidin-1-ylmethyl)-3H-isobenzofuran-1-ylidene]-1,3-dihydro-indol-2-one | 376.454 |
| 168 | Chiral | 1-[1-(2-Oxo-1,2-dihydro-indol-3-ylidene)-1,3-dihydro-isobenzofuran-5-ylmethyl]-pyrrolidine-(S)-2-carboxylic acid ethyl ester | 404.464 |
| 169 | 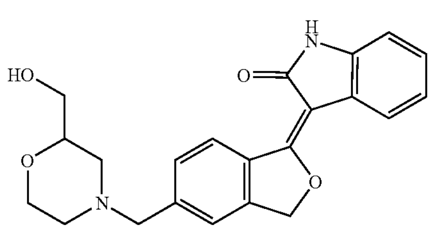 | 3-[5-(2-Hydroxymethyl-morpholin-4-ylmethyl)-3H-isobenzofuran-1-ylidene]-1,3-dihydro-indol-2-one | 378.426 |

TABLE 7-continued

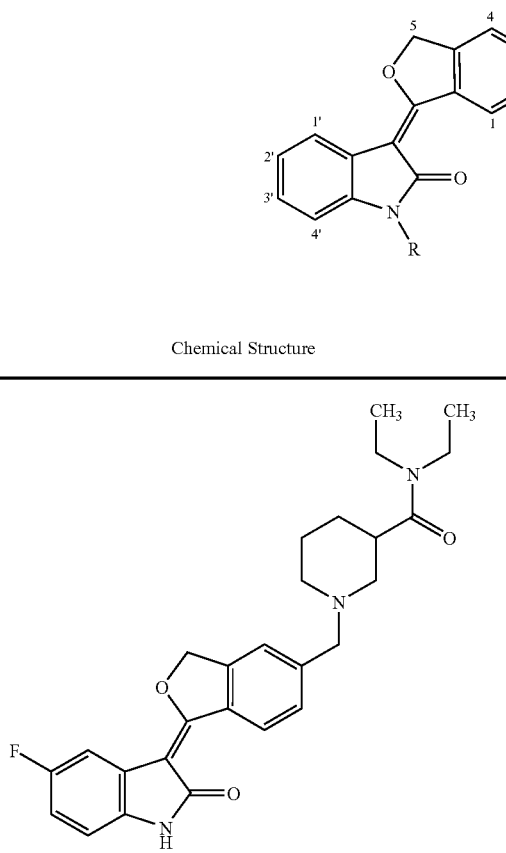

| Example Number | Chemical Structure | Chemical Name | Molecular Weight |
|---|---|---|---|
| 170 | 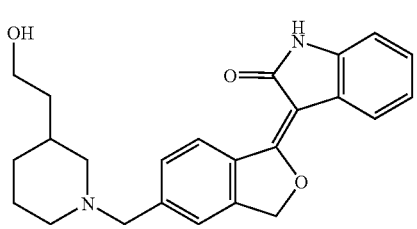 [SMILES: O=C1Nc2ccccc2/C1=C1\OCc2cc(CN3CCCC(CCO)C3)ccc21] | 1-[1-(5-Fluoro-2-oxo-1,2-dihydro-indol-3-ylidene)-1,3-dihydro-isobenzofuran-5-ylmethyl]-piperidine-3-carboxylic acid diethylamide | 463.55 |
| 171 | 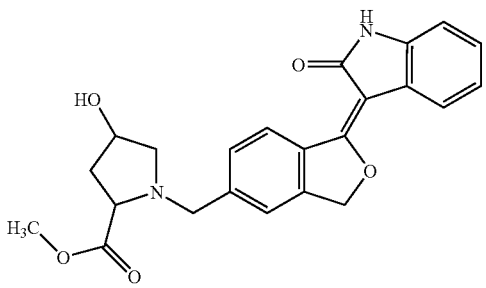 [SMILES: COC(=O)C1CC(O)CN1Cc1ccc2c(c1)CO/C2=C1/C(=O)Nc2ccccc21] | 3-{5-[3-(2-Hydroxy-ethyl)-piperidin-1-ylmethyl]-3H-isobenzofuran-1-ylidene}-1,3-dihydro-indol-2-one | 390.48 |
| 172 | 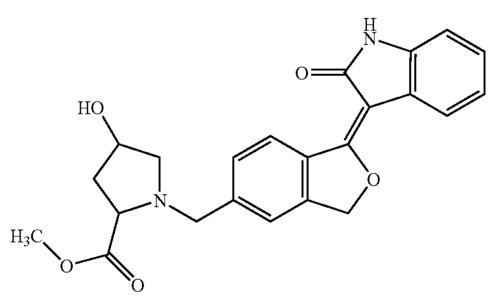 | 4-Hydroxy-1-[1-(2-oxo-1,2-dihydro-indol-3-ylidene)-1,3-dihydro-isobenzofuran-5-ylmethyl]-pyrrolidine-2-carboxylic acid methyl ester | 406.436 |

TABLE 7-continued

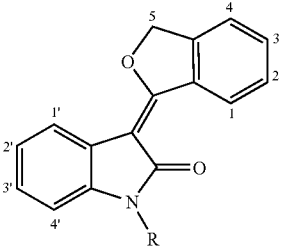

| Example Number | Chemical Structure | Chemical Name | Molecular Weight |
|---|---|---|---|
| 173 | 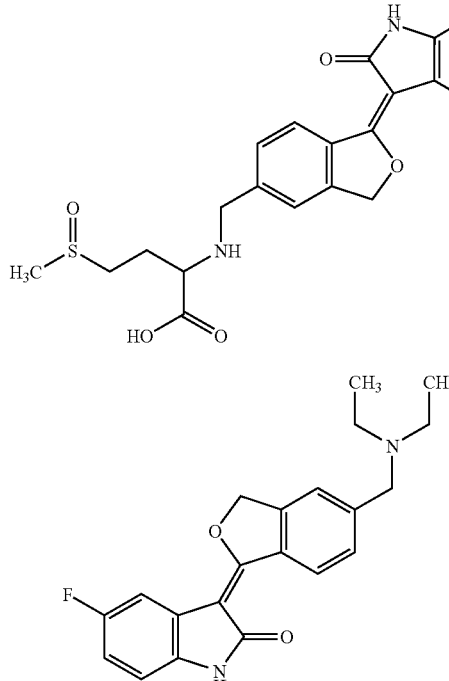 | 4-Methanesulfinyl-2-{[1-(2-oxo-1,2-dihydro-indol-3-ylidene)-1,3-dihydro-isobenzofuran-5-ylmethyl]-amino}-butyric acid | 426.491 |
| 174 | 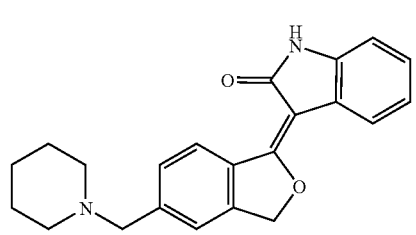 [SMILES: O=C1Nc2ccccc2/C1=C1\OCc2cc(CN3CCCCC3)ccc21] | 3-(5-Diethylaminomethyl-3H-isobenzofuran-1-ylidene)-5-fluoro-1,3-dihydro-indol-2-one | 352.407 |
| 175 | 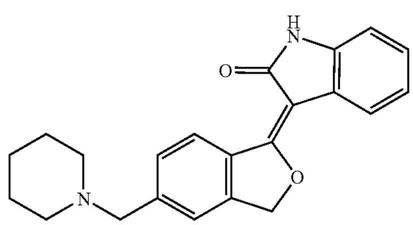 | 3-(5-Piperidin-1-ylmethyl-3H-isobenzofuran-1-ylidene)-1,3-dihydro-indol-2-one | 346.428 |
| 176 | 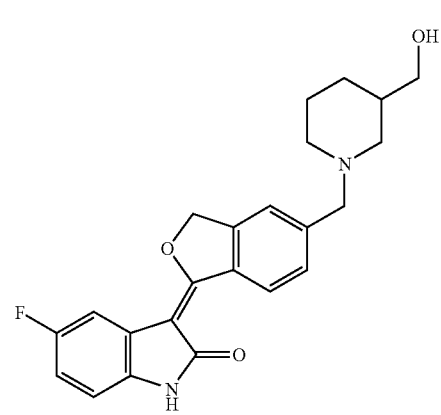 [SMILES: O=C1Nc2ccc(F)cc2/C1=C1\OCc2cc(CN3CCCC(CO)C3)ccc21] | 5-Fluoro-3-[5-(3-hydroxymethyl-piperidin-1-ylmethyl)-3H-isobenzofuran-1-ylidene]-1,3-dihydro-indol-2-one | 394.444 |

TABLE 7-continued

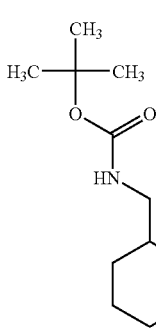

| Example Number | Chemical Structure | Chemical Name | Molecular Weight |
|---|---|---|---|
| 177 | 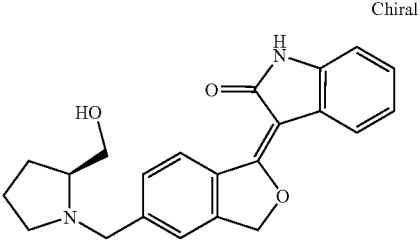 [SMILES: O=C1Nc2ccccc2/C1=C1\OCc2cc(CN3CCC[C@H]3CO)ccc21] | {1-[1-(2-Oxo-1,2-dihydro-indol-3-ylidene)-1,3-dihydro-isobenzofuran-5-ylmethyl]-piperidin-3-ylmethyl}-carbamic acid tert-butyl ester | 475.586 |
| 178 | Chiral 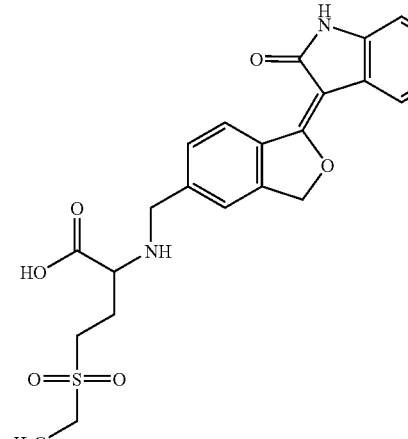 | 3-[5-((S)-2-Hydroxymethyl-pyrrolidin-1-ylmethyl)-3H-isobenzofuran-1-ylidene]-1,3-dihydro-indol-2-one | 362.427 |
| 179 | 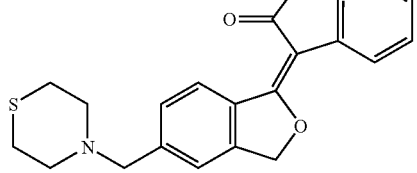 | 4-Ethanesulfonyl-2-{[1-(2-oxo-1,2-dihydro-indol-3-ylidene)-1,3-dihydro-isobenzofuran-5-ylmethyl]-amino}-butyric acid | 456.517 |
| 180 | 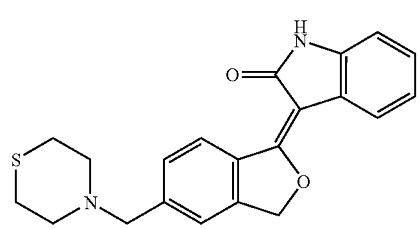 [SMILES: O=C1Nc2ccccc2/C1=C1\OCc2cc(CN3CCSCC3)ccc21] | 3-(5-Thiomorpholin-4-ylmethyl-3H-isobenzofuran-1-ylidene)-1,3-dihydro-indol-2-one | 364.467 |

TABLE 7-continued
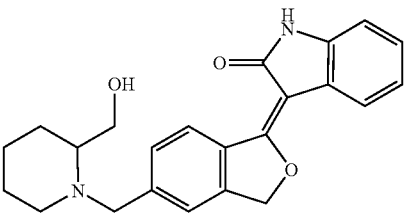 [SMILES: O=C1Nc2ccccc2/C1=C1\OCc2cc(CN3CCCCC3CO)ccc21]
| Example Number | Chemical Structure | Chemical Name | Molecular Weight |
|---|---|---|---|
| 181 | 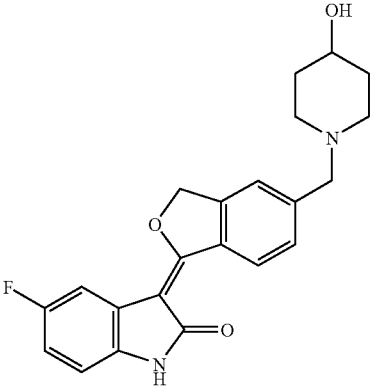 [SMILES: O=C1Nc2ccc(F)cc2/C1=C1\OCc2cc(CN3CCC(O)CC3)ccc21] | 3-[5-(2-Hydroxymethyl-piperidin-1-ylmethyl)-3H-isobenzofuran-1-ylidene]-1,3-dihydro-indol-2-one | 376.454 |
| 182 | 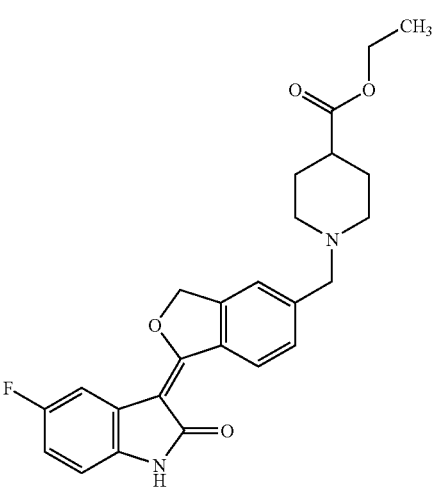 | 5-Fluoro-3-[5-(4-hydroxy-piperidin-1-ylmethyl)-3H-isobenzofuran-1-ylidene]-1,3-dihydro-indol-2-one | 380.417 |
| 183 | 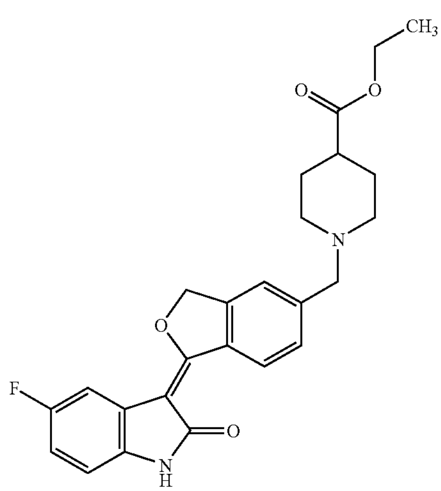 [SMILES: CCOC(=O)C1CCN(Cc2ccc3c(c2)CO/C3=C2/C(=O)Nc3ccc(F)cc32)CC1] | 1-[1-(5-Fluoro-2-oxo-1,2-dihydro-indol-3-ylidene)-1,3-dihydro-isobenzofuran-5-ylmethyl]-piperidine-4-carboxylic acid ethyl ester | 436.48 |

TABLE 7-continued

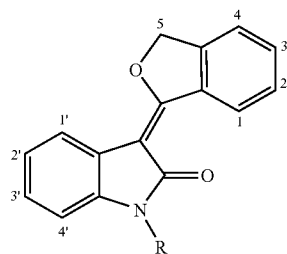

| Example Number | Chemical Structure | Chemical Name | Molecular Weight |
|---|---|---|---|
| 184 | Chiral | 1-[1-(2-Oxo-1,2-dihydro-indol-3-ylidene)-1,3-dihydro-isobenzofuran-5-ylmethyl]-pyrrolidine-(S)-2-carboxylic acid methyl ester | 390.437 |
| 185 | 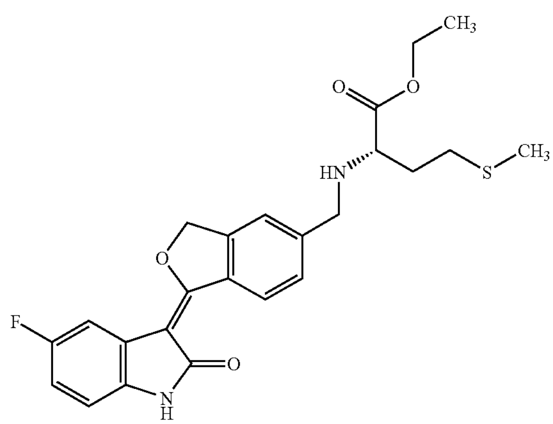 [SMILES: CCOC(=O)[C@H](CCSC)NCc1ccc2c(c1)CO/C2=C1/C(=O)Nc2ccc(F)cc21] | (S)-2-{[1-(5-Fluoro-2-oxo-1,2-dihydro-indol-3-ylidene)-1,3-dihydro-isobenzofuran-5-ylmethyl]-amino}-4-methylsulfanyl-butyric acid ethyl ester | 456.535 |
| 186 | 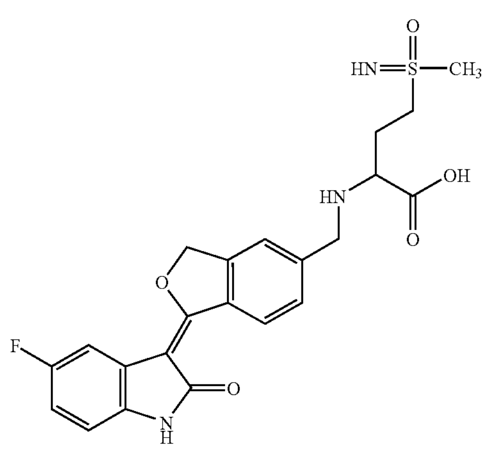 [SMILES: CS(=N)(=O)CCC(NCc1ccc2c(c1)CO/C2=C1/C(=O)Nc2ccc(F)cc21)C(=O)O] | 4-Methylsulfonimidosyl-2-{[1-(5-fluoro-2-oxo-1,2-dihydro-indol-3-ylidene)-1,3-dihydro-isobenzofuran-5-ylmethyl]-amino}-butanoic acid | 459.496 |

…

TABLE 7-continued

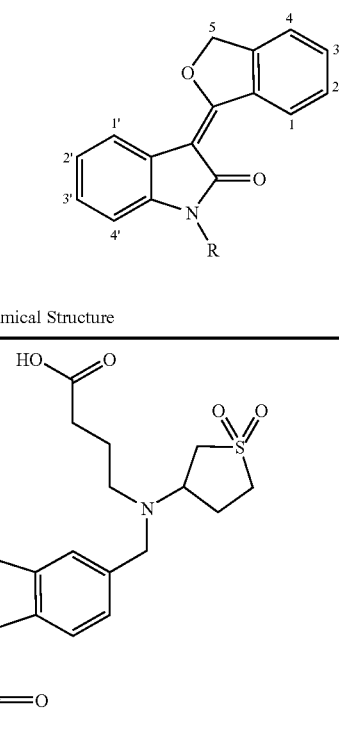

| Example Number | Chemical Structure | Chemical Name | Molecular Weight |
|---|---|---|---|
| 187 | 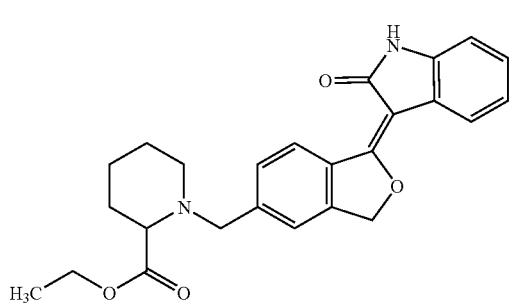 [SMILES: CCOC(=O)C1CCCCN1Cc1ccc2c(c1)CO/C2=C1/C(=O)Nc2ccccc21] | 4-{(1,1-Dioxo-tetrahydro-1lambda*6*-thiophen-3-yl)-[1-(5-fluoro-2-oxo-1,2-dihydro-indol-3-ylidene)-1,3-dihydro-isobenzofuran-5-ylmethyl]-amino}-butyric acid | 500.544 |
| 188 | 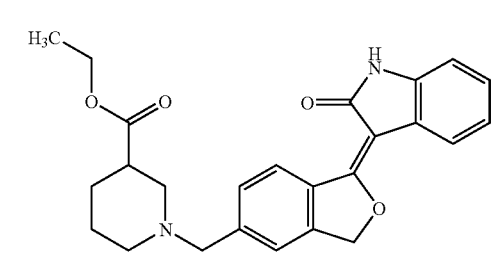 | 1-[1-(2-Oxo-1,2-dihydro-indol-3-ylidene)-1,3-dihydro-isobenzofuran-5-ylmethyl]-piperidine-2-carboxylic acid ethyl ester | 418.49 |
| 189 | 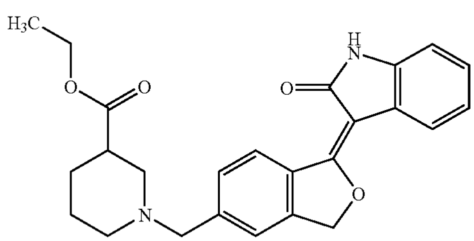 [SMILES: CCOC(=O)C1CCCN(Cc2ccc3c(c2)CO/C3=C2/C(=O)Nc3ccccc32)C1] | 1-[1-(2-Oxo-1,2-dihydro-indol-3-ylidene)-1,3-dihydro-isobenzofuran-5-ylmethyl]-piperidine-3-carboxylic acid ethyl ester | 418.49 |
| 190 | 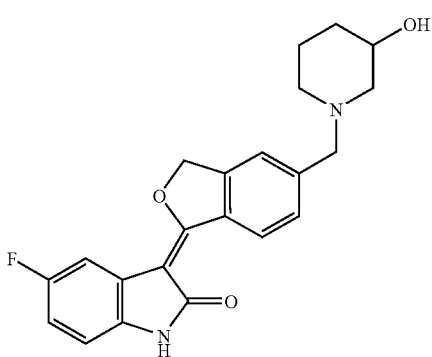 [SMILES: O=C1Nc2ccc(F)cc2/C1=C1\OCc2cc(CN3CCCC(O)C3)ccc21] | 5-Fluoro-3-[5-(3-hydroxy-piperidin-1-ylmethyl)-3H-isobenzofuran-1-ylidene]-1,3-dihydro-indol-2-one | 380.417 |

TABLE 7-continued

| Example Number | Chemical Structure | Chemical Name | Molecular Weight |
|---|---|---|---|
| 191 | 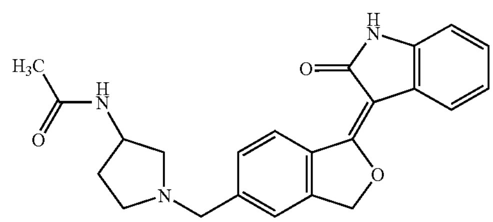 [SMILES: CC(=O)NC1CCN(Cc2ccc3c(c2)CO/C3=C2/C(=O)Nc3ccccc32)C1] | N-{1-[1-(2-Oxo-1,2-dihydro-indol-3-ylidene)-1,3-dihydro-isobenzofuran-5-ylmethyl]-pyrrolidin-3-yl}-acetamide | 389.453 |
| 192 | 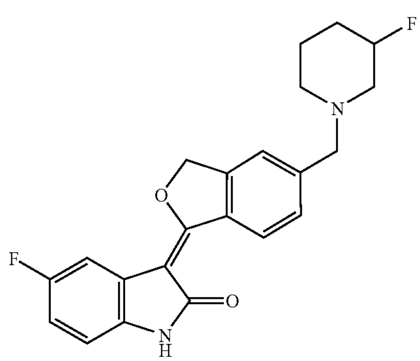 [SMILES: O=C1Nc2ccc(F)cc2/C1=C1\OCc2cc(CN3CCCC(F)C3)ccc21] | 5-Fluoro-3-[5-(3-fluoro-piperidin-1-ylmethyl)-3H-isobenzofuran-1-ylidene]-1,3-dihydro-indol-2-one | 382.408 |
| 193 | 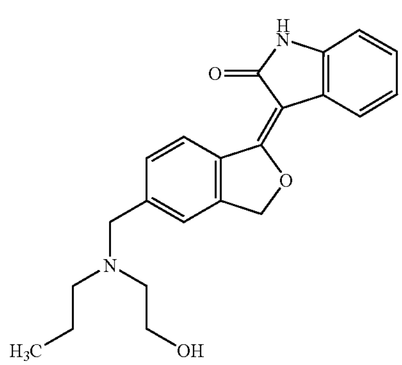 [SMILES: CCCN(CCO)Cc1ccc2c(c1)CO/C2=C1/C(=O)Nc2ccccc21] | 3-(5-{[(2-Hydroxy-ethyl)-propyl-amino]-methyl}-3H-isobenzofuran-1-ylidene)-1,3-dihydro-indol-2-one | 364.443 |

TABLE 7-continued

| Example Number | Chemical Structure | Chemical Name | Molecular Weight |
|---|---|---|---|
| 194 | 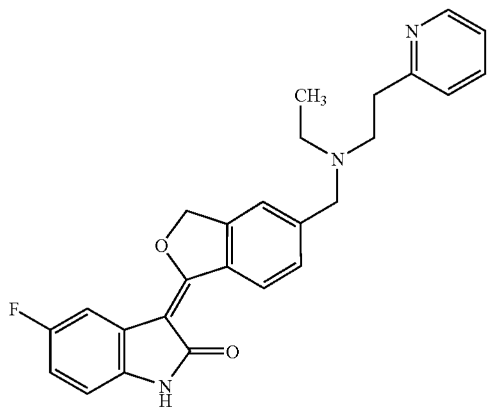 [SMILES: CCN(CCc1ccccn1)Cc1ccc2c(c1)CO/C2=C1/C(=O)Nc2ccc(F)cc21] | 3-(5-{[Ethyl-(2-pyridin-2-yl-ethyl)-amino]-methyl}-3H-isobenzofuran-1-ylidene)-5-fluoro-1,3-dihydro-indol-2-one | 429.493 |
| 195 | 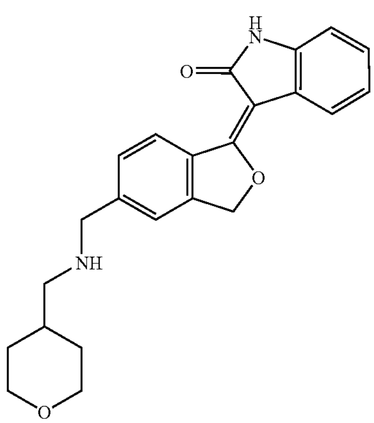 [SMILES: O=C1Nc2ccccc2/C1=C1\OCc2cc(CNCC3CCOCC3)ccc21] | 3-(5-{[(Tetrahydro-pyran-4-ylmethyl)-amino]-methyl}-3H-isobenzofuran-1-ylidene)-1,3-dihydro-indol-2-one | 376.454 |
| 196 | Chiral | 1-[1-(5-Fluoro-2-oxo-1,2-dihydro-indol-3-ylidene)-1,3-dihydro-isobenzofuran-5-ylmethyl]-pyrrolidine-(S)-2-carboxylic acid ethyl ester | 422.454 |

TABLE 7-continued
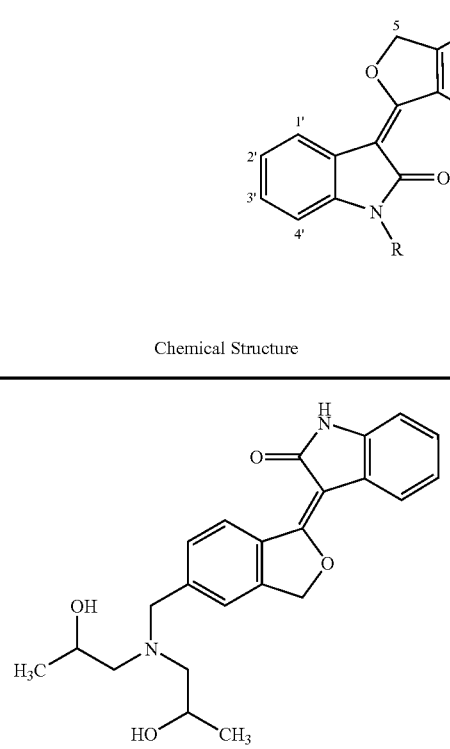
| Example Number | Chemical Structure | Chemical Name | Molecular Weight |
|---|---|---|---|
| 197 | 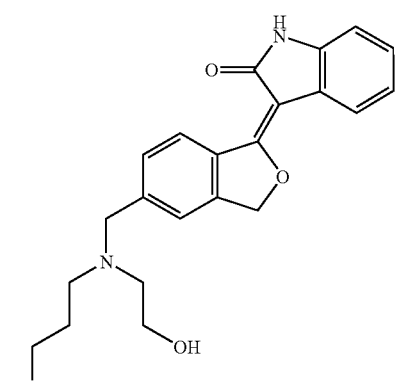 | 3-(5-{[Bis-(2-hydroxy-propyl)-amino]-methyl}-3H-isobenzofuran-1-ylidene)-1,3-dihydro-indol-2-one | 394.468 |
| 198 | 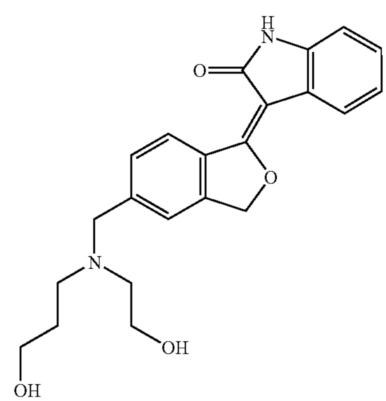 [SMILES: O=C1Nc2ccccc2/C1=C1\OCc2cc(CN(CCO)CCCO)ccc21] | 3-(5-{[(2-Hydroxy-ethyl)-(3-hydroxy-propyl)-amino]-methyl}-3H-isobenzofuran-1-ylidene)-1,3-dihydro-indol-2-one | 380.442 |
| 199 | 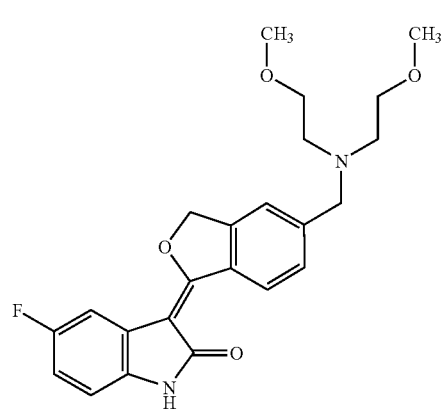 [SMILES: COCCN(CCOC)Cc1ccc2c(c1)CO/C2=C1/C(=O)Nc2ccc(F)cc21] | 3-(5-{[Bis-(2-methoxy-ethyl)-amino]-methyl}-3H-isobenzofuran-1-ylidene)-5-fluoro-1,3-dihydro-indol-2-one | 412.458 |

TABLE 7-continued

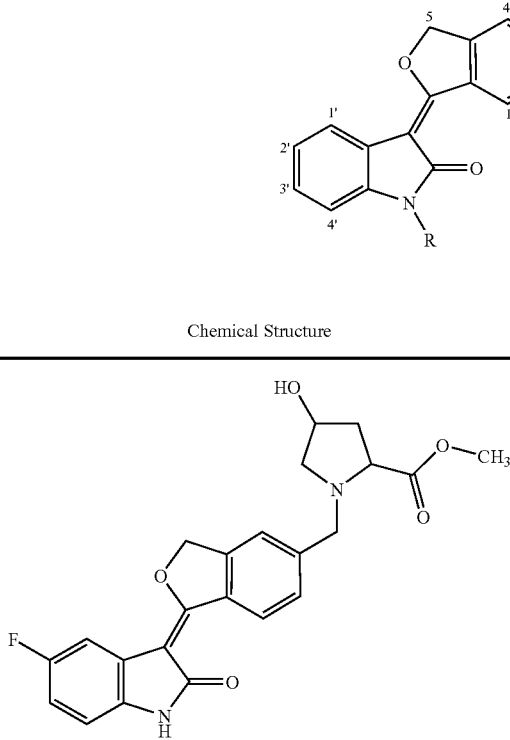

| Example Number | Chemical Structure | Chemical Name | Molecular Weight |
|---|---|---|---|
| 200 | 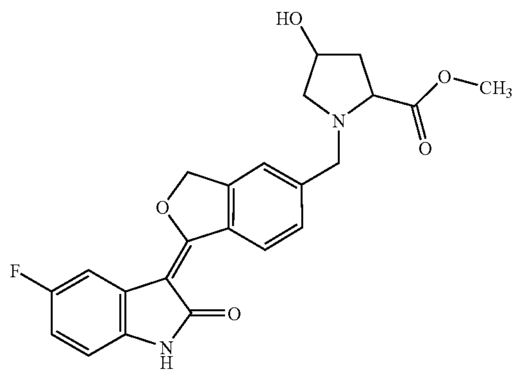 [SMILES: COC(=O)C1CC(O)CN1Cc1ccc2c(c1)CO/C2=C1/C(=O)Nc2ccc(F)cc21] | 1-[1-(5-Fluoro-2-oxo-1,2-dihydro-indol-3-ylidene)-1,3-dihydro-isobenzofuran-5-ylmethyl]-4-hydroxy-pyrrolidine-2-carboxylic acid methyl ester | 424.426 |
| 201 | Chiral | 3-[5-((S,S)-2,5-Bis-methoxymethyl-pyrrolidin-1-ylmethyl)-3H-isobenzofuran-1-ylidene]-1,3-dihydro-indol-2-one | 420.506 |
| 202 | 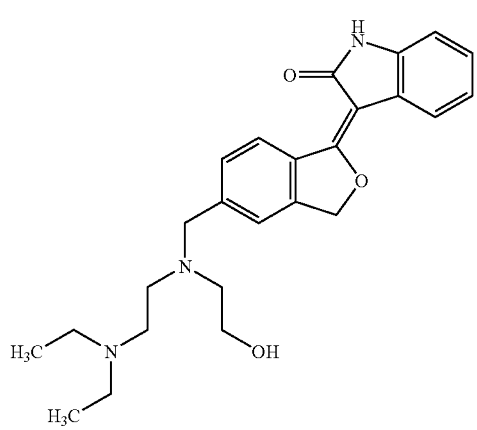 [SMILES: CCN(CC)CCN(CCO)Cc1ccc2c(c1)CO/C2=C1/C(=O)Nc2ccccc21] | 3-(5-{[(2-Diethylamino-ethyl)-(2-hydroxy-ethyl)-amino]-methyl}-3H-isobenzofuran-1-ylidene)-1,3-dihydro-indol-2-one | 421.538 |

TABLE 7-continued
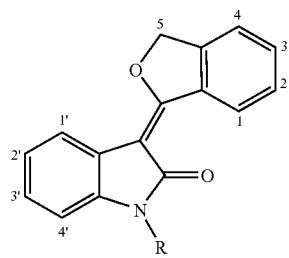
| Example Number | Chemical Structure | Chemical Name | Molecular Weight |
|---|---|---|---|
| 203 | 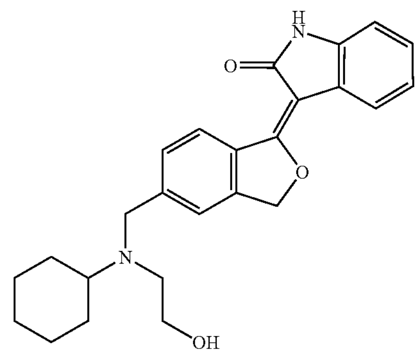 [SMILES: O=C1Nc2ccccc2/C1=C1\OCc2cc(CN(CCO)C3CCCCC3)ccc21] | 3-(5-{[Cyclohexyl-(2-hydroxy-ethyl)-amino]-methyl}-3H-isobenzofuran-1-ylidene)-1,3-dihydro-indol-2-one | 404.507 |
| 204 | 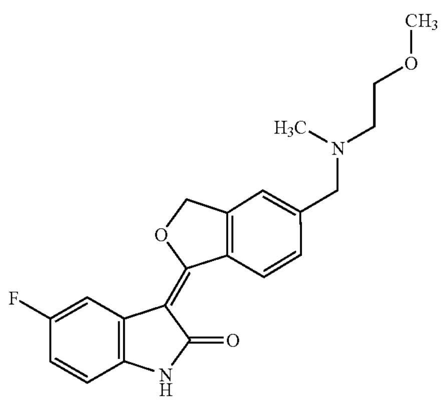 [SMILES: COCCN(C)Cc1ccc2c(c1)CO/C2=C1/C(=O)Nc2ccc(F)cc21] | 5-Fluoro-3-(5-{[(2-methoxy-ethyl)-methyl-amino]-methyl}-3H-isobenzofuran-1-ylidene)-1,3-dihydro-indol-2-one | 368.406 |
| 205 | Chiral | (R)-3-Methoxy-(S)-2-{[1-(2-oxo-1,2-dihydro-indol-3-ylidene)-1,3-dihydro-isobenzofuran-5-ylmethyl]-amino}-butyric acid | 394.425 |

TABLE 7-continued
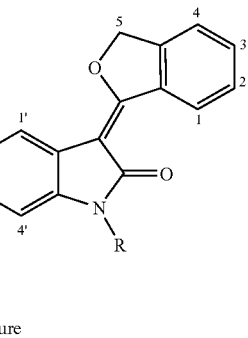
| Example Number | Chemical Structure | Chemical Name | Molecular Weight |
|---|---|---|---|
| 206 | 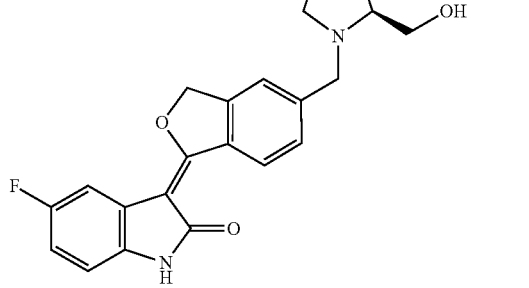 Chiral | 5-Fluoro-3-{5-[(S)-2-hydroxymethyl-pyrrolidin-1-ylmethyl}-3H-isobenzofuran-1-ylidene]-1,3-dihydro-indol-2-one | 380.417 |
| 207 | 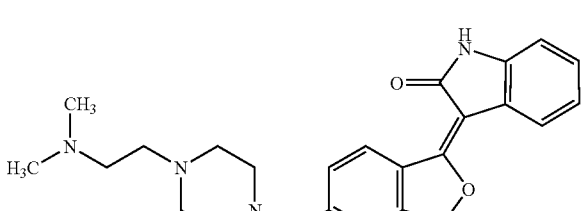 | 3-{5-[4-(2-Dimethylamino-ethyl)-piperazin-1-ylmethyl]-3H-isobenzofuran-1-ylidene}-1,3-dihydro-indol-2-one | 418.538 |
| 208 | 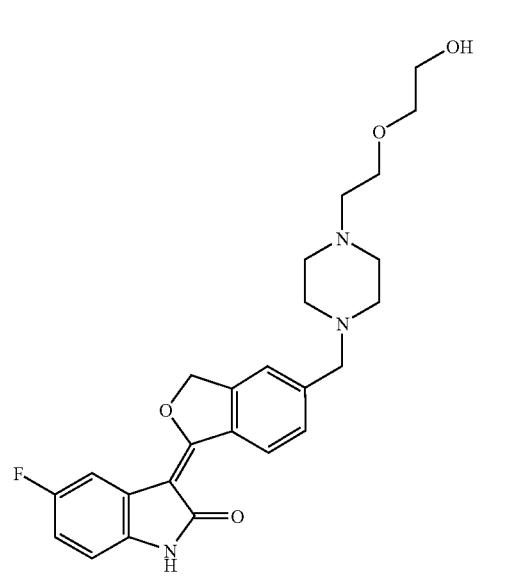 [SMILES: O=C1Nc2ccc(F)cc2/C1=C1\OCc2cc(CN3CCN(CCOCCO)CC3)ccc21] | 5-Fluoro-3-(5-{4-[2-(2-hydroxy-ethoxy)-ethyl]-piperazin-1-ylmethyl}-3H-isobenzofuran-1-ylidene)-1,3-dihydro-indol-2-one | 453.511 |

TABLE 7-continued

| Example Number | Chemical Structure | Chemical Name | Molecular Weight |
|---|---|---|---|
| 209 | 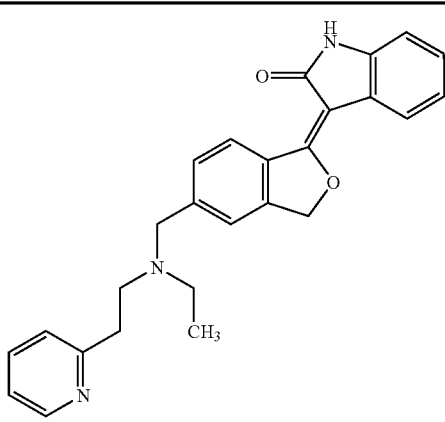 | 3-(5-{[Ethyl-(2-pyridin-2-yl-ethyl)-amino]-methyl}-3H-isobenzofuran-1-ylidene)-1,3-dihydro-indol-2-one | 411.503 |
| 210 | Chiral 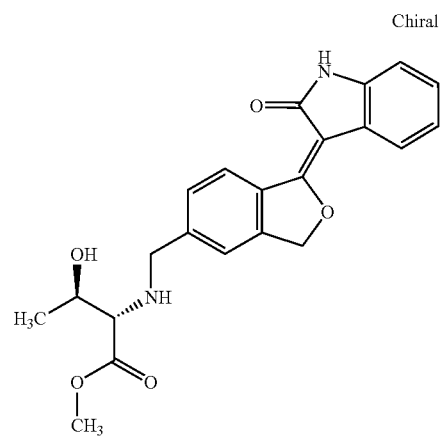 [SMILES: COC(=O)[C@@H](NCc1ccc2c(c1)CO/C2=C1/C(=O)Nc2ccccc21)[C@@H](C)O] | (R)-3-Hydroxy-(S)-2-{[1-(2-oxo-1,2-dihydro-indol-3-ylidene)-1,3-dihydro-isobenzofuran-5-ylmethyl]-amino}-butyric acid methyl ester | 394.425 |
| 211 | Chiral 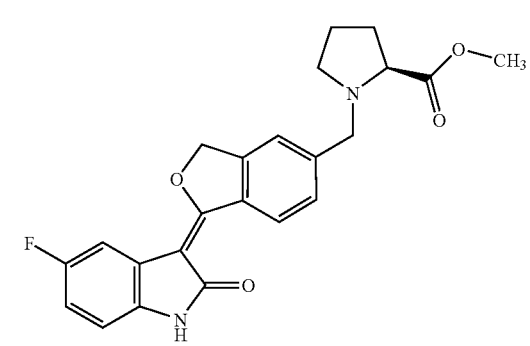 | 1-[1-(5-Fluoro-2-oxo-1,2-dihydro-indol-3-ylidene)-1,3-dihydro-isobenzofuran-5-ylmethyl]-pyrrolidine-(S)-2-carboxylic acid methyl ester | 408.427 |

TABLE 7-continued
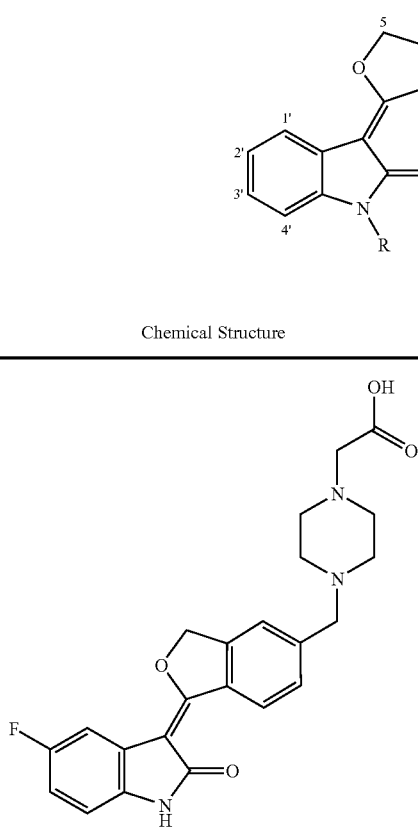
| Example Number | Chemical Structure | Chemical Name | Molecular Weight |
|---|---|---|---|
| 212 | 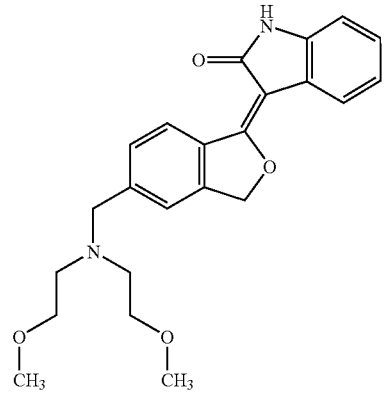 [SMILES: COCCN(CCOC)Cc1ccc2c(c1)CO/C2=C1/C(=O)Nc2ccccc21] | {4-[1-(5-Fluoro-2-oxo-1,2-dihydro-indol-3-ylidene)-1,3-dihydro-isobenzofuran-5-ylmethyl]-piperazin-1-yl}-acetic acid | 423.442 |
| 213 | 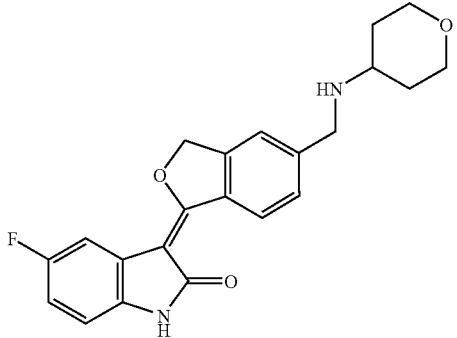 | 3-(5-{[Bis-(2-methoxy-ethyl)-amino]-methyl}-3H-isobenzofuran-1-ylidene)-1-dihydro-indol-2-one | 394.468 |
| 214 | 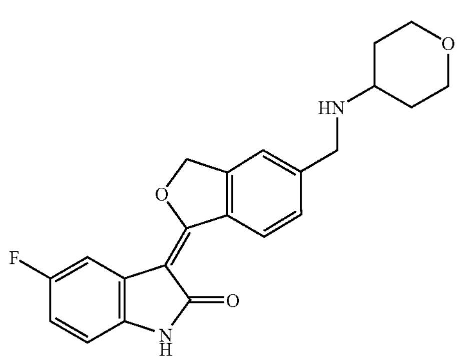 [SMILES: O=C1Nc2ccc(F)cc2/C1=C1\OCc2cc(CNC3CCOCC3)ccc21] | 5-Fluoro-3-{5-[(tetrahydro-pyran-4-ylamino)-methyl]-3H-isobenzofuran-1-ylidene}-1,3-dihydro-indol-2-one | 380.417 |

TABLE 7-continued
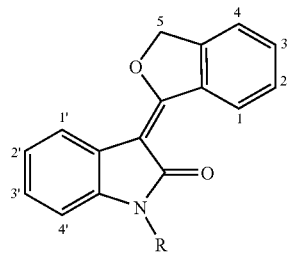
| Example Number | Chemical Structure | Chemical Name | Molecular Weight |
|---|---|---|---|
| 215 | 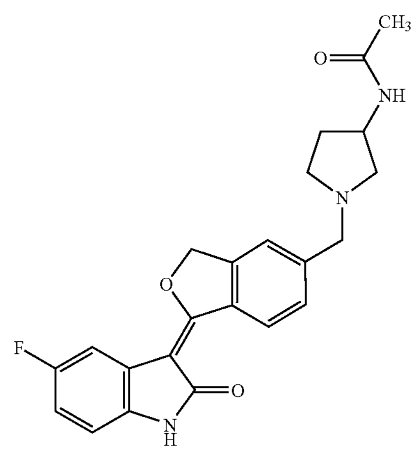 [SMILES: CC(=O)NC1CCN(Cc2ccc3c(c2)CO/C3=C2/C(=O)Nc3ccc(F)cc32)C1] | N-{1-[1-(5-Fluoro-2-oxo-1,2-dihydro-indol-3-ylidene)-1,3-dihydro-isobenzofuran-5-ylmethyl]-pyrrolidin-3-yl}-acetamide | 407.443 |
| 216 | 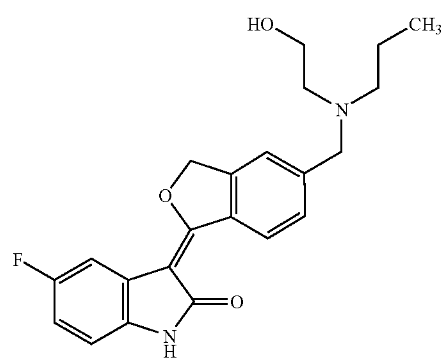 [SMILES: CCCN(CCO)Cc1ccc2c(c1)CO/C2=C1/C(=O)Nc2ccc(F)cc21] | 5-Fluoro-3-(5-{[(2-hydroxy-ethyl)-propyl-amino]-methyl}-3H-isobenzofuran-1-ylidene)-1,3-dihydro-indol-2-one | 382.433 |
| 217 | 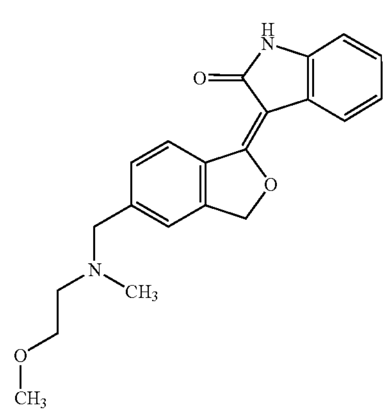 [SMILES: COCCN(C)Cc1ccc2c(c1)CO/C2=C1/C(=O)Nc2ccccc21] | 3-(5-{[(2-Methoxy-ethyl)-methyl-amino]-methyl}-3H-isobenzofuran-1-ylidene)-1,3-dihydro-indol-2-one | 350.416 |

TABLE 7-continued

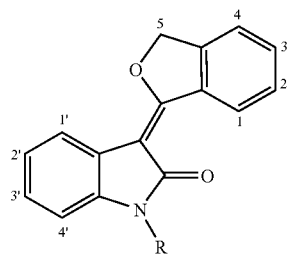

| Example Number | Chemical Structure | Chemical Name | Molecular Weight |
|---|---|---|---|
| 218 | 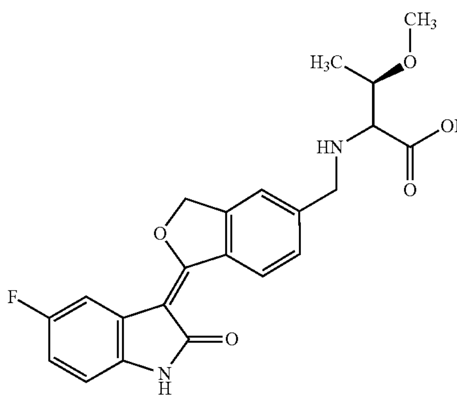 | (S)-2-{[1-(5-Fluoro-2-oxo-1,2-dihydro-indol-3-ylidene)-1,3-dihydro-isobenzofuran-5-ylmethyl]-amino}-(R)-3-methoxy-butyric acid | 412.415 |
| 219 | 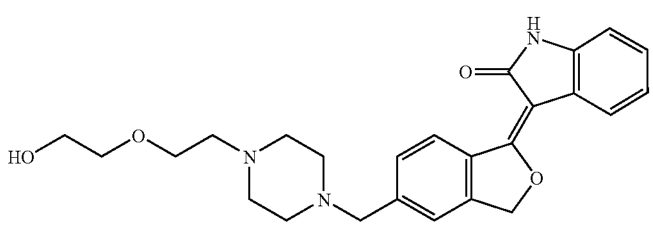 [SMILES: O=C1Nc2ccccc2/C1=C1\OCc2cc(CN3CCN(CCOCCO)CC3)ccc21] | 3-(5-{4-[2-(2-Hydroxy-ethoxy)-ethyl]-piperazin-1-ylmethyl}-3H-isobenzofuran-1-ylidene)-1,3-dihydro-indol-2-one | 435.521 |
| 220 | 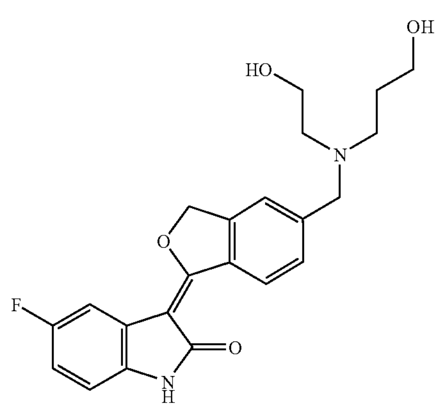 [SMILES: O=C1Nc2ccc(F)cc2/C1=C1\OCc2cc(CN(CCO)CCCO)ccc21] | 5-Fluoro-3-(5-{[(2-hydroxy-ethyl)-(3-hydroxy-propyl)-amino]-methyl}-3H-isobenzofuran-1-ylidene)-1,3-dihydro-indol-2-one | 398.432 |

TABLE 7-continued

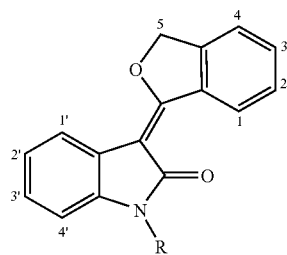

| Example Number | Chemical Structure | Chemical Name | Molecular Weight |
|---|---|---|---|
| 221 | Chiral | (S)-2-{[1-(5-Fluoro-2-oxo-1,2-dihydro-indol-3-ylidene)-1,3-dihydro-isobenzofuran-5-ylmethyl]-amino}-(R)-3-hydroxy-butyric acid methyl ester | 412.415 |
| 222 | 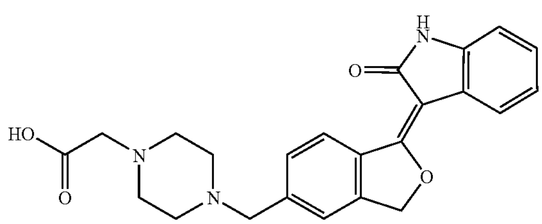 [SMILES: O=C(O)CN1CCN(Cc2ccc3c(c2)CO/C3=C2/C(=O)Nc3ccccc32)CC1] | {4-[1-(2-Oxo-1,2-dihydro-indol-3-ylidene)-1,3-dihydro-isobenzofuran-5-ylmethyl]-piperazin-1-yl}-acetic acid | 405.452 |
| 223 | 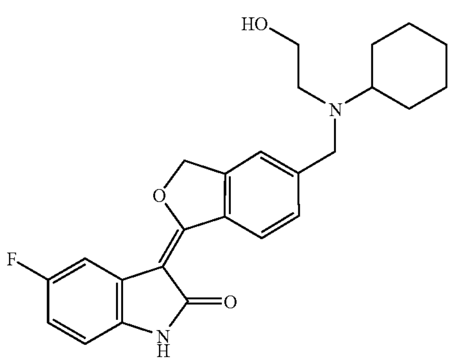 [SMILES: O=C1Nc2ccc(F)cc2/C1=C1\OCc2cc(CN(CCO)C3CCCCC3)ccc21] | 3-(5-{[Cyclohexyl-(2-hydroxy-ethyl)-amino]-methyl}-3H-isobenzofuran-1-ylidene)-5-fluoro-1,3-dihydro-indol-2-one | 422.497 |

TABLE 7-continued

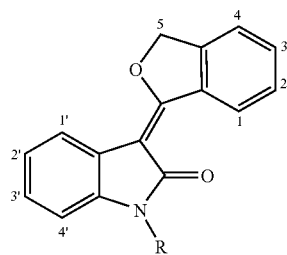

| Example Number | Chemical Structure | Chemical Name | Molecular Weight |
| --- | --- | --- | --- |
| 224 | 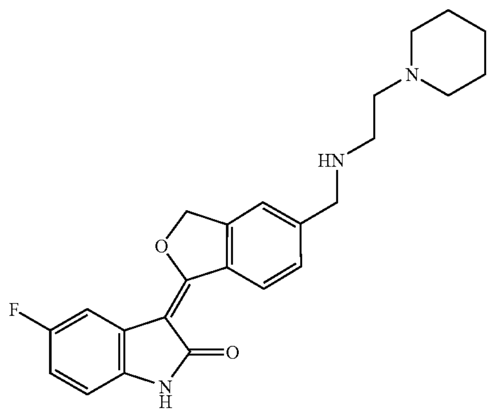 [SMILES: O=C1Nc2ccc(F)cc2/C1=C1\OCc2cc(CNCCN3CCCCC3)ccc21] | 5-Fluoro-3-{5-[(2-piperidin-1-yl-ethylamino)-methyl]-3H-isobenzofuran-1-ylidene}-1,3-dihydro-indol-2-one | 407.486 |
| 225 | 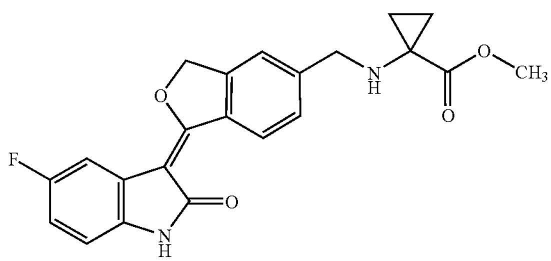 [SMILES: COC(=O)C1(NCc2ccc3c(c2)CO/C3=C2/C(=O)Nc3ccc(F)cc32)CC1] | 1-{[1-(5-Fluoro-2-oxo-1,2-dihydro-indol-3-ylidene)-1,3-dihydro-isobenzofuran-5-ylmethyl]-amino}-cyclopropanecarboxylic acid methyl ester | 394.4 |
| 226 | 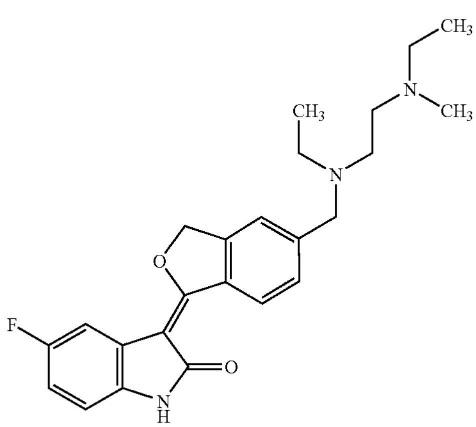 [SMILES: CCN(C)CCN(CC)Cc1ccc2c(c1)CO/C2=C1/C(=O)Nc2ccc(F)cc21] | 3-[5-({Ethyl-[2-(ethyl-methyl-amino)-ethyl]-amino}-methyl)-3H-isobenzofuran-1-ylidene]-5-fluoro-1,3-dihydro-indol-2-one | 409.502 |

TABLE 7-continued
| Example Number | Chemical Structure | Chemical Name | Molecular Weight |
|---|---|---|---|
| 227 | 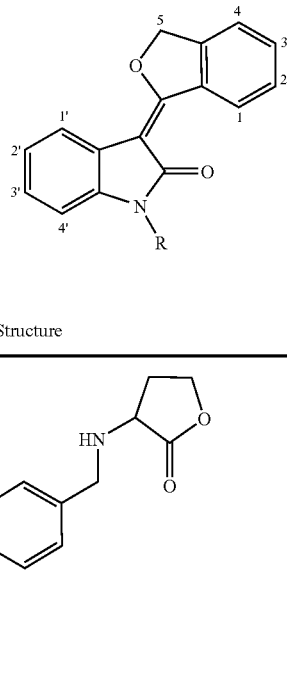 | 5-Fluoro-3-{5-[(2-oxo-tetrahydro-furan-3-ylamino)-methyl]-3H-isobenzofuran-1-ylidene}-1,3-dihydro-indol-2-one | 380.373 |
| 228 | 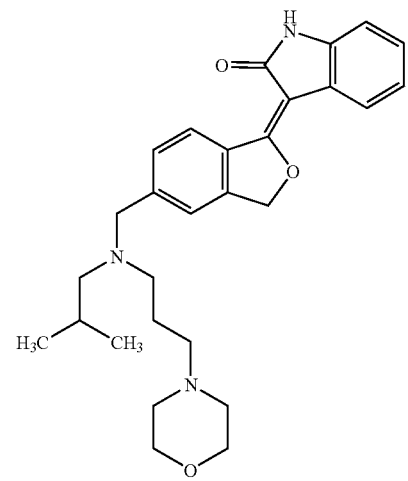 [SMILES: CC(C)CN(CCCN1CCOCC1)Cc1ccc2c(c1)CO/C2=C1/C(=O)Nc2ccccc21] | 3-(5-{[Isobutyl-(3-morpholin-4-yl-propyl)-amino]-methyl}-3H-isobenzofuran-1-ylidene)-1,3-dihydro-indol-2-one | 461.603 |
| 229 | 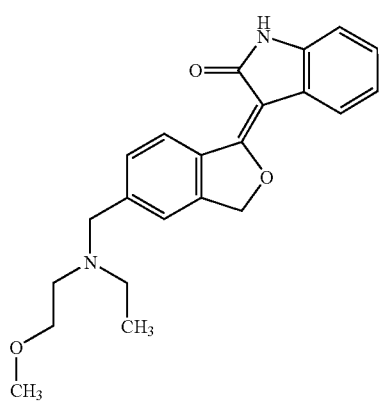 [SMILES: CCN(CCOC)Cc1ccc2c(c1)CO/C2=C1/C(=O)Nc2ccccc21] | 3-(5-{[Ethyl-(2-methoxy-ethyl)-amino]-methyl}-3H-isobenzofuran-1-ylidene)-1,3-dihydro-indol-2-one | 364.443 |

TABLE 7-continued

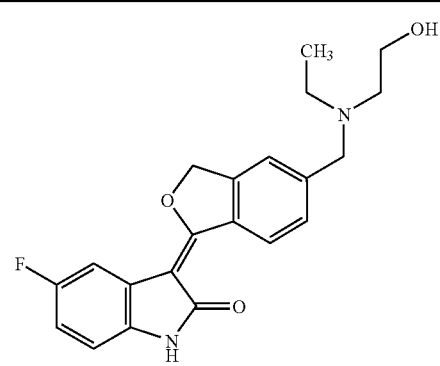

| Example Number | Chemical Structure | Chemical Name | Molecular Weight |
|---|---|---|---|
| 230 | 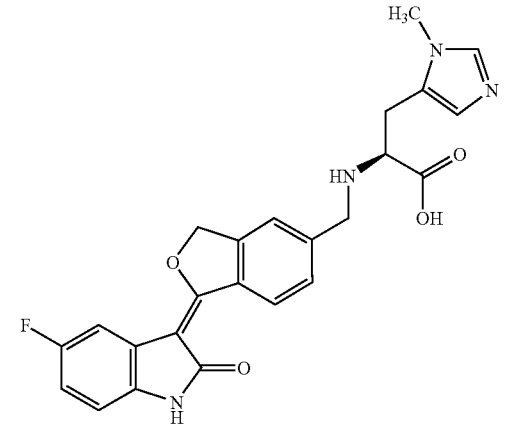 [SMILES: Cn1cncc1C[C@H](NCc1ccc2c(c1)CO/C2=C1/C(=O)Nc2ccc(F)cc21)C(=O)O] | 3-(5-{[Ethyl-(2-hydroxy-ethyl)-amino]-methyl}-3H-isobenzofuran-1-ylidene)-5-fluoro-1,3-dihydro-indol-2-one | 368.406 |
| 231 | 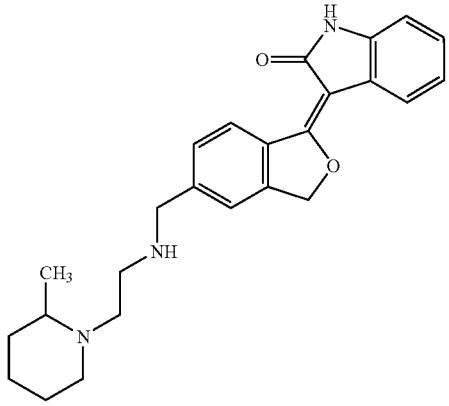 | (S)-2-{[1-{5-Fluoro-2-oxo-1,2-dihydro-indol-3-ylidene}-1,3-dihydro-isobenzofuran-5-ylmethyl]-amino}-3-(3-methyl-3H-imidazol-4-yl)-propionic acid | 448.452 |
| 232 | 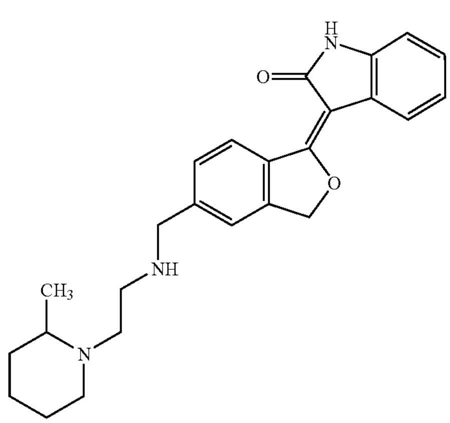 [SMILES: CC1CCCCN1CCNCc1ccc2c(c1)CO/C2=C1/C(=O)Nc2ccccc21] | 3-(5-{[2-(2-Methyl-piperidin-1-yl)-ethylamino]-methyl}-3H-isobenzofuran-1-ylidene)-1,3-dihydro-indol-2-one | 403.523 |

TABLE 7-continued
| Example Number | Chemical Structure | Chemical Name | Molecular Weight |
|---|---|---|---|
| 233 | 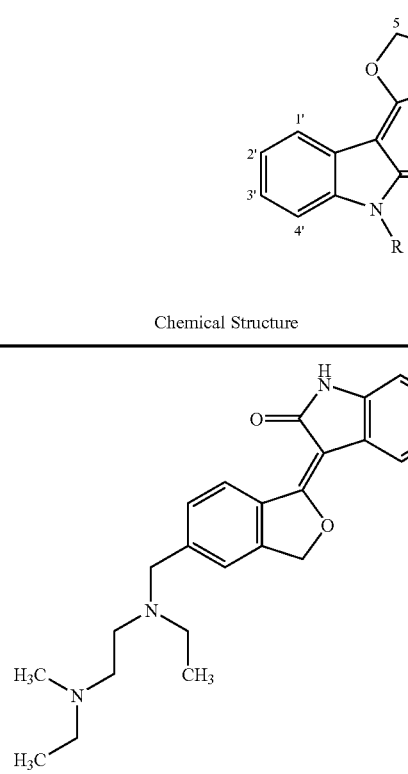 | 3-[5-({Ethyl-[2-(ethyl-methyl-amino)-ethyl]-amino}-methyl)-3H-isobenzofuran-1-ylidene]-1,3-dihydro-indol-2-one | 391.512 |
| 234 | 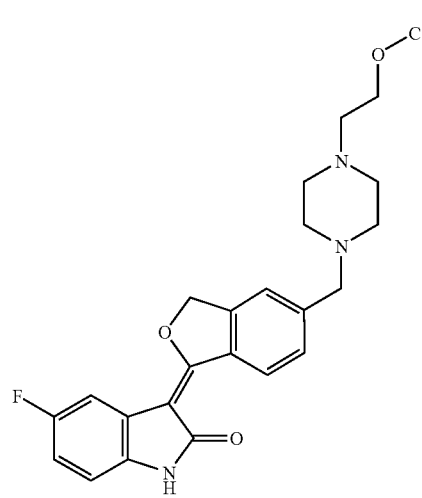 | 5-Fluoro-3-{5-[4-(2-methoxy-ethyl)-piperazin-1-ylmethyl]-3H-isobenzofuran-1-ylidene}-1,3-dihydro-indol-2-one | 423.485 |
| 235 | 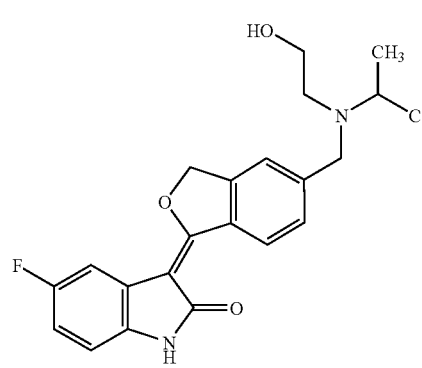 | 5-Fluoro-3-(5-{[(2-hydroxy-ethyl)-isopropyl-amino]-methyl}-3H-isobenzofuran-1-ylidene)-1,3-dihydro-indol-2-one | 382.433 |

TABLE 7-continued

| Example Number | Chemical Structure | Chemical Name | Molecular Weight |
|---|---|---|---|
| 236 | Chiral | 5-(N',N'-Dimethyl-guanidino)-(S)-2-{[1-(2-oxo-1,2-dihydro-indol-3-ylidene)-1,3-dihydro-isobenzofuran-5-ylmethyl]-amino}-pentanoic acid | 463.535 |
| 237 | 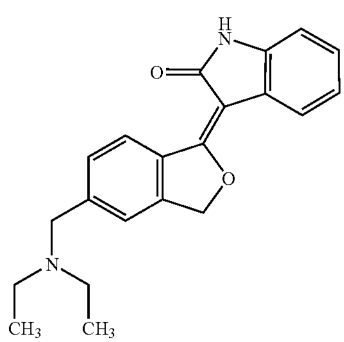 [SMILES: CCN(CC)Cc1ccc2c(c1)CO/C2=C1/C(=O)Nc2ccccc21] | 3-(5-Diethylaminomethyl-3H-isobenzofuran-1-ylidene)-1,3-dihydro-indol-2-one | 334.417 |
| 238 | 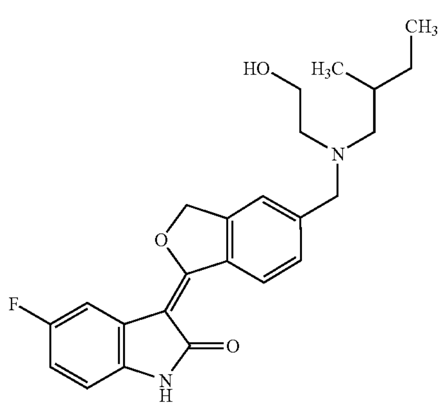 [SMILES: CCC(C)CN(CCO)Cc1ccc2c(c1)CO/C2=C1/C(=O)Nc2ccc(F)cc21] | 5-Fluoro-3-(5-{[(2-hydroxy-ethyl)-(2-methyl-butyl)-amino]-methyl}-3H-isobenzofuran-1-ylidene)-1,3-dihydro-indol-2-one | 410.486 |

TABLE 7-continued

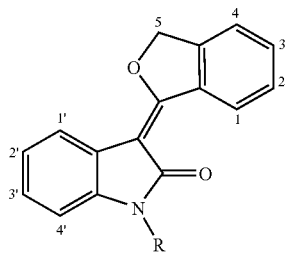

| Example Number | Chemical Structure | Chemical Name | Molecular Weight |
|---|---|---|---|
| 239 | 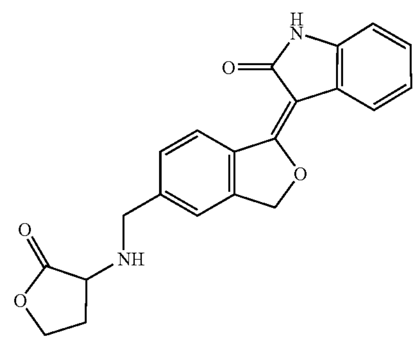 [SMILES: O=C1Nc2ccccc2/C1=C1\OCc2cc(CNC3CCOC3=O)ccc21] | 3-{5-[(2-Oxo-tetrahydro-furan-3-ylamino)-methyl]-3H-isobenzofuran-1-ylidene}-1,3-dihydro-indol-2-one | 362.383 |
| 240 | Chiral | 3-(5-{[((2S)-2,3-Dihydroxy-propyl)-isopropyl-amino]-methyl}-3H-isobenzofuran-1-ylidene)-5-fluoro-1,3-dihydro-indol-2-one | 412.458 |
| 241 | 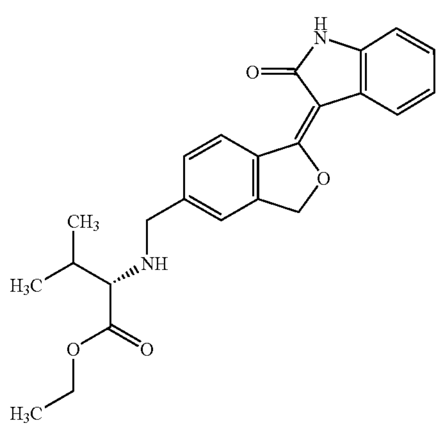 [SMILES: CCOC(=O)[C@@H](NCc1ccc2c(c1)CO/C2=C1/C(=O)Nc2ccccc21)C(C)C] | 3-Methyl-(S)-2-{[1-(2-oxo-1,2-dihydro-indol-3-ylidene)-1,3-dihydro-isobenzofuran-5-ylmethyl]-amino}-butyric acid ethyl ester | 406.479 |

TABLE 7-continued

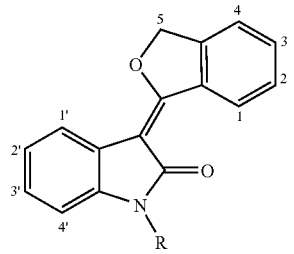

| Example Number | Chemical Structure | Chemical Name | Molecular Weight |
|---|---|---|---|
| 242 | 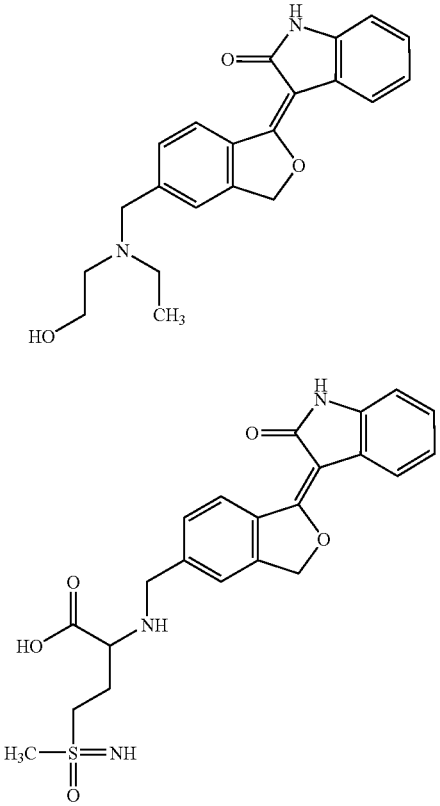 | 3-(5-{[Ethyl-(2-hydroxy-ethyl)-amino]-methyl}-3H-isobenzofuran-1-ylidene)-1,3-dihydro-indol-2-one | 350.416 |
| 243 | 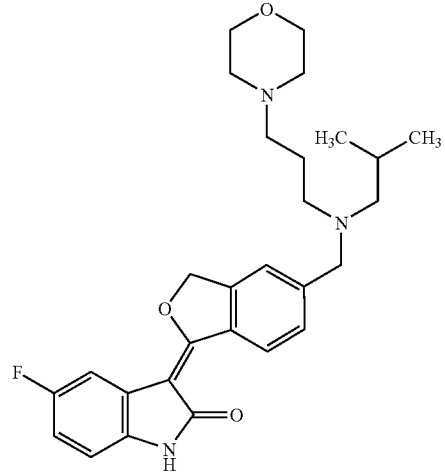 | 4-Methylsulfonimidosyl-2-{[1-(2-oxo-1,2-dihydro-indol-3-ylidene)-1,3-dihydro-isobenzofuran-5-ylmethyl]-amino}-butanoic acid | 441.506 |
| 244 | 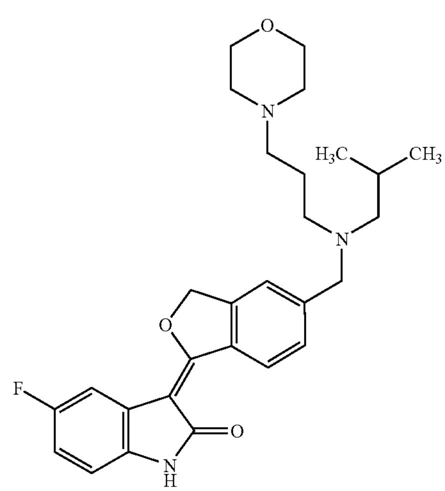 [SMILES: CC(C)CN(CCCN1CCOCC1)Cc1ccc2c(c1)CO/C2=C1/C(=O)Nc2ccc(F)cc21] | 5-Fluoro-3-(5-{[isobutyl-(3-morpholin-4-yl-propyl)-amino]-methyl}-3H-isobenzofuran-1-ylidene)-1,3-dihydro-indol-2-one | 479.593 |

TABLE 7-continued

| Example Number | Chemical Structure | Chemical Name | Molecular Weight |
|---|---|---|---|
| 245 | 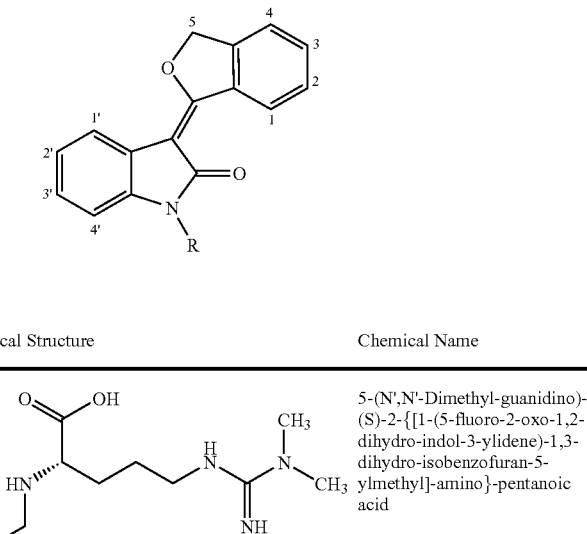 | 5-(N',N'-Dimethyl-guanidino)-(S)-2-{[1-(5-fluoro-2-oxo-1,2-dihydro-indol-3-ylidene)-1,3-dihydro-isobenzofuran-5-ylmethyl]-amino}-pentanoic acid | 481.525 |
| 246 | 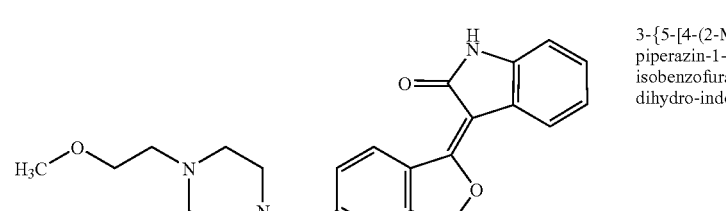 | 3-{5-[4-(2-Methoxy-ethyl)-piperazin-1-ylmethyl]-3H-isobenzofuran-1-ylidene}-1,3-dihydro-indol-2-one | 405.495 |
| 247 | 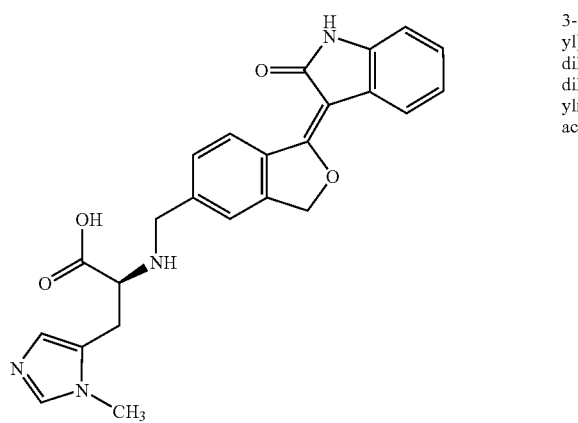 | 3-(3-Methyl-3H-imidazol-4-yl)-(S)-2-{[1-(2-oxo-1,2-dihydro-indol-3-ylidene)-1,3-dihydro-isobenzofuran-5-ylmethyl]-amino}-propionic acid | 430.462 |

TABLE 7-continued

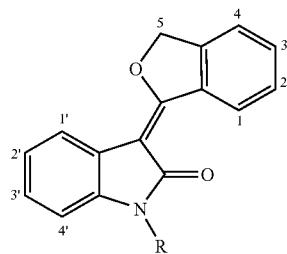

| Example Number | Chemical Structure | Chemical Name | Molecular Weight |
|---|---|---|---|
| 248 | 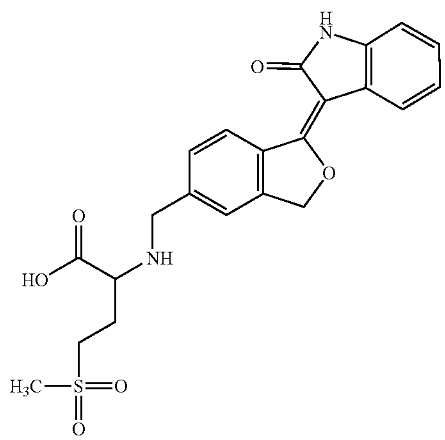 [SMILES: CS(=O)(=O)CCC(NCc1ccc2c(c1)CO/C2=C1/C(=O)Nc2ccccc21)C(=O)O] | 4-Methanesulfonyl-2-{[1-(2-oxo-1,2-dihydro-indol-3-ylidene)-1,3-dihydro-isobenzofuran-5-ylmethyl]-amino}-butyric acid | 442.49 |
| 249 | 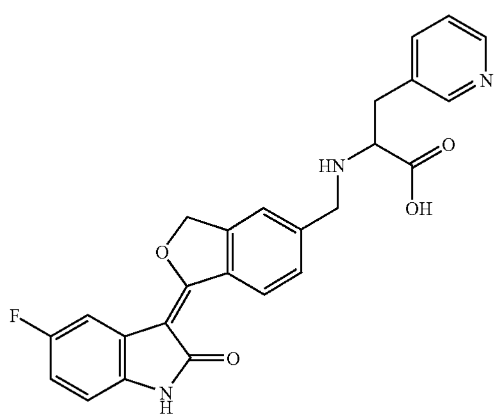 [SMILES: O=C1Nc2ccc(F)cc2/C1=C1\OCc2cc(CNC(Cc3cccnc3)C(=O)O)ccc21] | 2-{[1-(5-Fluoro-2-oxo-1,2-dihydro-indol-3-ylidene)-1,3-dihydro-isobenzofuran-5-ylmethyl]-amino}-3-pyridin-3-yl-propionic acid | 445.448 |
| 250 | 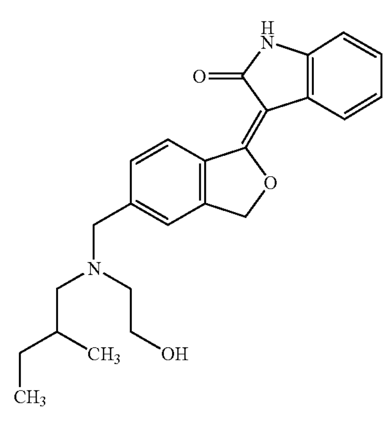 [SMILES: CCC(C)CN(CCO)Cc1ccc2c(c1)CO/C2=C1/C(=O)Nc2ccccc21] | 3-(5-{[(2-Hydroxy-ethyl)-(2-methyl-butyl)-amino]-methyl}-3H-isobenzofuran-1-ylidene)-1,3-dihydro-indol-2-one | 392.496 |

TABLE 7-continued

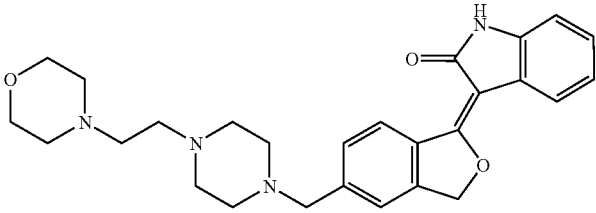 [SMILES: O=C1Nc2ccccc2/C1=C1\OCc2cc(CN3CCN(CCN4CCOCC4)CC3)ccc21]

| Example Number | Chemical Structure | Chemical Name | Molecular Weight |
|---|---|---|---|
| 251 | 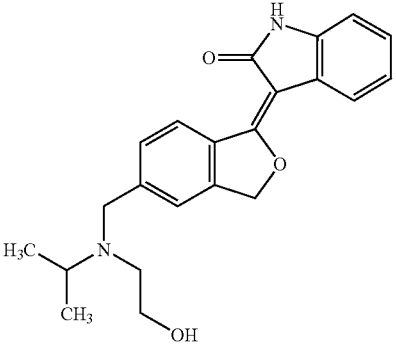 [SMILES: CC(C)N(CCO)Cc1ccc2c(c1)CO/C2=C1/C(=O)Nc2ccccc21] | 3-{5-[4-(2-Morpholin-4-yl-ethyl)-piperazin-1-ylmethyl]-3H-isobenzofuran-1-ylidene}-1,3-dihydro-indol-2-one | 460.575 |
| 252 | 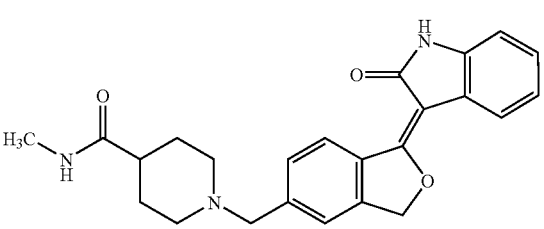 [SMILES: CNC(=O)C1CCN(Cc2ccc3c(c2)CO/C3=C2/C(=O)Nc3ccccc32)CC1] | 3-(5-{[(2-Hydroxy-ethyl)-isopropyl-amino]-methyl}-3H-isobenzofuran-1-ylidene)-1,3-dihydro-indol-2-one | 364.443 |
| 253 | 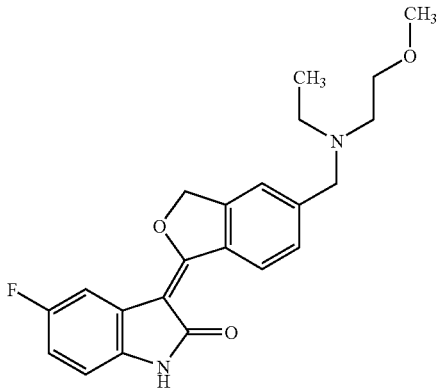 | 1-[1-(2-Oxo-1,2-dihydro-indol-3-ylidene)-1,3-dihydro-isobenzofuran-5-ylmethyl]-piperidine-4-carboxylic acid methylamide | 403.479 |
| 254 | 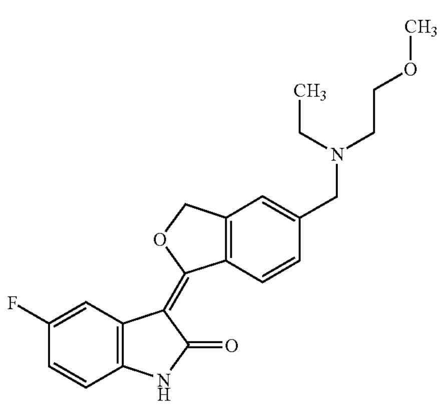 [SMILES: CCN(CCOC)Cc1ccc2c(c1)CO/C2=C1/C(=O)Nc2ccc(F)cc21] | 3-(5-{[Ethyl-(2-methoxy-ethyl)-amino]-methyl}-3H-isobenzofuran-1-ylidene)-5-fluoro-1,3-dihydro-indol-2-one | 382.433 |

TABLE 7-continued

| Example Number | Chemical Structure | Chemical Name | Molecular Weight |
|---|---|---|---|
| 255 | 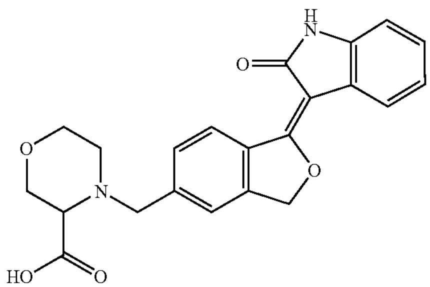 [SMILES: O=C1Nc2ccccc2/C1=C1\OCc2cc(CN3CCOCC3C(=O)O)ccc21] | 4-[1-(2-Oxo-1,2-dihydro-indol-3-ylidene)-1,3-dihydro-isobenzofuran-5-ylmethyl]-morpholine-3-carboxylic acid | 392.409 |
| 256 | Chiral | 3-(5-{[((2R)-2,3-Dihydroxy-propyl)-isopropyl-amino]-methyl}-3H-isobenzofuran-1-ylidene)-1,3-dihydro-indol-2-one | 394.468 |
| 257 | 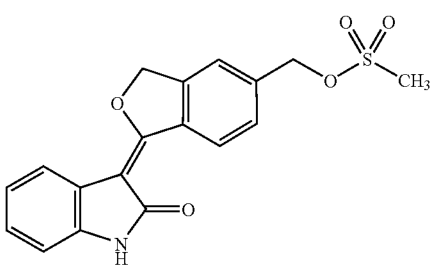 [SMILES: CS(=O)(=O)OCc1ccc2c(c1)CO/C2=C1/C(=O)Nc2ccccc21] | Methanesulfonic acid 1-(2-oxo-1,2-dihydro-indol-3-ylidene)-1,3-dihydro-isobenzofuran-5-ylmethyl ester | 357.384 |
| 258 | 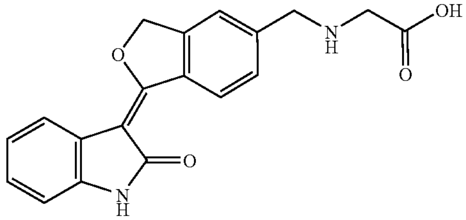 [SMILES: O=C(O)CNCc1ccc2c(c1)CO/C2=C1/C(=O)Nc2ccccc21] | {[1-(2-Oxo-1,2-dihydro-indol-3-ylidene)-1,3-dihydro-isobenzofuran-5-ylmethyl]-amino}-acetic acid | 336.345 |

TABLE 7-continued

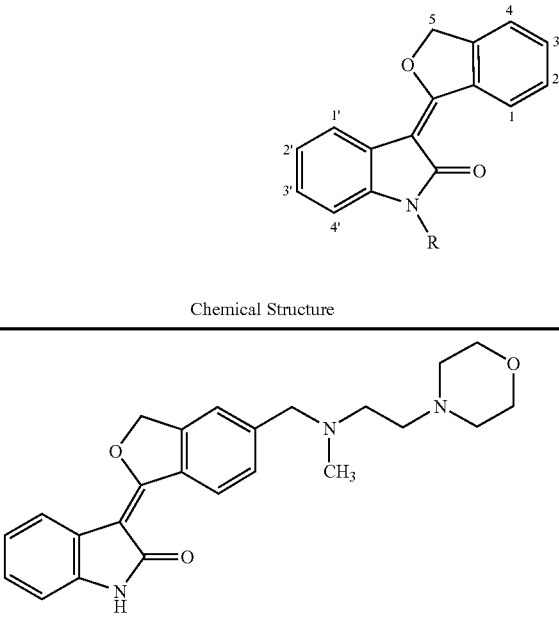

| Example Number | Chemical Structure | Chemical Name | Molecular Weight |
|---|---|---|---|
| 259 | 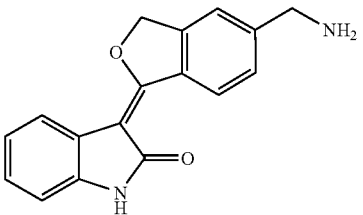 [SMILES: NCc1ccc2c(c1)CO/C2=C1/C(=O)Nc2ccccc21] | 3-(5-{[Methyl-(2-morpholin-4-yl-ethyl)-amino]-methyl}-3H-isobenzofuran-1-ylidene)-1,3-dihydro-indol-2-one | 405.495 |
| 260 | 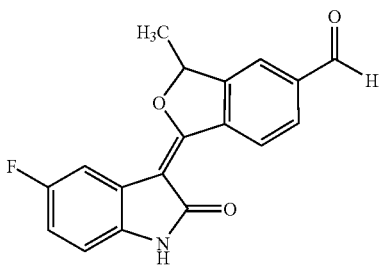 [SMILES: CC1O/C(=C2/C(=O)Nc3ccc(F)cc32)c2ccc(C=O)cc21] | 3-(5-Aminomethyl-3H-isobenzofuran-1-ylidene)-1,3-dihydro-indol-2-one | 278.31 |
| 261 | 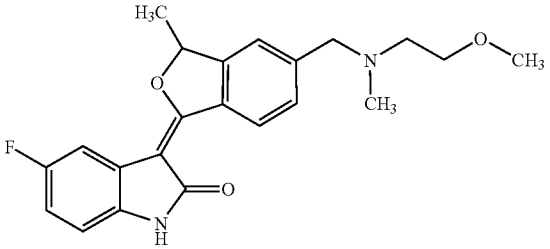 [SMILES: COCCN(C)Cc1ccc2c(c1)C(C)O/C2=C1/C(=O)Nc2ccc(F)cc21] | 1-(5-Fluoro-2-oxo-1,2-dihydro-indol-3-ylidene)-3-methyl-1,3-dihydro-isobenzofuran-5-carbaldehyde | 309.295 |
| 262 | 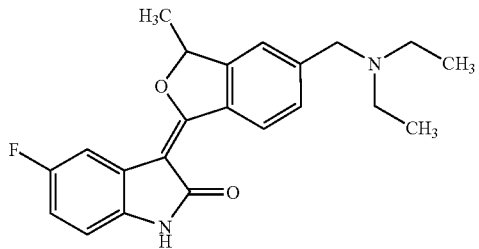 | 5-Fluoro-3-(5-{[(2-methoxy-ethyl)-methyl-amino]-methyl}-3-methyl-3H-isobenzofuran-1-ylidene)-1,3-dihydro-indol-2-one | 382.433 |
| 263 | 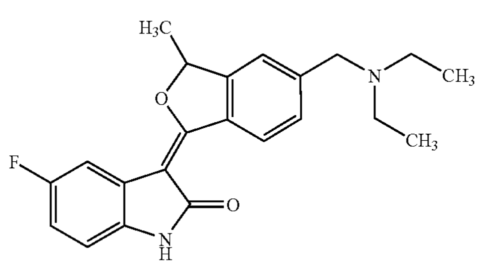 [SMILES: CCN(CC)Cc1ccc2c(c1)C(C)O/C2=C1/C(=O)Nc2ccc(F)cc21] | 3-(5-Diethylaminomethyl-3-methyl-3H-isobenzofuran-1-ylidene)-5-fluoro-1,3-dihydro-indol-2-one | 366.434 |

TABLE 7-continued

| Example Number | Chemical Structure | Chemical Name | Molecular Weight |
|---|---|---|---|
| 264 | 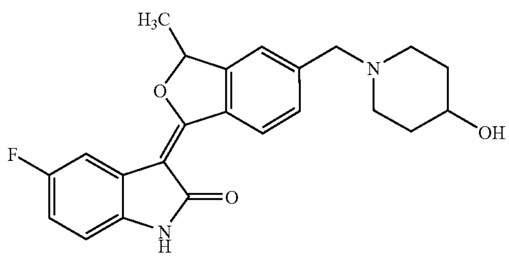 [SMILES: CC1O/C(=C2/C(=O)Nc3ccc(F)cc32)c2ccc(CN3CCC(O)CC3)cc21] | 5-Fluoro-3-[5-(4-hydroxy-piperidin-1-ylmethyl)-3-methyl-3H-isobenzofuran-1-ylidene]-1,3-dihydro-indol-2-one | 394.444 |
| 265 | 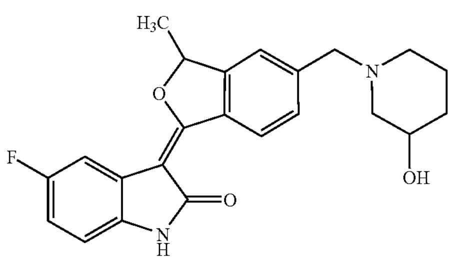 [SMILES: CC1O/C(=C2/C(=O)Nc3ccc(F)cc32)c2ccc(CN3CCCC(O)C3)cc21] | 5-Fluoro-3-[5-(3-hydroxy-piperidin-1-ylmethyl)-3-methyl-3H-isobenzofuran-1-ylidene]-1,3-dihydro-indol-2-one | 394.444 |
| 266 | 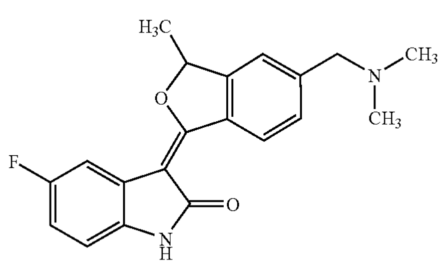 [SMILES: CC1O/C(=C2/C(=O)Nc3ccc(F)cc32)c2ccc(CN(C)C)cc21] | 3-(5-Dimethylaminomethyl-3-methyl-3H-isobenzofuran-1-ylidene)-5-fluoro-1,3-dihydro-indol-2-one | 338.38 |
| 267 | 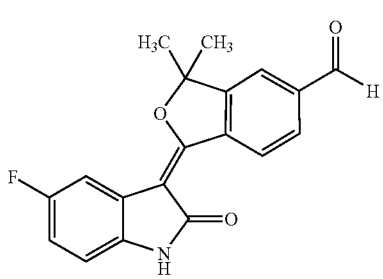 [SMILES: CC1(C)O/C(=C2/C(=O)Nc3ccc(F)cc32)c2ccc(C=O)cc21] | 1-(5-Fluoro-2-oxo-1,2-dihydro-indol-3-ylidene)-3,3-dimethyl-1,3-dihydro-isobenzofuran-5-carbaldehyde | 323.322 |

TABLE 7-continued

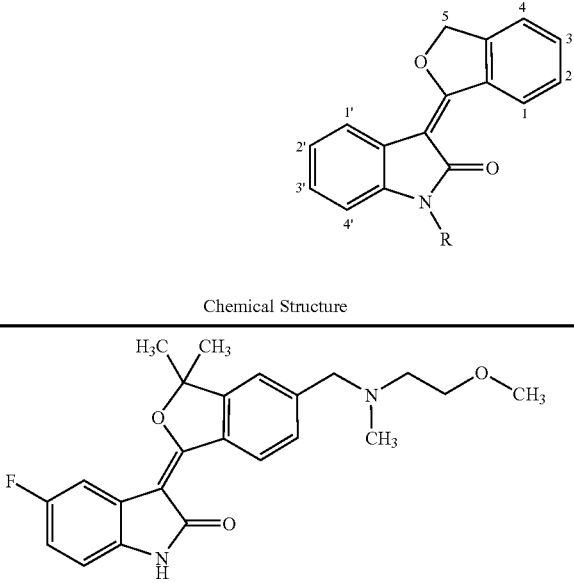

| Example Number | Chemical Structure | Chemical Name | Molecular Weight |
|---|---|---|---|
| 268 | 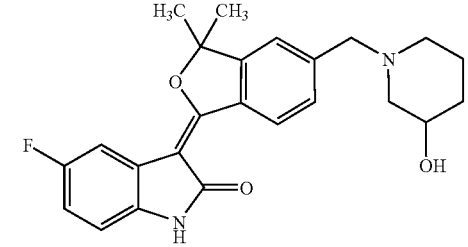 [SMILES: CC1(C)O/C(=C2/C(=O)Nc3ccc(F)cc32)c2ccc(CN3CCCC(O)C3)cc21] | 5-Fluoro-3-(5-{[(2-methoxy-ethyl)-methyl-amino]-methyl}-3,3-dimethyl-3H-isobenzofuran-1-ylidene)-1,3-dihydro-indol-2-one | 396.46 |
| 269 | 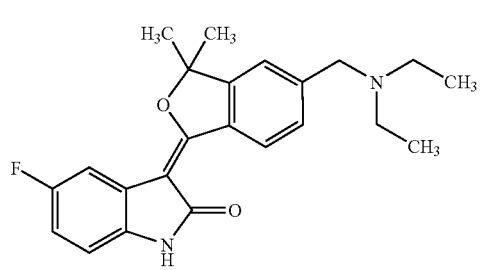 [SMILES: CCN(CC)Cc1ccc2c(c1)C(C)(C)O/C2=C1/C(=O)Nc2ccc(F)cc21] | 5-Fluoro-3-[5-(3-hydroxy-piperidin-1-ylmethyl)-3,3-dimethyl-3H-isobenzofuran-1-ylidene]-1,3-dihydro-indol-2-one | 408.47 |
| 270 | 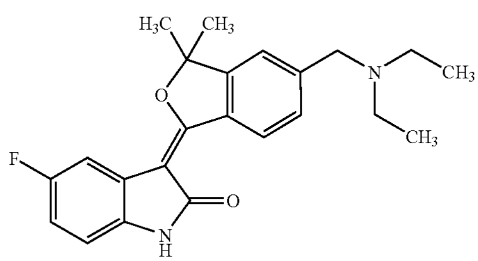 | 3-(5-Diethylaminomethyl-3,3-dimethyl-3H-isobenzofuran-1-ylidene)-5-fluoro-1,3-dihydro-indol-2-one | 380.461 |
| 271 | 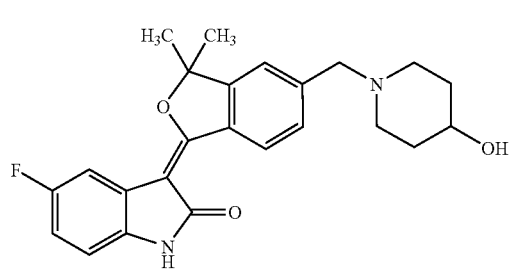 [SMILES: CC1(C)O/C(=C2/C(=O)Nc3ccc(F)cc32)c2ccc(CN3CCC(O)CC3)cc21] | 5-Fluoro-3-[5-(4-hydroxy-piperidin-1-ylmethyl)-3,3-dimethyl-3H-isobenzofuran-1-ylidene]-1,3-dihydro-indol-2-one | 408.47 |

TABLE 7-continued
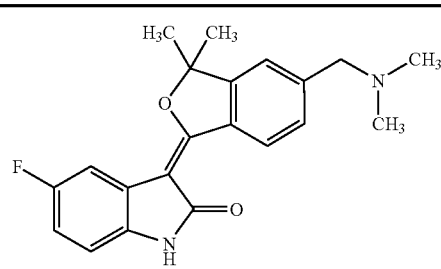
| Example Number | Chemical Structure | Chemical Name | Molecular Weight |
|---|---|---|---|
| 272 | 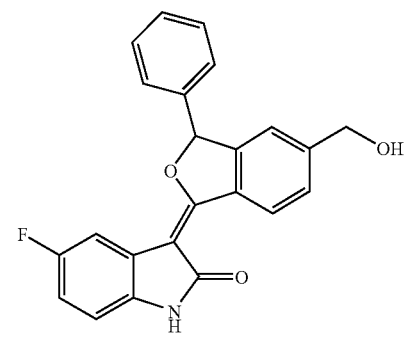 | 3-(5-Dimethylaminomethyl-3,3-dimethyl-3H-isobenzofuran-1-ylidene)-5-fluoro-1,3-dihydro-indol-2-one | 352.407 |
| 273 | 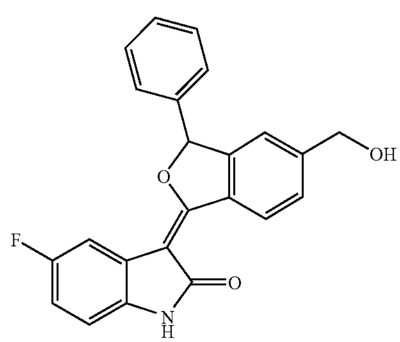 [SMILES: O=C1Nc2ccc(F)cc2/C1=C1\OC(c2ccccc2)c2cc(CO)ccc21] | 5-Fluoro-3-(5-hydroxymethyl-3-phenyl-3H-isobenzofuran-1-ylidene)-1,3-dihydro-indol-2-one | 373.381 |
| 274 | 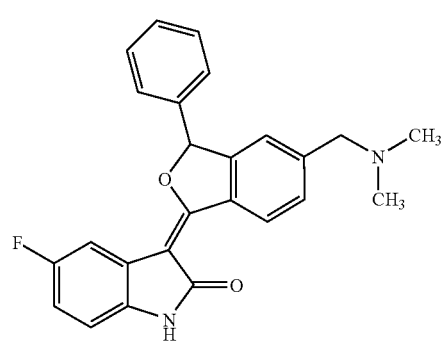 [SMILES: CN(C)Cc1ccc2c(c1)C(c1ccccc1)O/C2=C1/C(=O)Nc2ccc(F)cc21] | 3-(5-Dimethylaminomethyl-3-phenyl-3H-isobenzofuran-1-ylidene)-5-fluoro-1,3-dihydro-indol-2-one | 400.451 |

TABLE 8

| Example Number | Chemical Structure | Chemical Name | Molecular Weight |
|---|---|---|---|
| 275 | 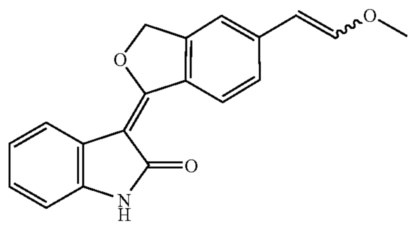 [SMILES: COC=Cc1ccc2c(c1)CO/C2=C1/C(=O)Nc2ccccc21] | 3-[5-(2-Methoxy-vinyl)-3H-isobenzofuran-1-ylidene]-1,3-dihydro-indol-2-one | 305.332 |
| 276 | 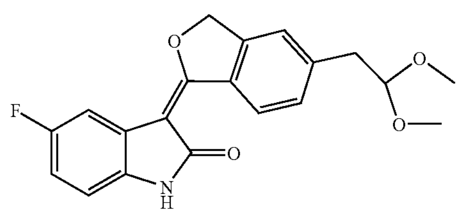 [SMILES: COC(Cc1ccc2c(c1)CO/C2=C1/C(=O)Nc2ccc(F)cc21)OC] | 3-[5-(2,2-Dimethoxy-ethyl)-3H-isobenzofuran-1-ylidene]-1,3-dihydro-indol-2-one | 337.373 |
| 277 | 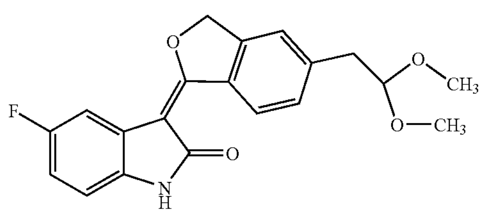 [SMILES: COC(Cc1ccc2c(c1)CO/C2=C1/C(=O)Nc2ccc(F)cc21)OC] | 3-[5-(2,2-Dimethoxy-ethyl)-3H-isobenzofuran-1-ylidene]-5-fluoro-1,3-dihydro-indol-2-one | 355.363 |
| 278 | 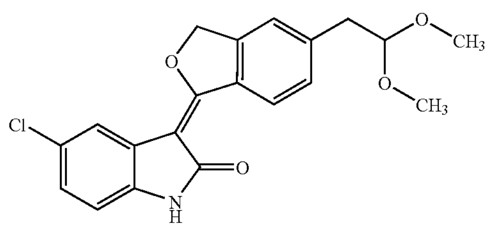 [SMILES: COC(Cc1ccc2c(c1)CO/C2=C1/C(=O)Nc2ccc(Cl)cc21)OC] | 5-Chloro-3-[5-(2,2-dimethoxy-ethyl)-3H-isobenzofuran-1-ylidene]-1,3-dihydro-indol-2-one | 371.818 |
| 279 | 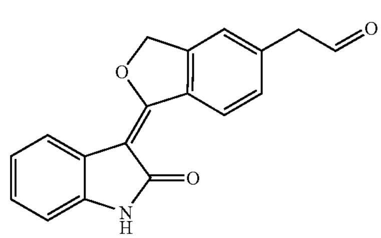 [SMILES: O=CCc1ccc2c(c1)CO/C2=C1/C(=O)Nc2ccccc21] | [1-(2-Oxo-1,2-dihydro-indol-3-ylidene)-1,3-dihydro-isobenzofuran-5-yl]-acetaldehyde | 291.305 |

TABLE 8-continued
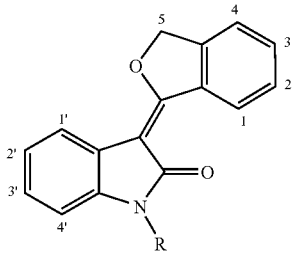
| 280 | 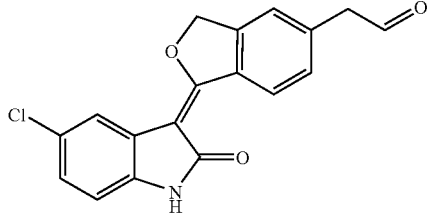 [SMILES: O=CCc1ccc2c(c1)CO/C2=C1/C(=O)Nc2ccc(Cl)cc21] | [1-(5-Chloro-2-oxo-1,2-dihydro-indol-3-ylidene)-1,3-dihydro-isobenzofuran-5-yl]-acetaldehyde | 325.75 |
| --- | --- | --- | --- |
| 281 | 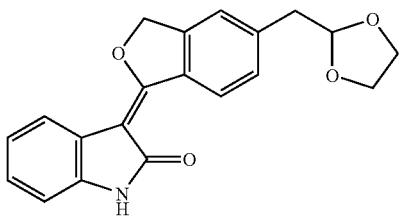 [SMILES: O=C1Nc2ccccc2/C1=C1\OCc2cc(CC3OCCO3)ccc21] | 3-(5-[1,3]Dioxolan-2-ylmethyl-3H-isobenzofuran-1-ylidene)-1,3-dihydro-indol-2-one | 335.357 |
| 282 | 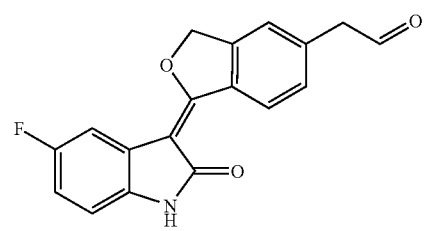 [SMILES: O=CCc1ccc2c(c1)CO/C2=C1/C(=O)Nc2ccc(F)cc21] | [1-(5-Fluoro-2-oxo-1,2-dihydro-indol-3-ylidene)-1,3-dihydro-isobenzofuran-5-yl]-acetaldehyde | 309.295 |
| 283 | 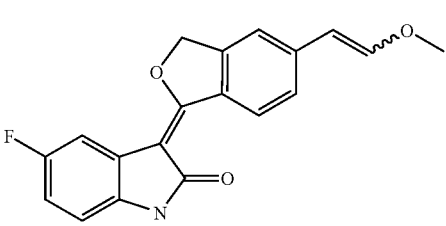 [SMILES: COC=Cc1ccc2c(c1)CO/C2=C1/C(=O)Nc2ccc(F)cc21] | 5-Fluoro-3-[5-(2-methoxy-vinyl)-3H-isobenzofuran-1-ylidene]-1,3-dihydro-indol-2-one | 323.322 |
| 284 | 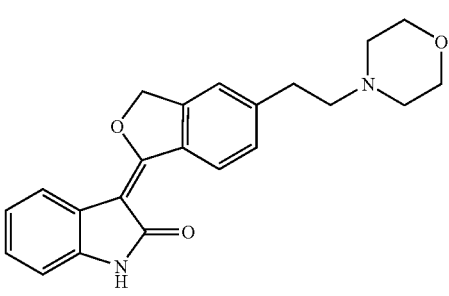 [SMILES: O=C1Nc2ccccc2/C1=C1\OCc2cc(CCN3CCOCC3)ccc21] | 3-[5-(2-Morpholin-4-yl-ethyl)-3H-isobenzofuran-1-ylidene]-1,3-dihydro-indol-2-one | 362.427 |

TABLE 8-continued
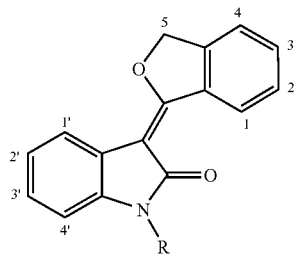
| Example Number | Chemical Structure | Chemical Name | Molecular Weight | Table Number |
|---|---|---|---|---|
| 292 | 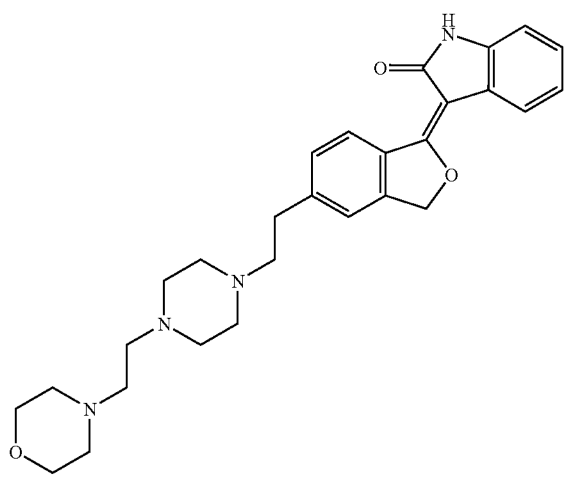 [SMILES: O=C1Nc2ccccc2/C1=C1\OCc2cc(CCN3CCN(CCN4CCOCC4)CC3)ccc21] | 3-(5-{2-[4-(2-Morpholin-4-yl-ethyl)-piperazin-1-yl]-ethyl}-3H-isobenzofuran-1-ylidene)-1,3-dihydro-indol-2-one | 474.59 | 8 |
| 293 | 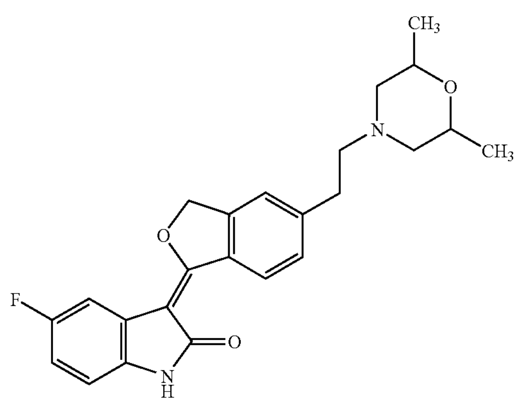 [SMILES: CC1CN(CCc2ccc3c(c2)CO/C3=C2/C(=O)Nc3ccc(F)cc32)CC(C)O1] | 3-{5-[2-(2,6-Dimethyl-morpholin-4-yl)-ethyl]-3H-isobenzofuran-1-ylidene}-5-fluoro-1,3-dihydro-indol-2-one | 408.47 | 8 |
| 294 | 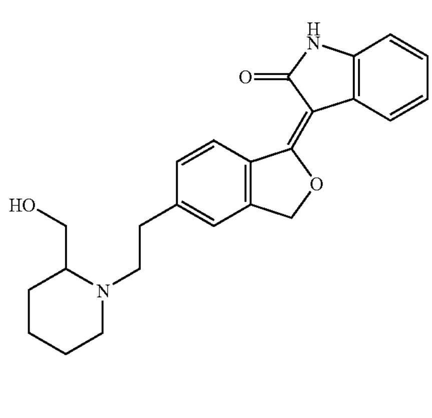 [SMILES: O=C1Nc2ccccc2/C1=C1\OCc2cc(CCN3CCCCC3CO)ccc21] | 3-{5-[2-(2-Hydroxymethyl-piperidin-1-yl)-ethyl]-3H-isobenzofuran-1-ylidene}-1,3-dihydro-indol-2-one | 390.48 | 8 |

TABLE 8-continued
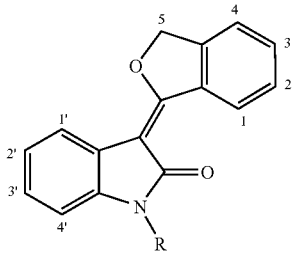
| | | | | |
|---|---|---|---|---|
| 295 | 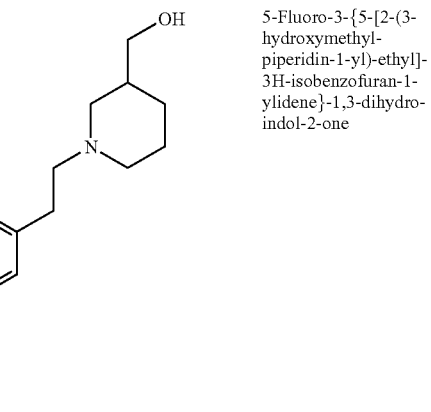 | 5-Fluoro-3-{5-[2-(3-hydroxymethyl-piperidin-1-yl)-ethyl]-3H-isobenzofuran-1-ylidene}-1,3-dihydro-indol-2-one | 408.47 | 8 |
| 296 | 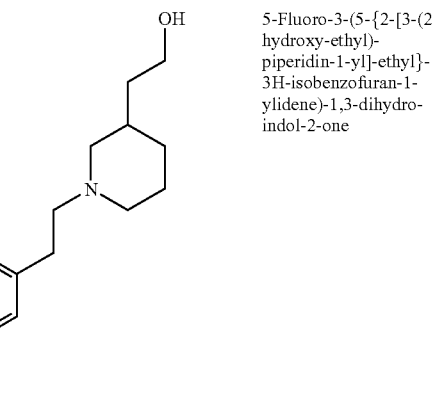 | 5-Fluoro-3-(5-{2-[3-(2-hydroxy-ethyl)-piperidin-1-yl]-ethyl}-3H-isobenzofuran-1-ylidene)-1,3-dihydro-indol-2-one | 422.497 | 8 |
| 297 | 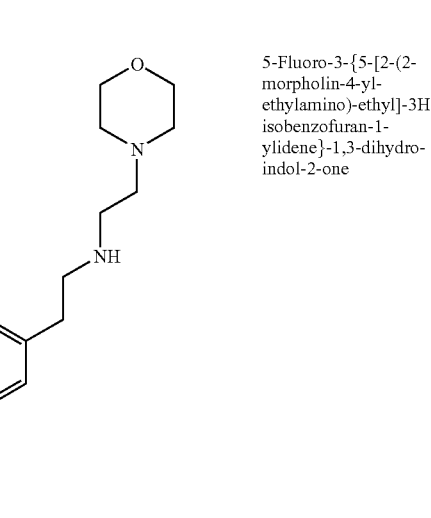 | 5-Fluoro-3-{5-[2-(2-morpholin-4-yl-ethylamino)-ethyl]-3H-isobenzofuran-1-ylidene}-1,3-dihydro-indol-2-one | 423.485 | 8 |

TABLE 8-continued
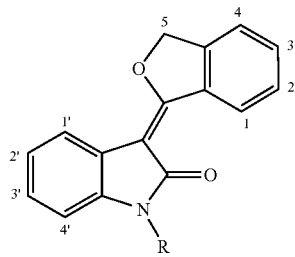
| | | | | |
|---|---|---|---|---|
| 298 | 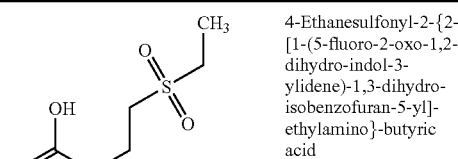 | 4-Ethanesulfonyl-2-{2-[1-(5-fluoro-2-oxo-1,2-dihydro-indol-3-ylidene)-1,3-dihydro-isobenzofuran-5-yl]-ethylamino}-butyric acid | 488.534 | 8 |
| 299 | 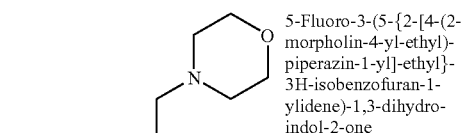<br />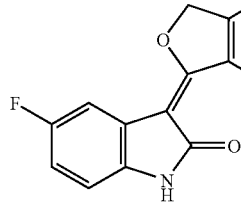 | 5-Fluoro-3-(5-{2-[4-(2-morpholin-4-yl-ethyl)-piperazin-1-yl]-ethyl}-3H-isobenzofuran-1-ylidene)-1,3-dihydro-indol-2-one | 492.592 | 8 |
| 300 | 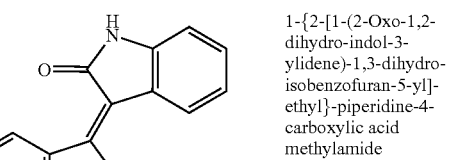<br />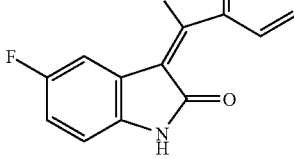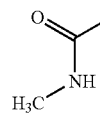 | 1-{2-[1-(2-Oxo-1,2-dihydro-indol-3-ylidene)-1,3-dihydro-isobenzofuran-5-yl]-ethyl}-piperidine-4-carboxylic acid methylamide | 417.506 | 8 |

TABLE 8-continued
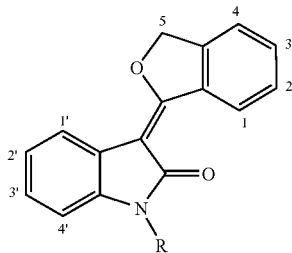
| 301 | | 5-Fluoro-3-{5-[2-(2-hydroxymethyl-morpholin-4-yl)-ethyl]-3H-isobenzofuran-1-ylidene}-1,3-dihydro-indol-2-one | 410.443 | 8 |
|---|---|---|---|---|
| 302 | | 1-{2-[1-(2-Oxo-1,2-dihydro-indol-3-ylidene)-1,3-dihydro-isobenzofuran-5-yl]-ethyl}-piperidine-3-carboxylic acid diethylamide | 459.587 | 8 |
| 303 | | 5-Fluoro-3-{5-[2-(4-hydroxy-piperidin-1-yl)-ethyl]-3H-isobenzofuran-1-ylidene}-1,3-dihydro-indol-2-one | 394.444 | 8 |

TABLE 8-continued
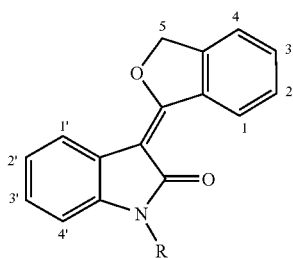
| 304 | 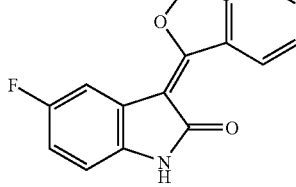 | (1-{2-[1-(5-Fluoro-2-oxo-1,2-dihydro-indol-3-ylidene)-1,3-dihydro-isobenzofuran-5-yl]-ethyl}-piperidin-3-ylmethyl)-carbamic acid tert-butyl ester | 507.603 | 8 |
|---|---|---|---|---|
| 305 | 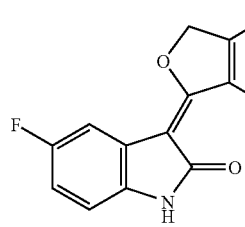 | 5-Fluoro-3-(5-{2-[2-(tetrahydro-pyran-4-yl)-ethylamino]-ethyl}-3H-isobenzofuran-1-ylidene)-1,3-dihydro-indol-2-one | 422.497 | 8 |

TABLE 8-continued
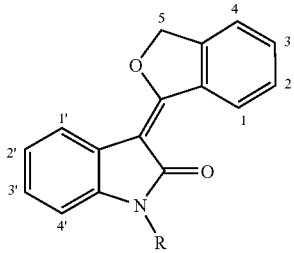
| 306 | 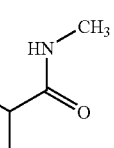 | 1-{2-[1-(5-Fluoro-2-oxo-1,2-dihydro-indol-3-ylidene)-1,3-dihydro-isobenzofuran-5-yl]-ethyl}-piperidine-4-carboxylic acid methylamide | 435.496 | 8 |
| --- | --- | --- | --- | --- |
| 307 | 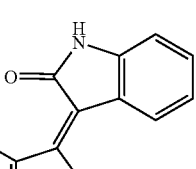 | 3-{5-[2-(2,6-Dimethyl-morpholin-4-yl)-ethyl]-3H-isobenzofuran-1-ylidene}-1,3-dihydro-indol-2-one | 390.48 | 8 |
| 308 | 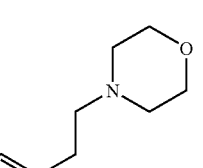 | 5-Fluoro-3-[5-(2-morpholin-4-yl-ethyl)-3H-isobenzofuran-1-ylidene]-1,3-dihydro-indol-2-one | 380.417 | 8 |

TABLE 8-continued
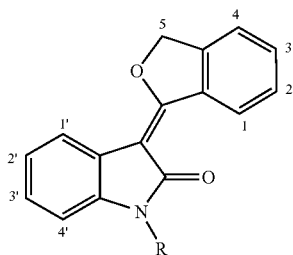
| 309 | 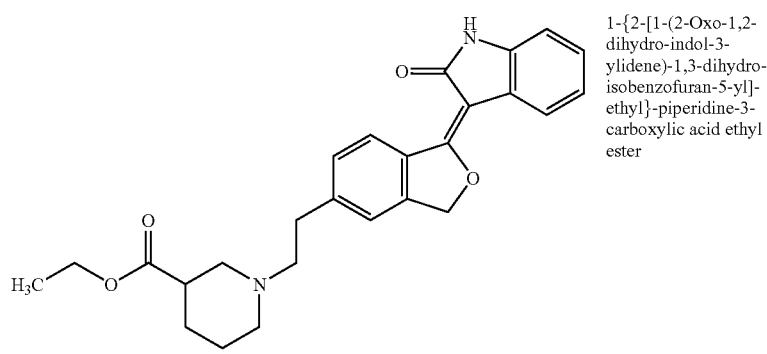 | 1-{2-[1-(2-Oxo-1,2-dihydro-indol-3-ylidene)-1,3-dihydro-isobenzofuran-5-yl]-ethyl}-piperidine-3-carboxylic acid ethyl ester | 432.517 | 8 |
| --- | --- | --- | --- | --- |
| 310 | 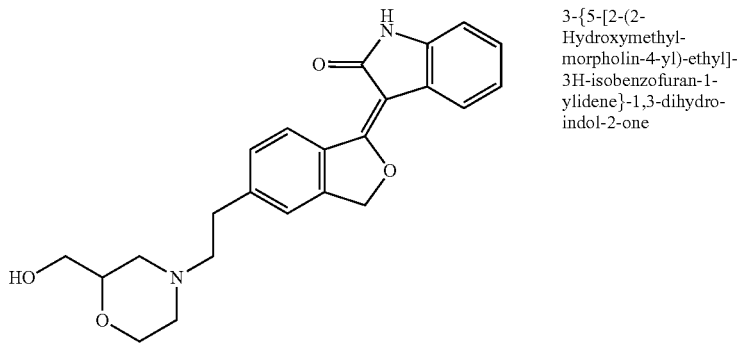 | 3-{5-[2-(2-Hydroxymethyl-morpholin-4-yl)-ethyl]-3H-isobenzofuran-1-ylidene}-1,3-dihydro-indol-2-one | 392.453 | 8 |
| 311 | 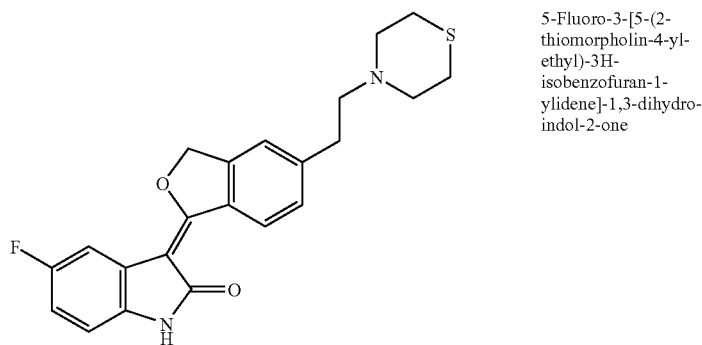 | 5-Fluoro-3-[5-(2-thiomorpholin-4-yl-ethyl)-3H-isobenzofuran-1-ylidene]-1,3-dihydro-indol-2-one | 396.484 | 8 |

TABLE 8-continued
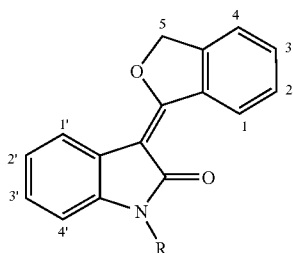
| | | | | |
|---|---|---|---|---|
| 312 | 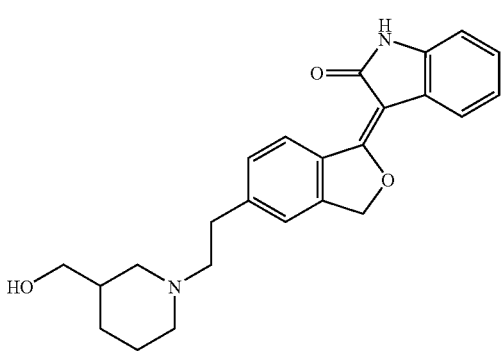 [SMILES: O=C1Nc2ccccc2/C1=C1\OCc2cc(CCN3CCOC(CO)C3)ccc21] | 3-{5-[2-(3-Hydroxymethyl-piperidin-1-yl)-ethyl]-3H-isobenzofuran-1-ylidene}-1,3-dihydro-indol-2-one | 390.48 | 8 |
| 313 | 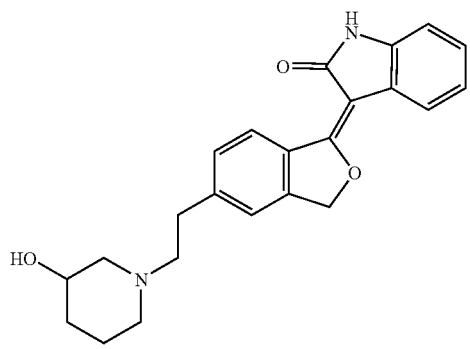 [SMILES: O=C1Nc2ccccc2/C1=C1\OCc2cc(CCN3CCCC(O)C3)ccc21] | 3-{5-[2-(3-Hydroxy-piperidin-1-yl)-ethyl]-3H-isobenzofuran-1-ylidene}-1,3-dihydro-indol-2-one | 376.454 | 8 |
| 314 | Chiral<br>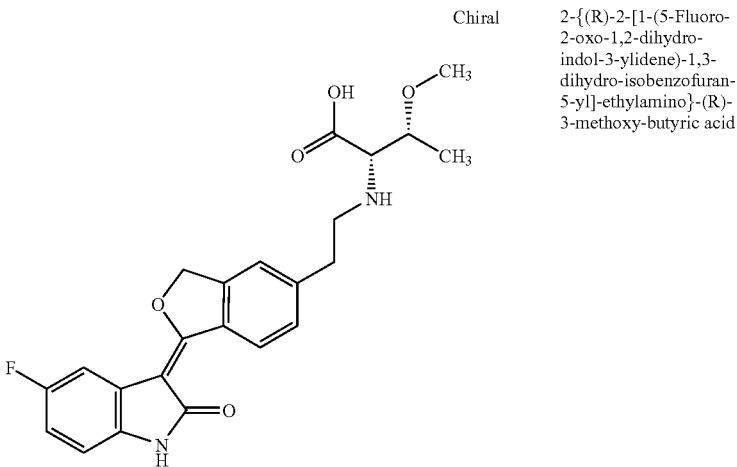 | 2-{(R)-2-[1-(5-Fluoro-2-oxo-1,2-dihydro-indol-3-ylidene)-1,3-dihydro-isobenzofuran-5-yl]-ethylamino}-(R)-3-methoxy-butyric acid | 426.442 | 8 |

TABLE 8-continued
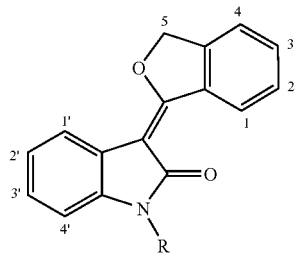
| | | | | |
|---|---|---|---|---|
| 315 | 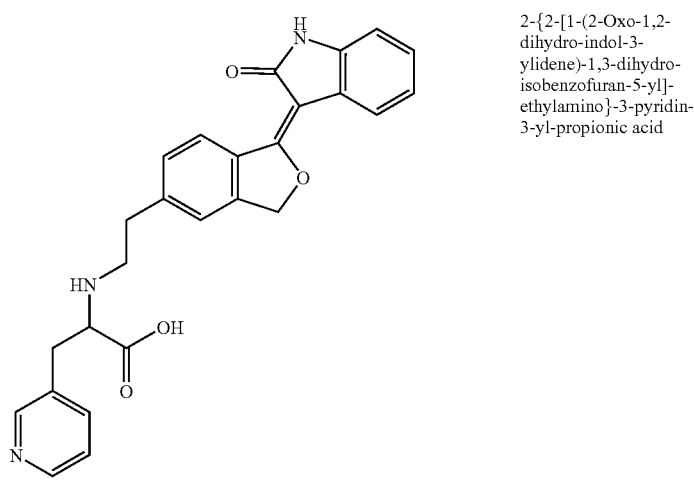 | 2-{2-[1-(2-Oxo-1,2-dihydro-indol-3-ylidene)-1,3-dihydro-isobenzofuran-5-yl]-ethylamino}-3-pyridin-3-yl-propionic acid | 441.485 | 8 |
| 316 | 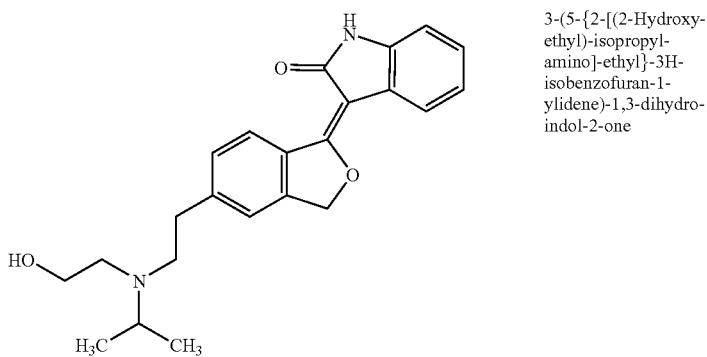 | 3-(5-{2-[(2-Hydroxy-ethyl)-isopropyl-amino]-ethyl}-3H-isobenzofuran-1-ylidene)-1,3-dihydro-indol-2-one | 378.469 | 8 |
| 317 | 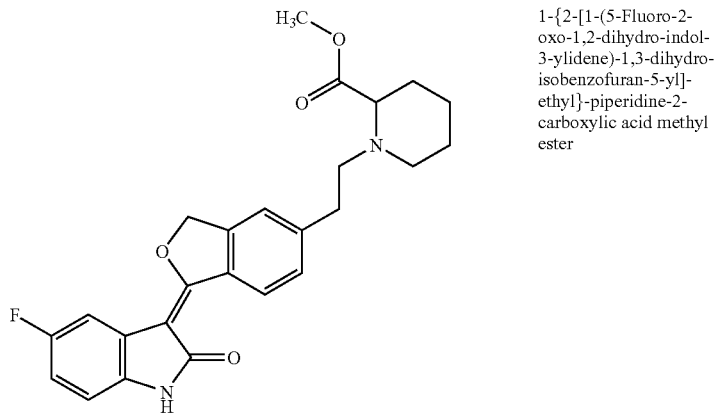 | 1-{2-[1-(5-Fluoro-2-oxo-1,2-dihydro-indol-3-ylidene)-1,3-dihydro-isobenzofuran-5-yl]-ethyl}-piperidine-2-carboxylic acid methyl ester | 436.48 | 8 |

TABLE 8-continued

| | | | | |
|---|---|---|---|---|
| 318 | | 3-{5-[2-(4-Hydroxymethyl-piperidin-1-yl)-ethyl]-3H-isobenzofuran-1-ylidene}-1,3-dihydro-indol-2-one | 390.48 | 8 |
| 319 | Chiral | 3-[5-(2-{[(2S)-2,3-Dihydroxy-propyl]-isopropyl-amino}-ethyl)-3H-isobenzofuran-1-ylidene]-5-fluoro-1,3-dihydro-indol-2-one | 426.485 | 8 |
| 320 | | 3-[5-(2-Thiomorpholin-4-yl-ethyl)-3H-isobenzofuran-1-ylidene]-1,3-dihydro-indol-2-one | 378.494 | 8 |

TABLE 8-continued
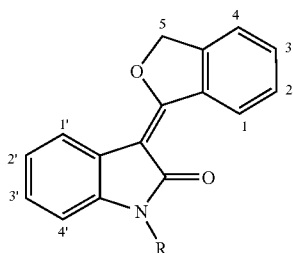
| | | | | |
|---|---|---|---|---|
| 321 | 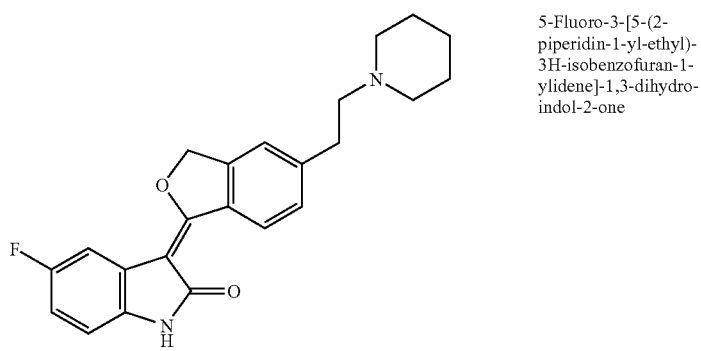 | 5-Fluoro-3-[5-(2-piperidin-1-yl-ethyl)-3H-isobenzofuran-1-ylidene]-1,3-dihydro-indol-2-one | 378.445 | 8 |
| 322 | 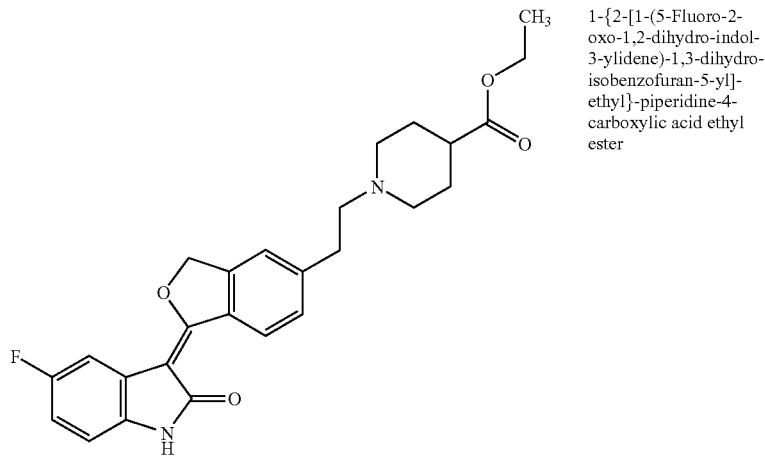 | 1-{2-[1-(5-Fluoro-2-oxo-1,2-dihydro-indol-3-ylidene)-1,3-dihydro-isobenzofuran-5-yl]-ethyl}-piperidine-4-carboxylic acid ethyl ester | 450.507 | 8 |
| 323 | 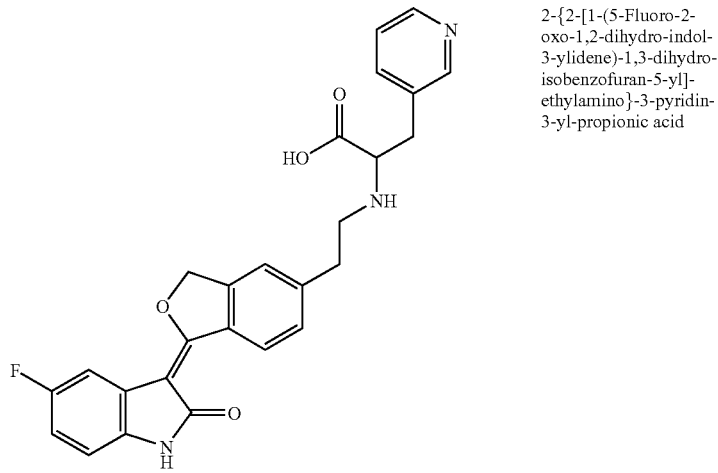 | 2-{2-[1-(5-Fluoro-2-oxo-1,2-dihydro-indol-3-ylidene)-1,3-dihydro-isobenzofuran-5-yl]-ethylamino}-3-pyridin-3-yl-propionic acid | 459.475 | 8 |

TABLE 8-continued

| 324 | Chiral | 3-[5-(2-{[(2R)-2,3-Dihydroxy-propyl]-isopropyl-amino}-ethyl)-3H-isobenzofuran-1-ylidene]-5-fluoro-1,3-dihydro-indol-2-one | 426.485 | 8 |
| --- | --- | --- | --- | --- |
| 325 | | 1-{2-[1-(2-Oxo-1,2-dihydro-indol-3-ylidene)-1,3-dihydro-isobenzofuran-5-yl]-ethyl}-piperidine-2-carboxylic acid ethyl ester | 432.517 | 8 |
| 326 | | 5-Fluoro-3-{5-[2-(2-hydroxymethyl-piperidin-1-yl)-ethyl]-3H-isobenzofuran-1-ylidene}-1,3-dihydro-indol-2-one | 408.47 | 8 |

TABLE 8-continued
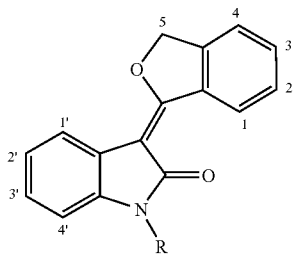
| 327 | 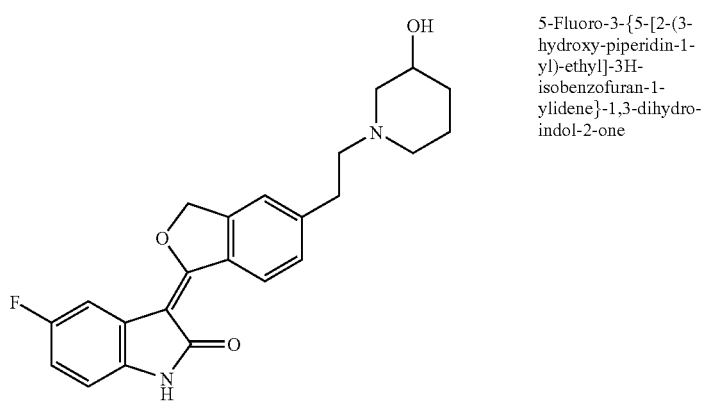 | 5-Fluoro-3-{5-[2-(3-hydroxy-piperidin-1-yl)-ethyl]-3H-isobenzofuran-1-ylidene}-1,3-dihydro-indol-2-one | 394.444 | 8 |
|---|---|---|---|---|
| 328 | 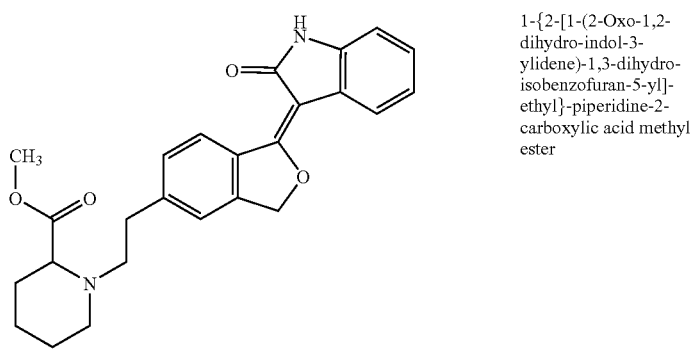 | 1-{2-[1-(2-Oxo-1,2-dihydro-indol-3-ylidene)-1,3-dihydro-isobenzofuran-5-yl]-ethyl}-piperidine-2-carboxylic acid methyl ester | 418.49 | 8 |
| 329 | 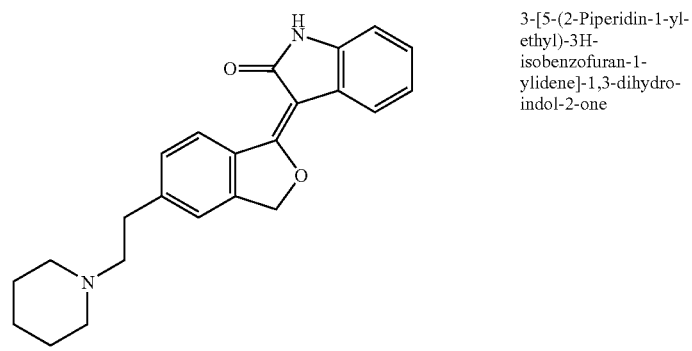 | 3-[5-(2-Piperidin-1-yl-ethyl)-3H-isobenzofuran-1-ylidene]-1,3-dihydro-indol-2-one | 360.455 | 8 |

TABLE 8-continued
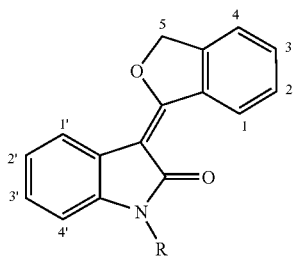
| | | | | |
|---|---|---|---|---|
| 330 | 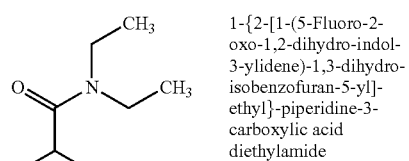 | 1-{2-[1-(5-Fluoro-2-oxo-1,2-dihydro-indol-3-ylidene)-1,3-dihydro-isobenzofuran-5-yl]-ethyl}-piperidine-3-carboxylic acid diethylamide | 477.577 | 8 |
| | 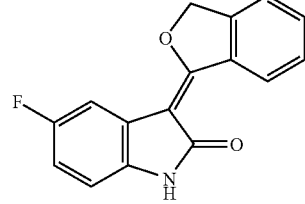 | | | |
| 331 | 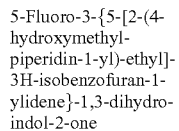 | 5-Fluoro-3-{5-[2-(4-hydroxymethyl-piperidin-1-yl)-ethyl]-3H-isobenzofuran-1-ylidene}-1,3-dihydro-indol-2-one | 408.47 | 8 |
| | 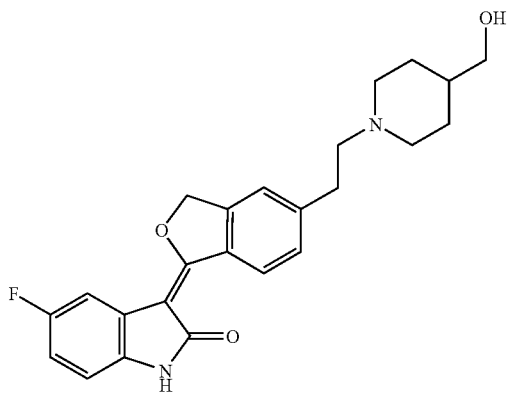 [SMILES: O=C1Nc2ccc(F)cc2/C1=C1\OCc2cc(CCN3CCC(CO)CC3)ccc21] | | | |
| 332 | 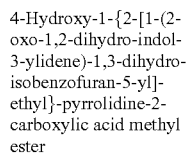 | 4-Hydroxy-1-{2-[1-(2-oxo-1,2-dihydro-indol-3-ylidene)-1,3-dihydro-isobenzofuran-5-yl]-ethyl}-pyrrolidine-2-carboxylic acid methyl ester | 420.463 | 8 |
| | 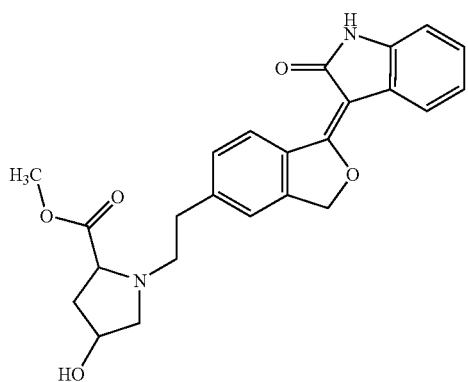 [SMILES: COC(=O)C1CC(O)CN1CCc1ccc2c(c1)CO/C2=C1/C(=O)Nc2ccccc21] | | | |

TABLE 8-continued
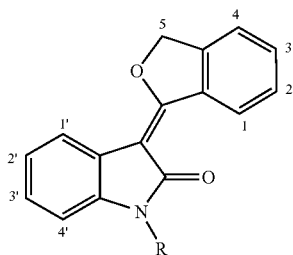
| | | | | | |
|---|---|---|---|---|---|
| 333 | | Chiral | 1-{2-[1-(5-Fluoro-2-oxo-1,2-dihydro-indol-3-ylidene)-1,3-dihydro-isobenzofuran-5-yl]-ethyl}-pyrrolidine-(S)-2-carboxylic acid methyl ester | 422.454 | 8 |
| 334 | | | 3-{5-[2-(4-Methyl-piperazin-1-yl)-ethyl]-3H-isobenzofuran-1-ylidene}-1,3-dihydro-indol-2-one | 375.47 | 8 |
| 335 | | | 3-(5-{2-[(2-Hydroxy-ethyl)-propyl-amino]-ethyl}-3H-isobenzofuran-1-ylidene)-1,3-dihydro-indol-2-one | 378.469 | 8 |

TABLE 8-continued
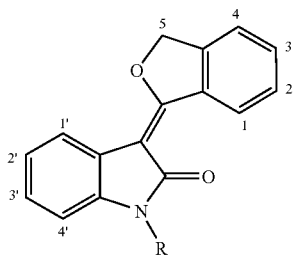
| 336 | 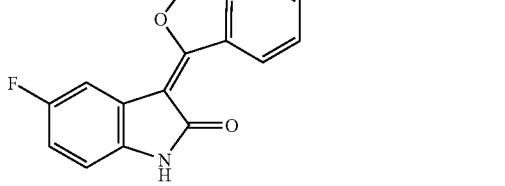 | 3-(5-{2-[(2-Diethylamino-ethyl)-(2-hydroxy-ethyl)-amino]-ethyl}-3H-isobenzofuran-1-ylidene)-5-fluoro-1,3-dihydro-indol-2-one | 453.555 | 8 |
|---|---|---|---|---|
| 337 | 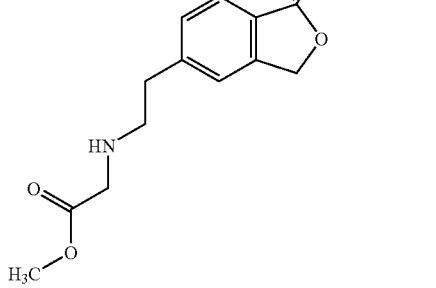 | {2-[1-(2-Oxo-1,2-dihydro-indol-3-ylidene)-1,3-dihydro-isobenzofuran-5-yl]-ethylamino}-acetic acid methyl ester | 364.399 | 8 |
| 338 | Chiral<br />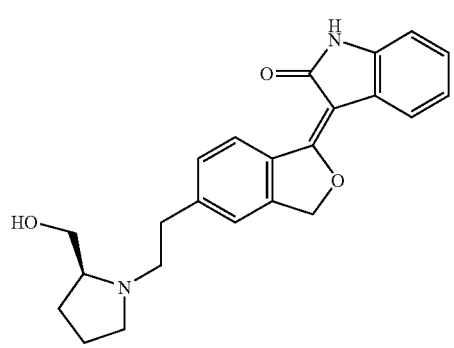 | 3-(5-{2-[(S)-2-Hydroxymethyl-pyrrolidin-1-yl]-ethyl}-3H-isobenzofuran-1-ylidene)-1,3-dihydro-indol-2-one | 376.454 | 8 |

TABLE 8-continued
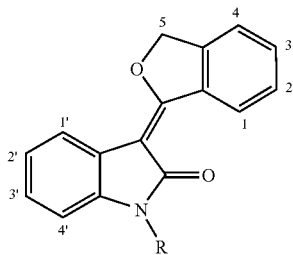
| 339 | 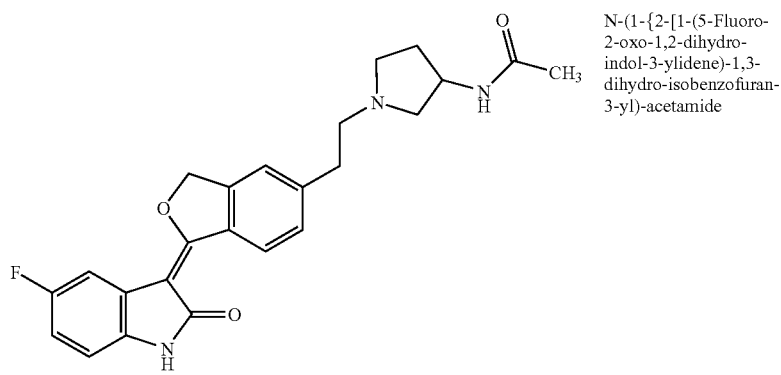 | N-(1-{2-[1-(5-Fluoro-2-oxo-1,2-dihydro-indol-3-ylidene)-1,3-dihydro-isobenzofuran-3-yl)-acetamide | 421.47 | 8 |
|---|---|---|---|---|
| 340 | 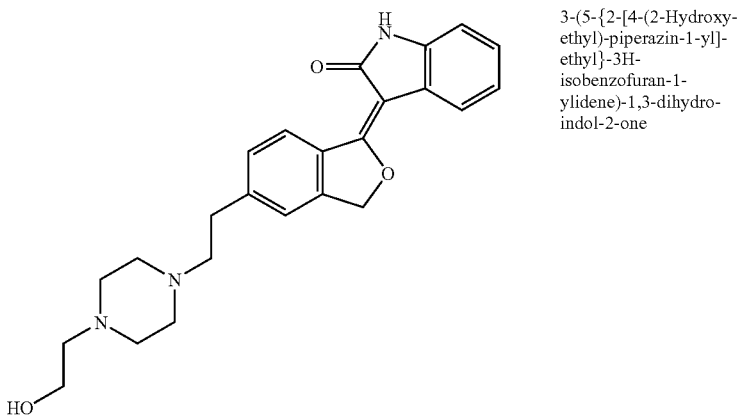 | 3-(5-{2-[4-(2-Hydroxy-ethyl)-piperazin-1-yl]-ethyl}-3H-isobenzofuran-1-ylidene)-1,3-dihydro-indol-2-one | 405.495 | 8 |
| 341 | 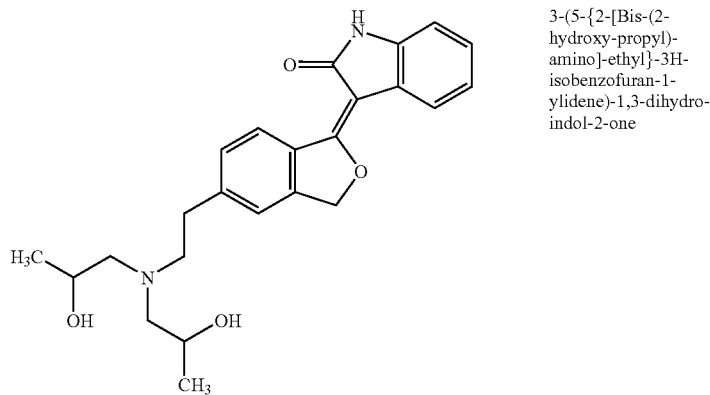 | 3-(5-{2-[Bis-(2-hydroxy-propyl)-amino]-ethyl}-3H-isobenzofuran-1-ylidene)-1,3-dihydro-indol-2-one | 408.495 | 8 |

TABLE 8-continued
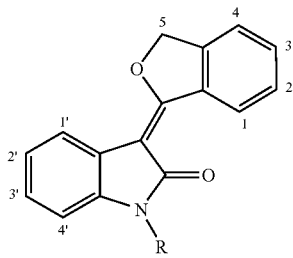
| 342 | 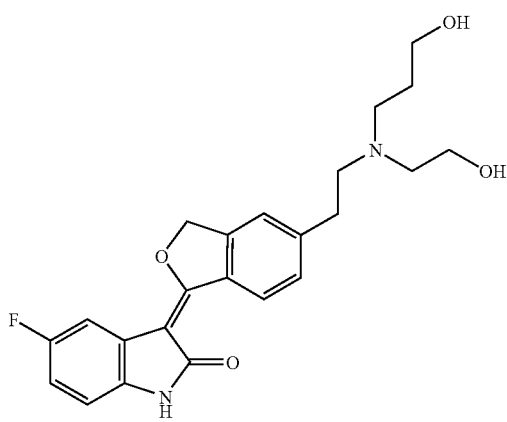 [SMILES: O=C1Nc2ccc(F)cc2/C1=C1\OCc2cc(CCN(CCO)CCCO)ccc21] | 5-Fluoro-3-(5-{2-[(2-hydroxy-ethyl)-(3-hydroxy-propyl)-amino]-ethyl}-3H-isobenzofuran-1-ylidene)-1,3-dihydro-indol-2-one | 412.458 | 8 |
| --- | --- | --- | --- | --- |
| 343 | 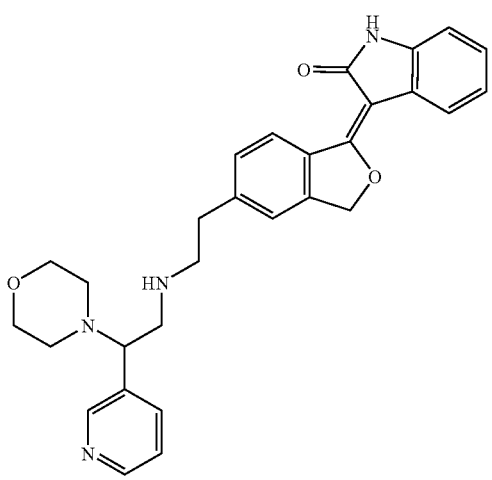 [SMILES: O=C1Nc2ccccc2/C1=C1\OCc2cc(CCNCC(c3cccnc3)N3CCOCC3)ccc21] | 3-{5-[2-(2-Morpholin-4-yl-2-pyridin-3-yl-ethylamino)-ethyl]-3H-isobenzofuran-1-ylidene}-1,3-dihydro-indol-2-one | 482.581 | 8 |
| 344 | Chiral<br>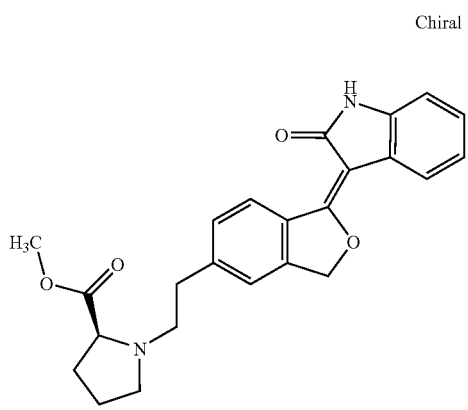 [SMILES: COC(=O)[C@@H]1CCCN1CCc1ccc2c(c1)CO/C2=C1/C(=O)Nc2ccccc21] | 1-{2-[1-(2-Oxo-1,2-dihydro-indol-3-ylidene)-1,3-dihydro-isobenzofuran-5-yl]-ethyl}-pyrrolidine-(S)-2-carboxylic acid methyl ester | 404.464 | 8 |

TABLE 8-continued
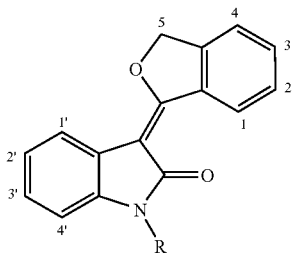
| 345 | 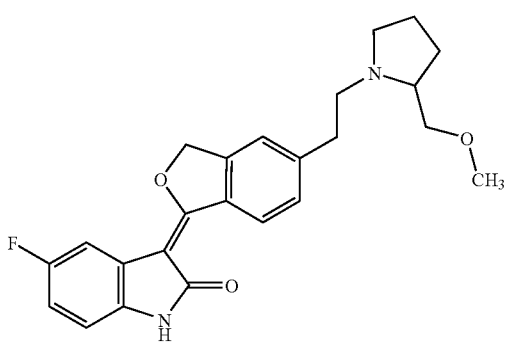 [SMILES: COCC1CCCN1CCc1ccc2c(c1)CO/C2=C1/C(=O)Nc2ccc(F)cc21] | 5-Fluoro-3-{5-[2-(2-methoxymethyl-pyrrolidin-1-yl)-ethyl]-3H-isobenzofuran-1-ylidene}-1,3-dihydro-indol-2-one | 408.47 | 8 |
| --- | --- | --- | --- | --- |
| 346 | 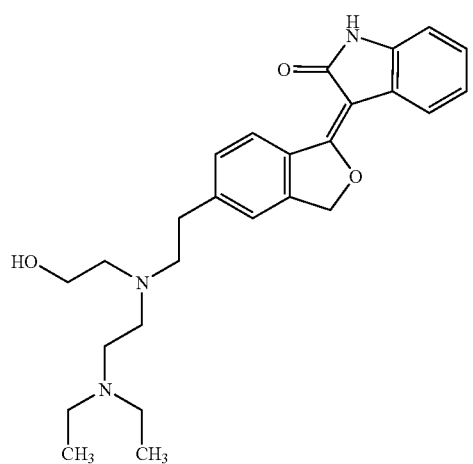 [SMILES: CCN(CC)CCN(CCO)CCc1ccc2c(c1)CO/C2=C1/C(=O)Nc2ccccc21] | 3-(5-{2-[(2-Diethylamino-ethyl)-(2-hydroxy-ethyl)-amino]-ethyl}-3H-isobenzofuran-1-ylidene)-1,3-dihydro-indol-2-one | 435.565 | 8 |
| 347 | 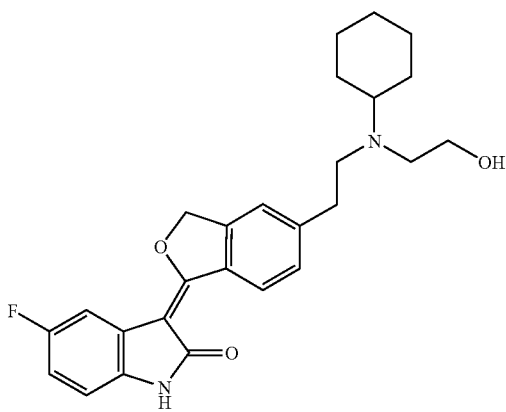 [SMILES: O=C1Nc2ccc(F)cc2/C1=C1\OCc2cc(CCN(CCO)C3CCCCC3)ccc21] | 3-(5-{2-[Cyclohexyl-(2-hydroxy-ethyl)-amino]-ethyl}-3H-isobenzofuran-1-ylidene)-5-fluoro-1,3-dihydro-indol-2-one | 436.524 | 8 |

TABLE 8-continued
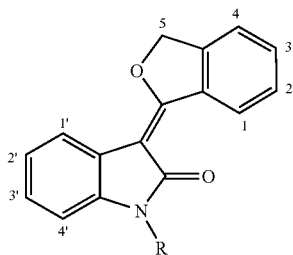
| 348 | 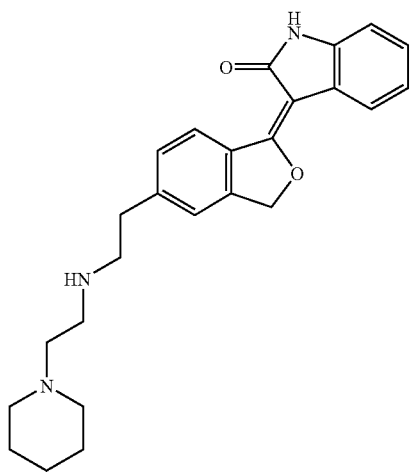 [SMILES: O=C1Nc2ccccc2/C1=C1\OCc2cc(CCNCCN3CCCCC3)ccc21] | 3-{5-[2-(2-Piperidin-1-yl-ethylamino)-ethyl]-3H-isobenzofuran-1-ylidene}-1,3-dihydro-indol-2-one | 403.523 | 8 |
| --- | --- | --- | --- | --- |
| 349 | 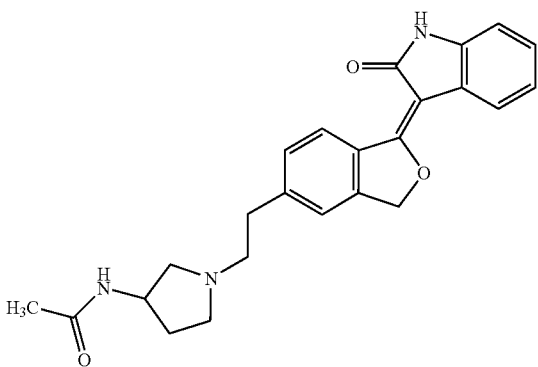 [SMILES: CC(=O)NC1CCN(CCc2ccc3c(c2)CO/C3=C2/C(=O)Nc3ccccc32)C1] | N-(1-{2-[1-(2-Oxo-1,2-dihydro-indol-3-ylidene)-1,3-dihydro-isobenzofuran-5-yl]-ethyl}-pyrrolidin-3-yl)-acetamide | 403.479 | 8 |
| 350 | Chiral<br>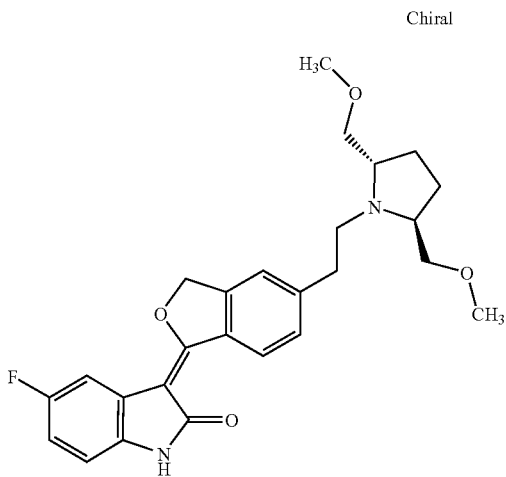 [SMILES: COC[C@@H]1CC[C@@H](COC)N1CCc1ccc2c(c1)CO/C2=C1/C(=O)Nc2ccc(F)cc21] | 3-(5-{2-[(S, S)-2,5-Bis-methoxymethyl-pyrrolidin-1-yl]-ethyl}-3H-isobenzofuran-1-ylidene)-5-fluoro-1,3-dihydro-indol-2-one | 452.523 | 8 |

TABLE 8-continued
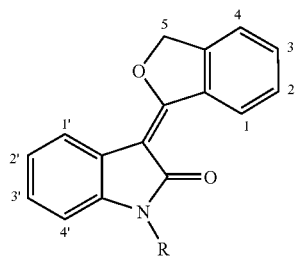
| 351 | 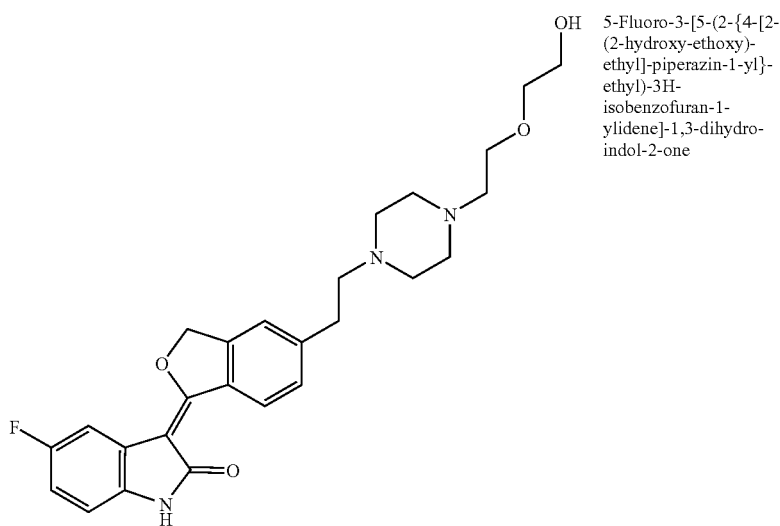 | 5-Fluoro-3-[5-(2-{4-[2-(2-hydroxy-ethoxy)-ethyl]-piperazin-1-yl}-ethyl)-3H-isobenzofuran-1-ylidene]-1,3-dihydro-indol-2-one | 467.538 | 8 |
| --- | --- | --- | --- | --- |
| 352 | 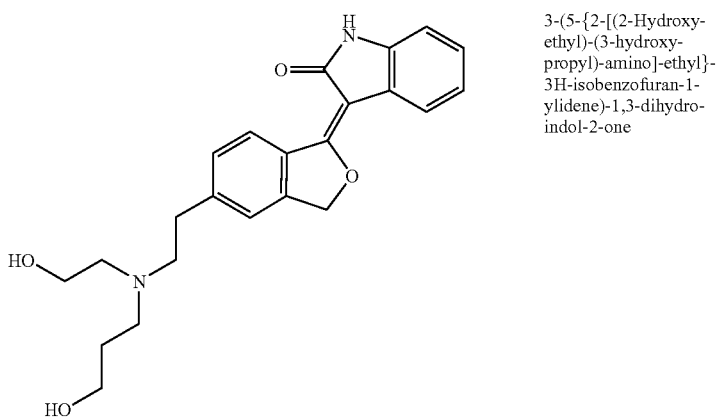 | 3-(5-{2-[(2-Hydroxy-ethyl)-(3-hydroxy-propyl)-amino]-ethyl}-3H-isobenzofuran-1-ylidene)-1,3-dihydro-indol-2-one | 394.468 | 8 |

TABLE 8-continued
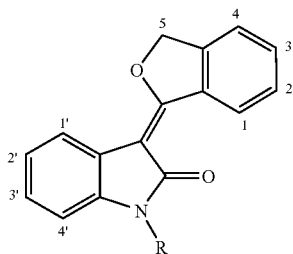
| | | | | |
|---|---|---|---|---|
| 353 | 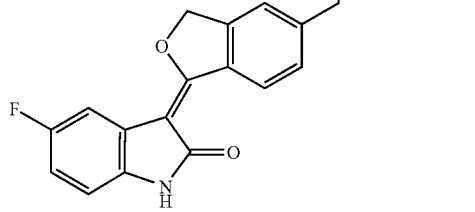 | 3-(5-{2-[Ethyl-(2-pyridin-2-yl-ethyl)-amino]-ethyl}-3H-isobenzofuran-1-ylidene)-5-fluoro-1,3-dihydro-indol-2-one | 443.519 | 8 |
| 354 | 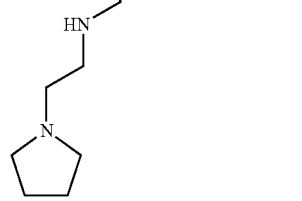 | 3-{5-[2-(2-Pyrrolidin-1-yl-ethylamino)-ethyl]-3H-isobenzofuran-1-ylidene}-1,3-dihydro-indol-2-one | 389.496 | 8 |
| 355 | 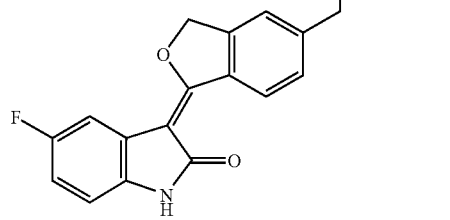 | 5-Fluoro-3-{5-[2-(3-fluoro-piperidin-1-yl)-ethyl]-3H-isobenzofuran-1-ylidene}-1,3-dihydro-indol-2-one | 396.435 | 8 |

TABLE 8-continued
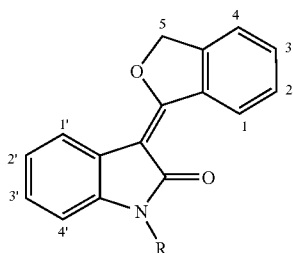
| | | | | |
|---|---|---|---|---|
| 356 | | 3-{5-[2-(2-Methoxymethyl-pyrrolidin-1-yl)-ethyl]-3H-isobenzofuran-1-ylidene}-1,3-dihydro-indol-2-one | 390.48 | 8 |
| 357 | | 3-(5-{2-[4-(2-Dimethylamino-ethyl)-piperazin-1-yl]-ethyl}-3H-isobenzofuran-1-ylidene)-5-fluoro-1,3-dihydro-indol-2-one | 450.555 | 8 |
| 358 | | 3-(5-{2-[4-(2-Ethoxy-ethyl)-piperazin-1-yl]-ethyl}-3H-isobenzofuran-1-ylidene)-5-fluoro-1,3-dihydro-indol-2-one | 451.539 | 8 |

TABLE 8-continued
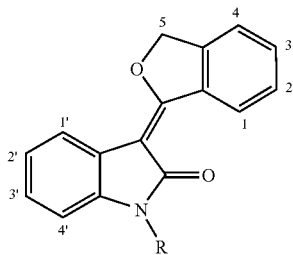
| | | | | |
|---|---|---|---|---|
| 359 | 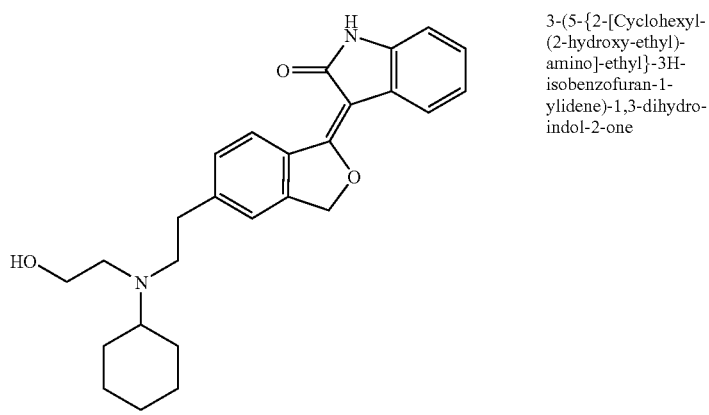 | 3-(5-{2-[Cyclohexyl-(2-hydroxy-ethyl)-amino]-ethyl}-3H-isobenzofuran-1-ylidene)-1,3-dihydro-indol-2-one | 418.534 | 8 |
| 360 | 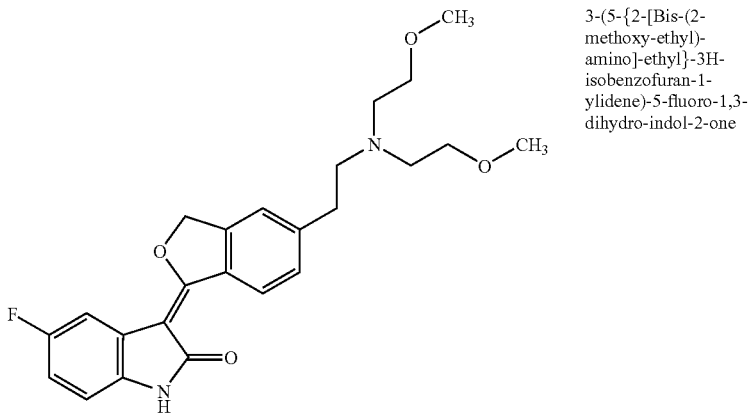 | 3-(5-{2-[Bis-(2-methoxy-ethyl)-amino]-ethyl}-3H-isobenzofuran-1-ylidene)-5-fluoro-1,3-dihydro-indol-2-one | 426.485 | 8 |
| 361 | 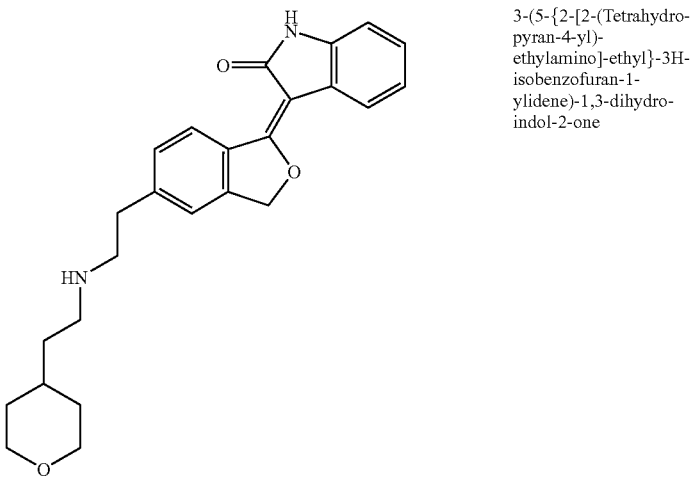 | 3-(5-{2-[2-(Tetrahydro-pyran-4-yl)-ethylamino]-ethyl}-3H-isobenzofuran-1-ylidene)-1,3-dihydro-indol-2-one | 404.507 | 8 |

TABLE 8-continued

| | | | | | |
|---|---|---|---|---|---|
| 362 | | Chiral | 1-{2-[1-(5-Fluoro-2-oxo-1,2-dihydro-indol-3-ylidene)-1,3-dihydro-isobenzofuran-5-yl]-ethyl}-pyrrolidine-(S)-2-carboxylic acid ethyl ester | 436.48 | 8 |
| 363 | | Chiral | 3-{5-[2-(S,S)-2,5-Bis-methoxymethyl-pyrrolidin-1-yl)-ethyl]-3H-isobenzofuran-1-ylidene}-1,3-dihydro-indol-2-one | 434.533 | 8 |
| 364 | | | 4-{2-[1-(5-Fluoro-2-oxo-1,2-dihydro-indol-3-ylidene)-1,3-dihydro-isobenzofuran-5-yl]-ethyl}-piperazine-1-carboxylic acid ethyl ester | 451.495 | 8 |

TABLE 8-continued
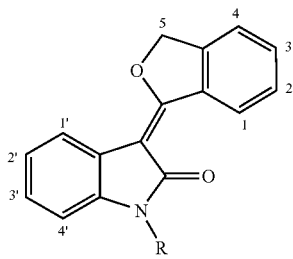
| | | | | |
|---|---|---|---|---|
| 365 | 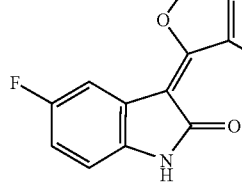 | (4-{2-[1-(5-Fluoro-2-oxo-1,2-dihydro-indol-3-ylidene)-1,3-dihydro-isobenzofuran-5-yl]-ethyl}-piperazin-1-yl)-acetic acid | 437.469 | 8 |
| 366 | 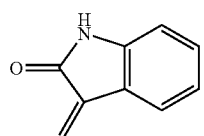 | 3-(5-{2-[Ethyl-(2-pyridin-2-yl-ethyl)-amino]-ethyl}-3H-isobenzofuran-1-ylidene)-1,3-dihydro-indol-2-one | 425.529 | 8 |
| 367 | 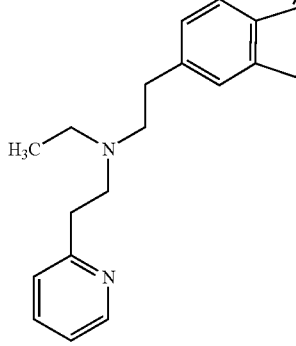 | 3-(5-{2-[Bis-(2-ethoxy-ethyl)-amino]-ethyl}-3H-isobenzofuran-1-ylidene)-5-fluoro-1,3-dihydro-indol-2-one | 454.539 | 8 |
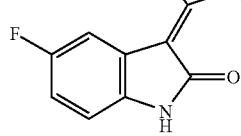

TABLE 8-continued
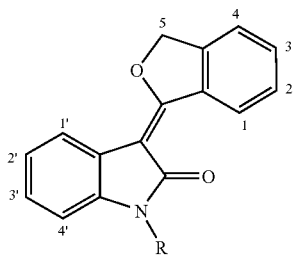
| | | | | |
|---|---|---|---|---|
| 368 | 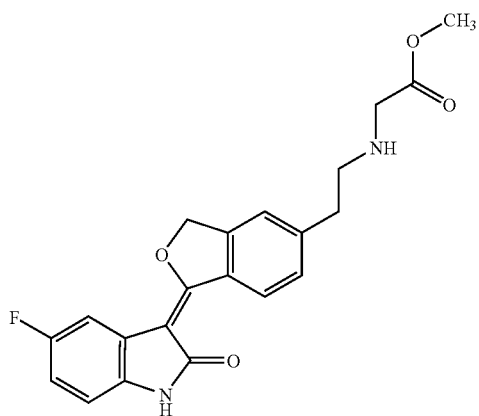 [SMILES: COC(=O)CNCCc1ccc2c(c1)CO/C2=C1/C(=O)Nc2ccc(F)cc21] | {2-[1-(5-Fluoro-2-oxo-1,2-dihydro-indol-3-ylidene)-1,3-dihydro-isobenzofuran-5-yl]-ethylamino}-acetic acid methyl ester | 382.389 | 8 |
| 369 | 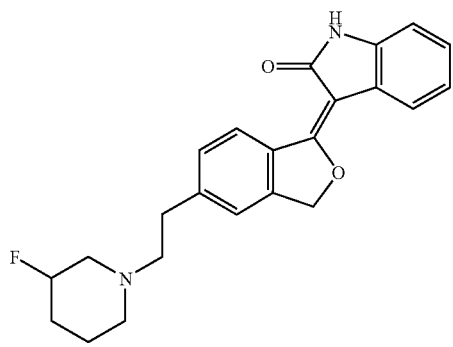 [SMILES: O=C1Nc2ccccc2/C1=C1\OCc2cc(CCN3CCCC(F)C3)ccc21] | 3-{5-[2-(3-Fluoro-piperidin-1-yl)-ethyl]-3H-isobenzofuran-1-ylidene}-1,3-dihydro-indol-2-one | 378.445 | 8 |
| 370 | 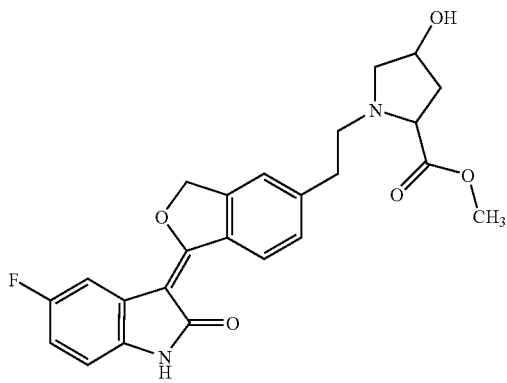 [SMILES: COC(=O)C1CC(O)CN1CCc1ccc2c(c1)CO/C2=C1/C(=O)Nc2ccc(F)cc21] | 1-{2-[1-(5-Fluoro-2-oxo-1,2-dihydro-indol-3-ylidene)-1,3-dihydro-isobenzofuran-5-yl]-ethyl}-4-hydroxy-pyrrolidine-2-carboxylic acid methyl ester | 438.453 | 8 |

TABLE 8-continued
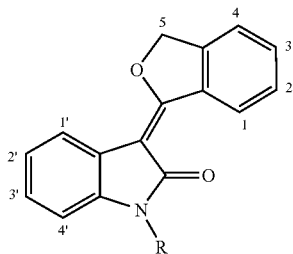
| | | | | |
|---|---|---|---|---|
| 371 | 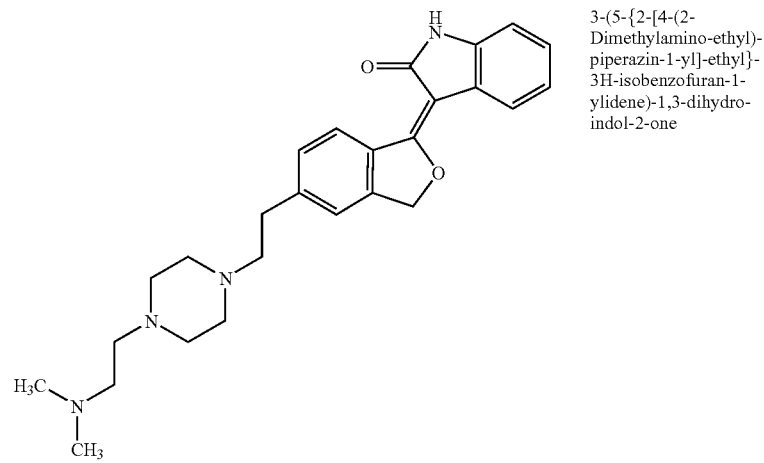 | 3-(5-{2-[4-(2-Dimethylamino-ethyl)-piperazin-1-yl]-ethyl}-3H-isobenzofuran-1-ylidene)-1,3-dihydro-indol-2-one | 432.565 | 8 |
| 372 | 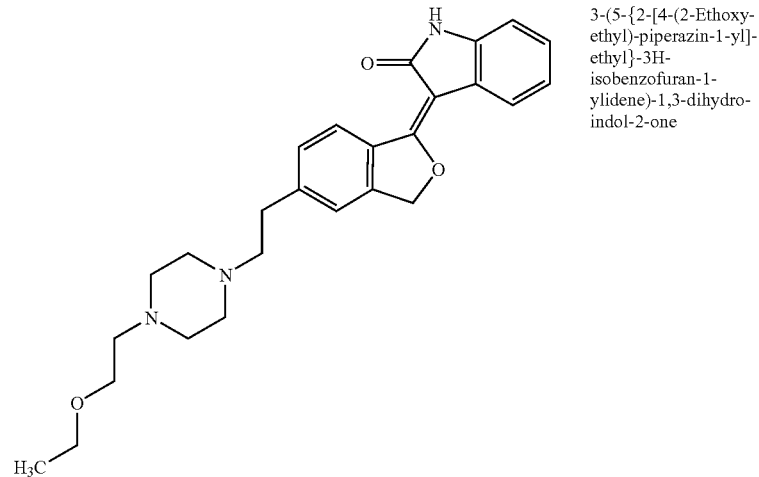 | 3-(5-{2-[4-(2-Ethoxy-ethyl)-piperazin-1-yl]-ethyl}-3H-isobenzofuran-1-ylidene)-1,3-dihydro-indol-2-one | 433.549 | 8 |
| 373 | 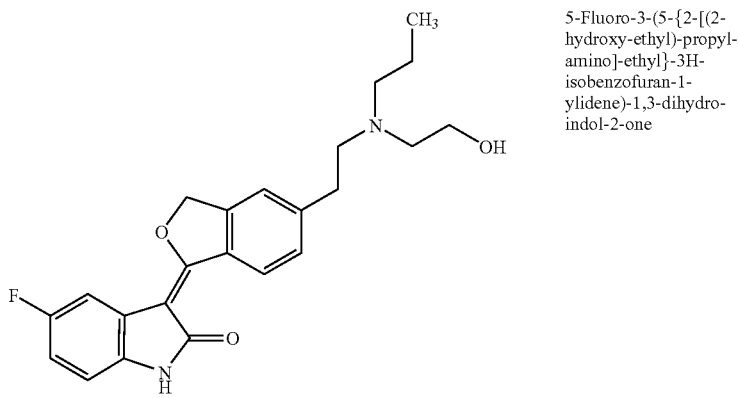 | 5-Fluoro-3-(5-{2-[(2-hydroxy-ethyl)-propyl-amino]-ethyl}-3H-isobenzofuran-1-ylidene)-1,3-dihydro-indol-2-one | 396.46 | 8 |

TABLE 8-continued
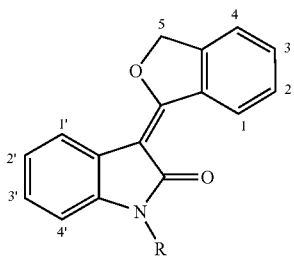
| 374 | 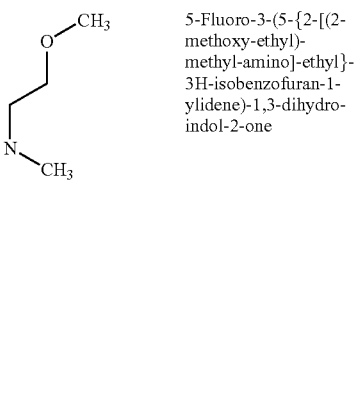 | 5-Fluoro-3-(5-{2-[(2-methoxy-ethyl)-methyl-amino]-ethyl}-3H-isobenzofuran-1-ylidene)-1,3-dihydro-indol-2-one | 382.433 | 8 |
| 375 | 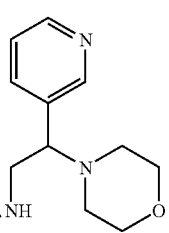 | 5-Fluoro-3-{5-[2-(2-morpholin-4-yl-2-pyridin-3-yl-ethylamino)-ethyl]-3H-isobenzofuran-1-ylidene}-1,3-dihydro-indol-2-one | 500.571 | 8 |
| 376 | Chiral 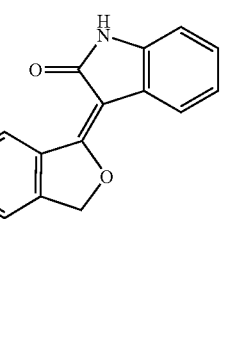 | 1-{2-[1-(2-Oxo-1,2-dihydro-indol-3-ylidene)-1,3-dihydro-isobenzofuran-5-yl]-ethyl}-pyrrolidine-(R)-2-carboxylic acid ethyl ester | 418.49 | 8 |

TABLE 8-continued
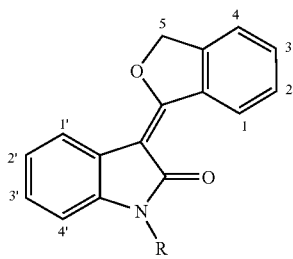
| | | | | |
|---|---|---|---|---|
| 377 | 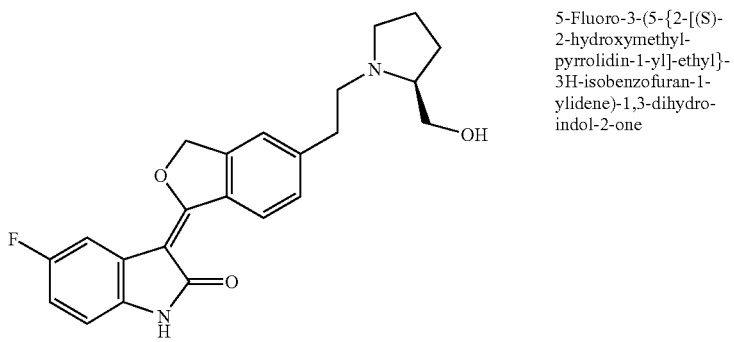 | 5-Fluoro-3-(5-{2-[(S)-2-hydroxymethyl-pyrrolidin-1-yl]-ethyl}-3H-isobenzofuran-1-ylidene)-1,3-dihydro-indol-2-one | 394.444 | 8 |
| 378 | 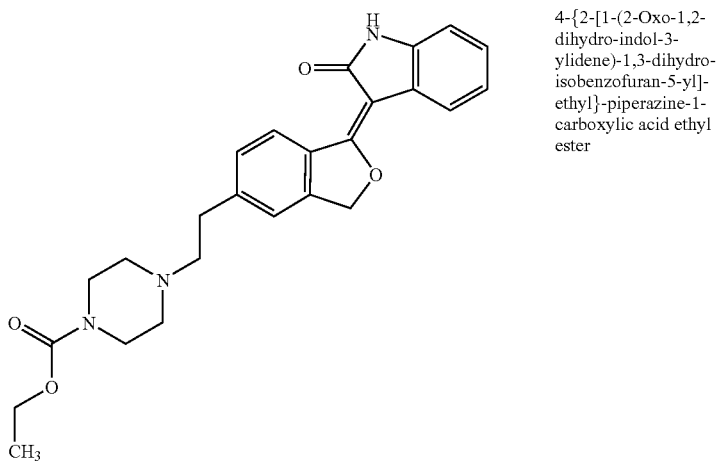 | 4-{2-[1-(2-Oxo-1,2-dihydro-indol-3-ylidene)-1,3-dihydro-isobenzofuran-5-yl]-ethyl}-piperazine-1-carboxylic acid ethyl ester | 433.505 | 8 |
| 379 | 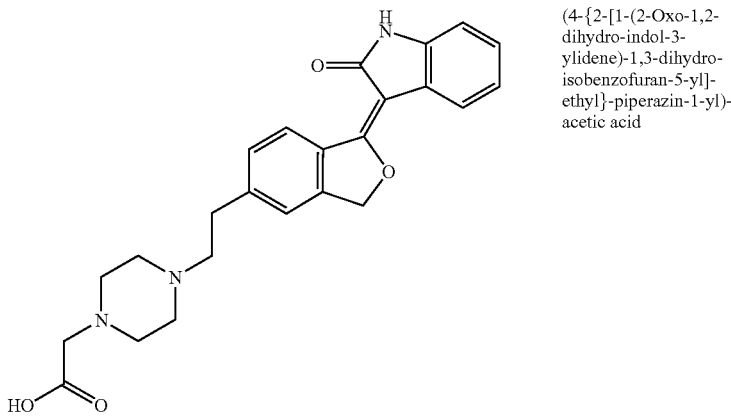 | (4-{2-[1-(2-Oxo-1,2-dihydro-indol-3-ylidene)-1,3-dihydro-isobenzofuran-5-yl]-ethyl}-piperazin-1-yl)-acetic acid | 419.478 | 8 |

TABLE 8-continued

| 380 | (structure) | 3-(5-{2-[Bis-(2-hydroxy-propyl)-amino]-ethyl}-3H-isobenzofuran-1-ylidene)-5-fluoro-1,3-dihydro-indol-2-one | 426.485 | 8 |
| --- | --- | --- | --- | --- |
| 381 | (structure) | 3-(5-{2-[Bis-(2-ethoxy-ethyl)-amino]-ethyl}-3H-isobenzofuran-1-ylidene)-1,3-dihydro-indol-2-one | 436.549 | 8 |
| 382 | (structure) | 5-Fluoro-3-{5-[2-(2-pyrrolidin-1-yl-ethylamino)-ethyl]-3H-isobenzofuran-1-ylidene}-1,3-dihydro-indol-2-one | 407.486 | 8 |

TABLE 8-continued
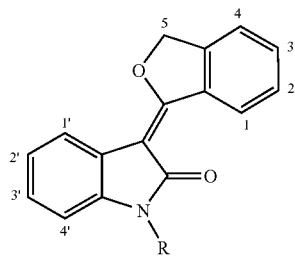
| | | | | |
|---|---|---|---|---|
| 383 | 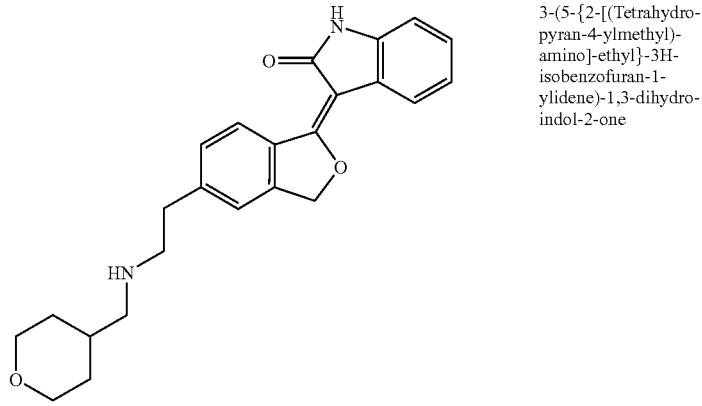 | 3-(5-{2-[(Tetrahydro-pyran-4-ylmethyl)-amino]-ethyl}-3H-isobenzofuran-1-ylidene)-1,3-dihydro-indol-2-one | 390.48 | 8 |
| 384 | 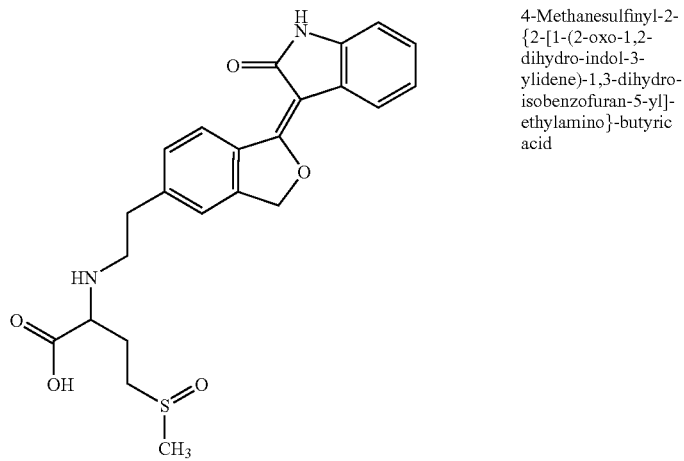 | 4-Methanesulfinyl-2-{2-[1-(2-oxo-1,2-dihydro-indol-3-ylidene)-1,3-dihydro-isobenzofuran-5-yl]-ethylamino}-butyric acid | 440.518 | 8 |
| 385 | 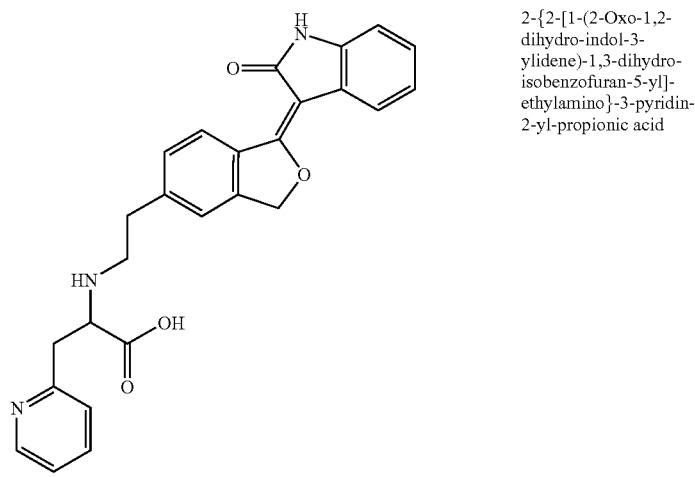 | 2-{2-[1-(2-Oxo-1,2-dihydro-indol-3-ylidene)-1,3-dihydro-isobenzofuran-5-yl]-ethylamino}-3-pyridin-2-yl-propionic acid | 441.485 | 8 |

TABLE 8-continued
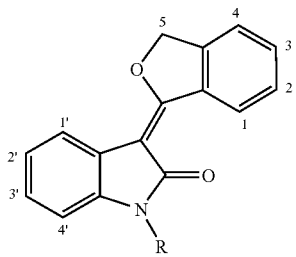
| 386 | 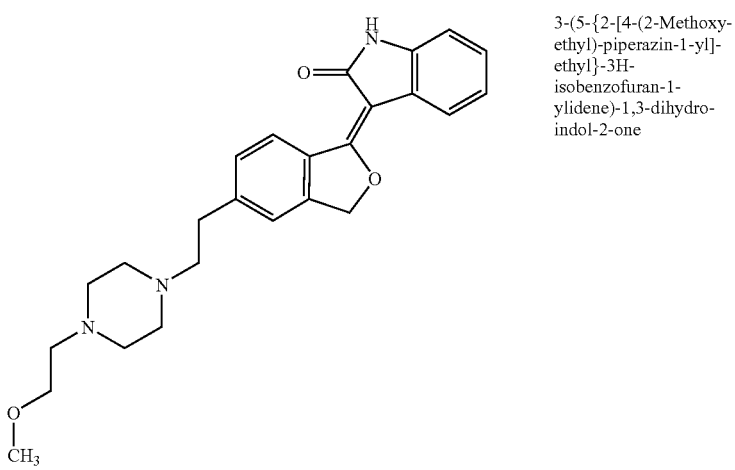 | 3-(5-{2-[4-(2-Methoxy-ethyl)-piperazin-1-yl]-ethyl}-3H-isobenzofuran-1-ylidene)-1,3-dihydro-indol-2-one | 419.522 | 8 |
|---|---|---|---|---|
| 387 | 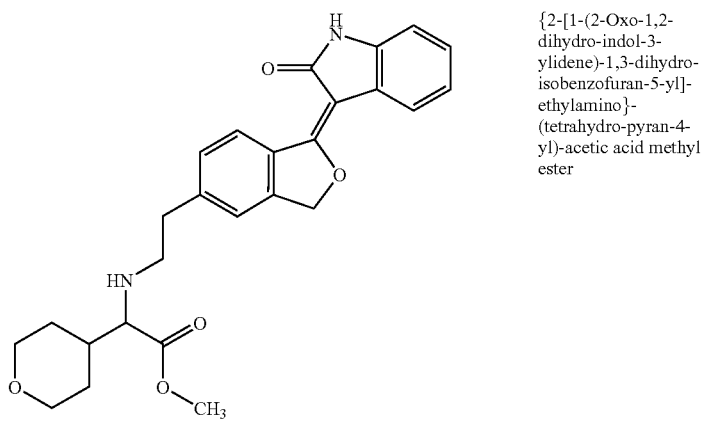 | {2-[1-(2-Oxo-1,2-dihydro-indol-3-ylidene)-1,3-dihydro-isobenzofuran-5-yl]-ethylamino}-(tetrahydro-pyran-4-yl)-acetic acid methyl ester | 448.516 | 8 |
| 388 | 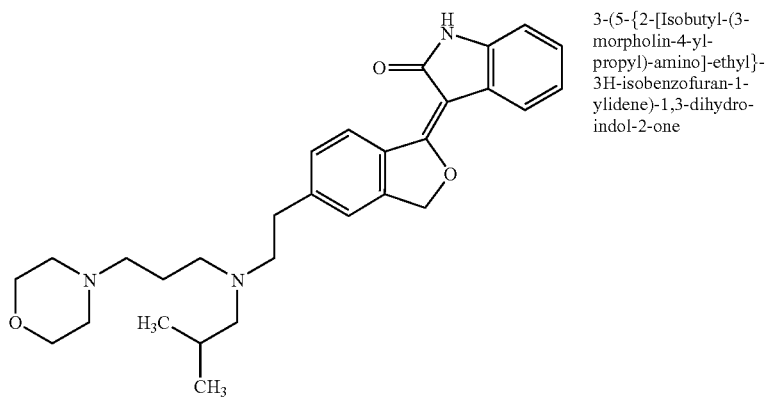 | 3-(5-{2-[Isobutyl-(3-morpholin-4-yl-propyl)-amino]-ethyl}-3H-isobenzofuran-1-ylidene)-1,3-dihydro-indol-2-one | 475.629 | 8 |

TABLE 8-continued
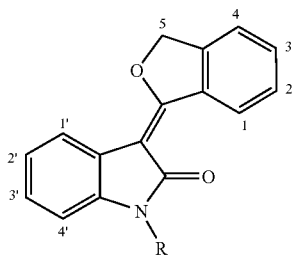
| 389 | 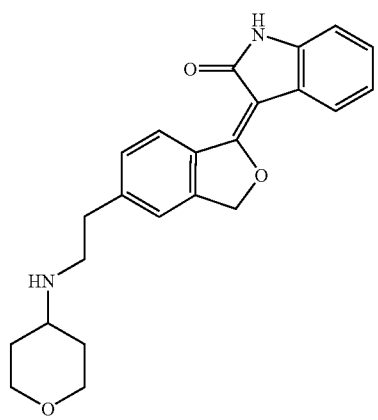 [SMILES: O=C1Nc2ccccc2/C1=C1\OCc2cc(CCNC3CCOCC3)ccc21] | 3-{5-[2-(Tetrahydro-pyran-4-ylamino)-ethyl]-3H-isobenzofuran-1-ylidene}-1,3-dihydro-indol-2-one | 376.454 | 8 |
| --- | --- | --- | --- | --- |
| 390 | 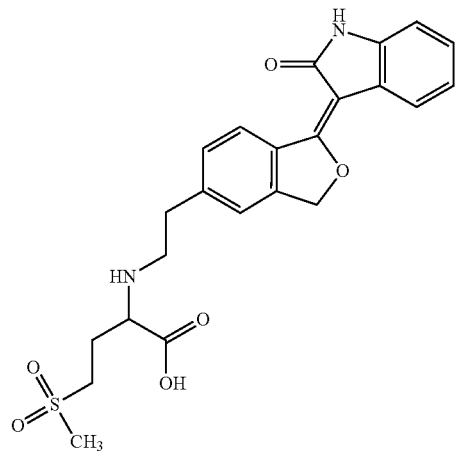 [SMILES: CS(=O)(=O)CCC(NCCc1ccc2c(c1)CO/C2=C1/C(=O)Nc2ccccc21)C(=O)O] | 4-Methanesulfonyl-2-{2-[1-(2-oxo-1,2-dihydro-indol-3-ylidene)-1,3-dihydro-isobenzofuran-5-yl]-ethylamino}-butyric acid | 456.517 | 8 |
| 391 | 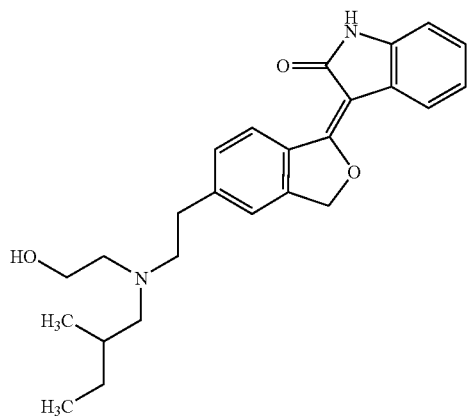 [SMILES: CCC(C)CN(CCO)CCc1ccc2c(c1)CO/C2=C1/C(=O)Nc2ccccc21] | 3-(5-{2-[(2-Hydroxy-ethyl)-(2-methyl-butyl)-amino]-ethyl}-3H-isobenzofuran-1-ylidene)-1,3-dihydro-indol-2-one | 406.523 | 8 |

TABLE 8-continued
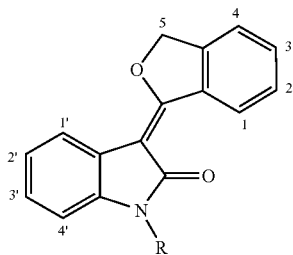
| | | | | |
|---|---|---|---|---|
| 392 | 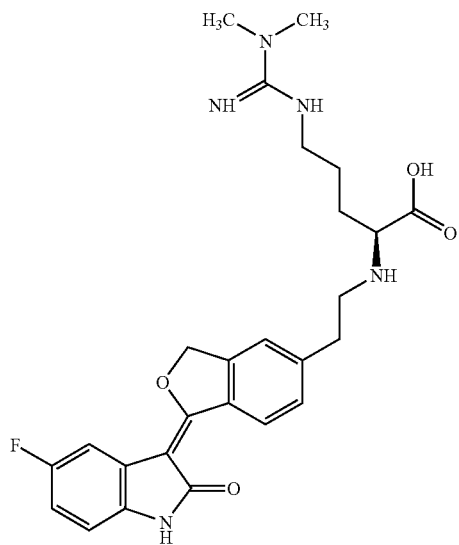 [SMILES: CN(C)C(=N)NCCC[C@H](NCCc1ccc2c(c1)CO/C2=C1/C(=O)Nc2ccc(F)cc21)C(=O)O] | 5-(N',N'-Dimethyl-guanidino)-(S)-2-{2-[1-(5-fluoro-2-oxo-1,2-dihydro-indol-3-ylidene)-1,3-dihydro-isobenzofuran-5-yl]-ethylamino}-pentanoic acid | 495.552 | 8 |
| 393 | 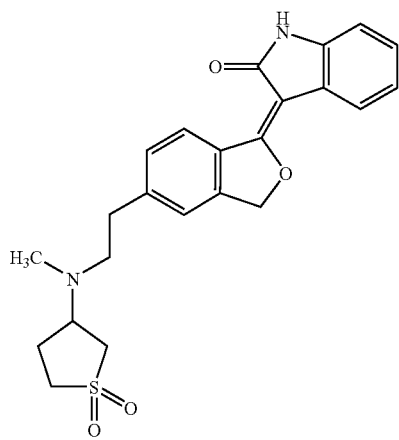 [SMILES: CN(CCc1ccc2c(c1)CO/C2=C1/C(=O)Nc2ccccc21)C1CCS(=O)(=O)C1] | 3-(5-{2-[(1,1-Dioxo-tetrahydro-1lambda*6*-thiophen-3-yl)-methyl-amino]-ethyl}-3H-isobenzofuran-1-ylidene)-1,3-dihydro-indol-2-one | 424.519 | 8 |

TABLE 8-continued

| | | | | | |
|---|---|---|---|---|---|
| 394 | | Chiral | (S)-3-Hydroxy-(S)-2-{2-[1-(2-oxo-1,2-dihydro-indol-3-ylidene)-1,3-dihydro-isobenzofuran-5-yl]-ethylamino}-butyric acid methyl ester | 408.452 | 8 |
| 395 | | | 2-{(S)-2-[1-(5-Fluoro-2-oxo-1,2-dihydro-indol-3-ylidene)-1,3-dihydro-isobenzofuran-5-yl]-ethylamino}-4-methylsulfanyl-butyric acid ethyl ester | 470.562 | 8 |
| 396 | | | 3-(5-{2-[Ethyl-(2-methoxy-ethyl)-amino]-ethyl}-3H-isobenzofuran-1-ylidene)-5-fluoro-1,3-dihydro-indol-2-one | 396.46 | 8 |

TABLE 8-continued
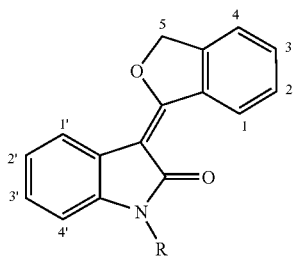
| | | | | |
|---|---|---|---|---|
| 397 | 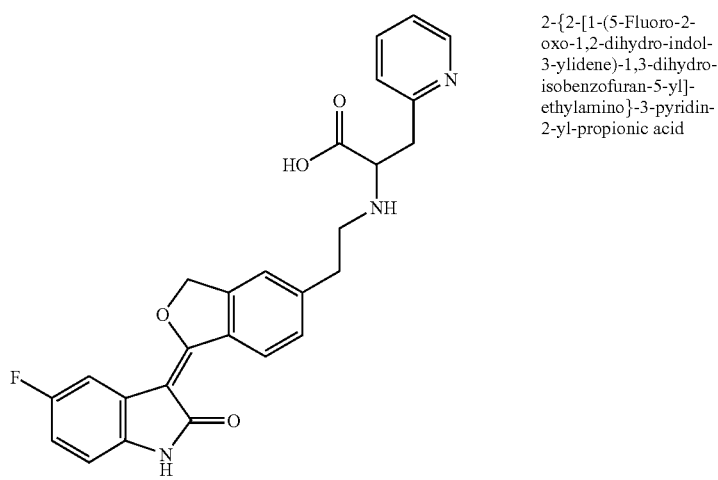 | 2-{2-[1-(5-Fluoro-2-oxo-1,2-dihydro-indol-3-ylidene)-1,3-dihydro-isobenzofuran-5-yl]-ethylamino}-3-pyridin-2-yl-propionic acid | 459.475 | 8 |
| 398 | 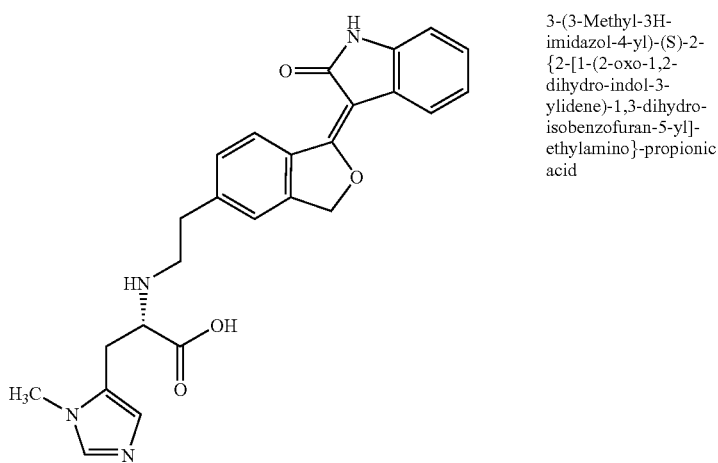 | 3-(3-Methyl-3H-imidazol-4-yl)-(S)-2-{2-[1-(2-oxo-1,2-dihydro-indol-3-ylidene)-1,3-dihydro-isobenzofuran-5-yl]-ethylamino}-propionic acid | 444.489 | 8 |

TABLE 8-continued
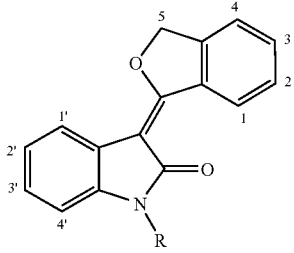
| 399 | 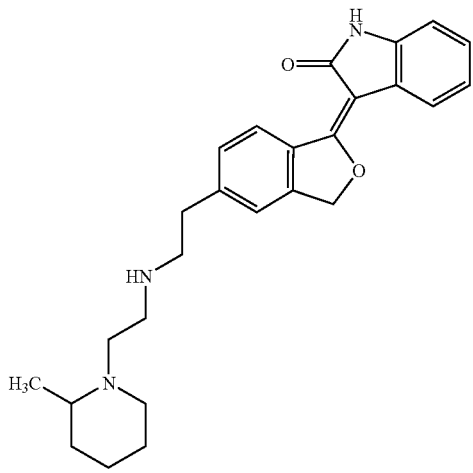 [SMILES: CC1CCCCN1CCNCCc1ccc2c(c1)CO/C2=C1/C(=O)Nc2ccccc21] | 3-(5-{2-[2-(2-Methyl-piperidin-1-yl)-ethylamino]-ethyl}-3H-isobenzofuran-1-ylidene)-1,3-dihydro-indol-2-one | 417.55 | 8 |
| 400 | 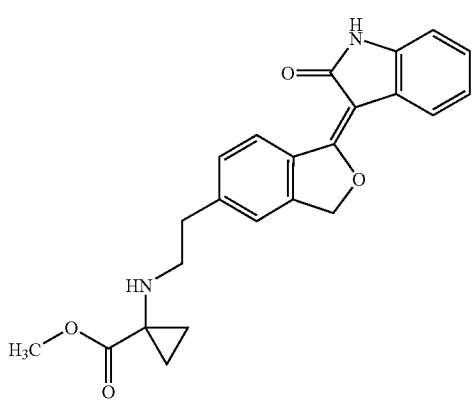 [SMILES: COC(=O)C1(NCCc2ccc3c(c2)CO/C3=C2/C(=O)Nc3ccccc32)CC1] | 1-{2-[1-(2-Oxo-1,2-dihydro-indol-3-ylidene)-1,3-dihydro-isobenzofuran-5-yl]-ethylamino}-cyclopropanecarboxylic acid methyl ester | 390.437 | 8 |
| 401 | 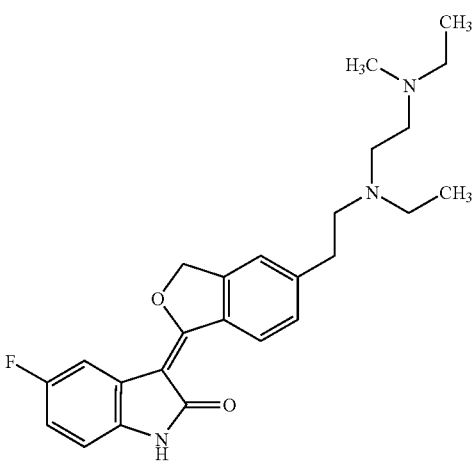 [SMILES: CCN(C)CCN(CC)CCc1ccc2c(c1)CO/C2=C1/C(=O)Nc2ccc(F)cc21] | 3-[5-(2-{Ethyl-[2-(ethyl-methyl-amino)-ethyl]-amino}-ethyl)-3H-isobenzofuran-1-ylidene]-5-fluoro-1,3-dihydro-indol-2-one | 423.529 | 8 |

TABLE 8-continued
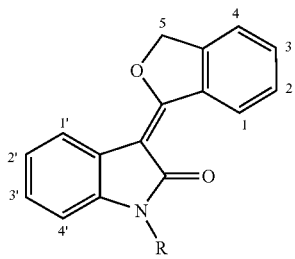
| 402 | 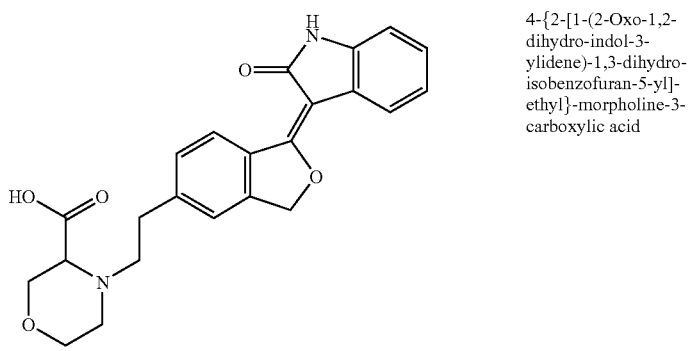 | 4-{2-[1-(2-Oxo-1,2-dihydro-indol-3-ylidene)-1,3-dihydro-isobenzofuran-5-yl]-ethyl}-morpholine-3-carboxylic acid | 406.436 | 8 |
| --- | --- | --- | --- | --- |
| 403 | 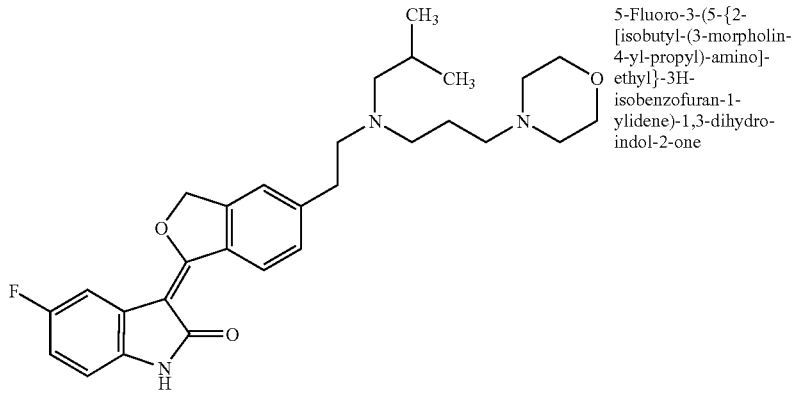 | 5-Fluoro-3-(5-{2-[isobutyl-(3-morpholin-4-yl-propyl)-amino]-ethyl}-3H-isobenzofuran-1-ylidene)-1,3-dihydro-indol-2-one | 493.619 | 8 |
| 404 | 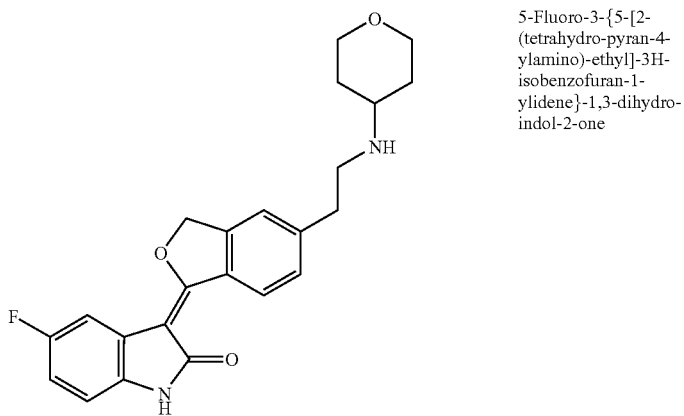 | 5-Fluoro-3-{5-[2-(tetrahydro-pyran-4-ylamino)-ethyl]-3H-isobenzofuran-1-ylidene}-1,3-dihydro-indol-2-one | 394.444 | 8 |

TABLE 8-continued
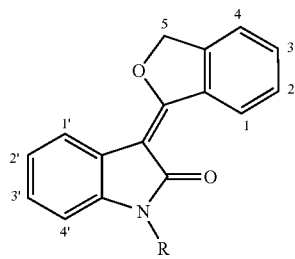
| | | | | |
|---|---|---|---|---|
| 405 | 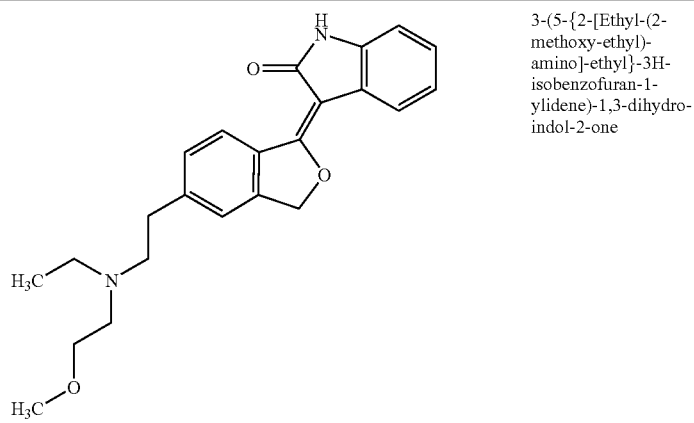 | 3-(5-{2-[Ethyl-(2-methoxy-ethyl)-amino]-ethyl}-3H-isobenzofuran-1-ylidene)-1,3-dihydro-indol-2-one | 378.469 | 8 |
| 406 | 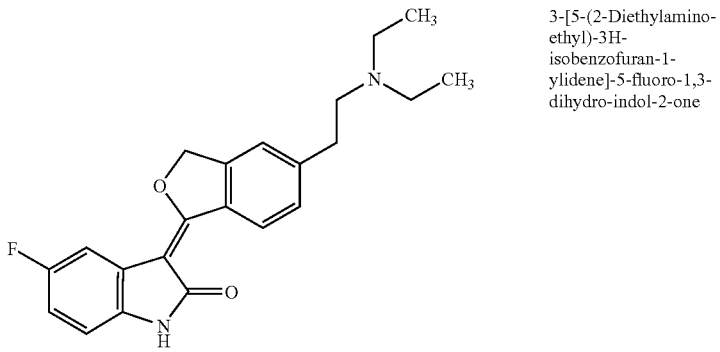 | 3-[5-(2-Diethylamino-ethyl)-3H-isobenzofuran-1-ylidene]-5-fluoro-1,3-dihydro-indol-2-one | 366.434 | 8 |
| 407 | 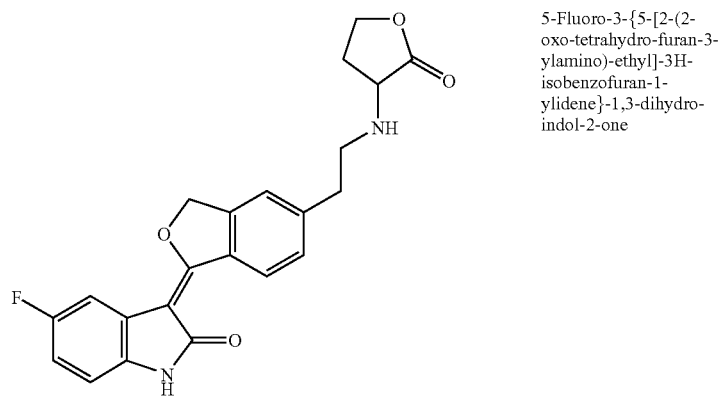 | 5-Fluoro-3-{5-[2-(2-oxo-tetrahydro-furan-3-ylamino)-ethyl]-3H-isobenzofuran-1-ylidene}-1,3-dihydro-indol-2-one | 394.4 | 8 |

TABLE 8-continued

| | | | | |
|---|---|---|---|---|
| 408 | | 3-(5-{2-[(1,1-Dioxo-tetrahydro-1lambda*6*-thiophen-3-yl)-methyl-amino]-ethyl}-3H-isobenzofuran-1-ylidene)-5-fluoro-1,3-dihydro-indol-2-one | 442.509 | 8 |
| 409 | | 1-{2-[1-(5-Fluoro-2-oxo-1,2-dihydro-indol-3-ylidene)-1,3-dihydro-isobenzofuran-5-yl]-ethylamino}-cyclopropanecarboxylic acid methyl | 408.427 | 8 |
| 410 | | 3-[5-(2-{Ethyl-[2-(ethyl-methyl-amino)-ethyl]-amino}-ethyl)-3H-isobenzofuran-1-ylidene]-1,3-dihydro-indol-2-one | 405.539 | 8 |

TABLE 8-continued

| No. | Structure | Name | MW | Ref |
|---|---|---|---|---|
| 411 | 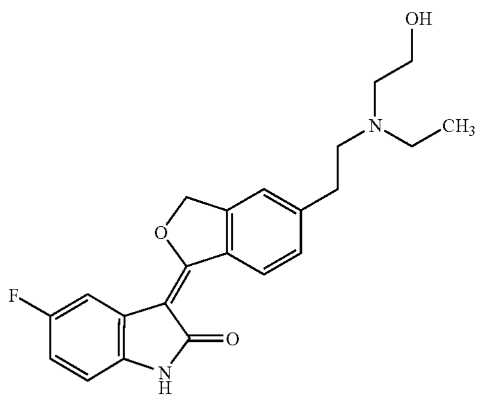 [SMILES: CCN(CCO)CCc1ccc2c(c1)CO/C2=C1/C(=O)Nc2ccc(F)cc21] | 3-(5-{2-[Ethyl-(2-hydroxy-ethyl)-amino]-ethyl}-3H-isobenzofuran-1-ylidene)-5-fluoro-1,3-dihydro-indol-2-one | 382.433 | 8 |
| 412 | 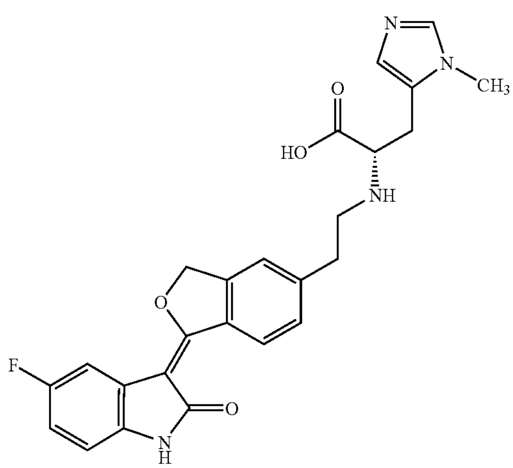 [SMILES: Cn1cncc1C[C@H](NCCc1ccc2c(c1)CO/C2=C1/C(=O)Nc2ccc(F)cc21)C(=O)O] | (S)-2-{2-[1-(5-Fluoro-2-oxo-1,2-dihydro-indol-3-ylidene)-1,3-dihydro-isobenzofuran-5-yl]-ethylamino}-3-(3-methyl-3H-imidazol-4-yl)-propionic acid | 462.479 | 8 |
| 413 | 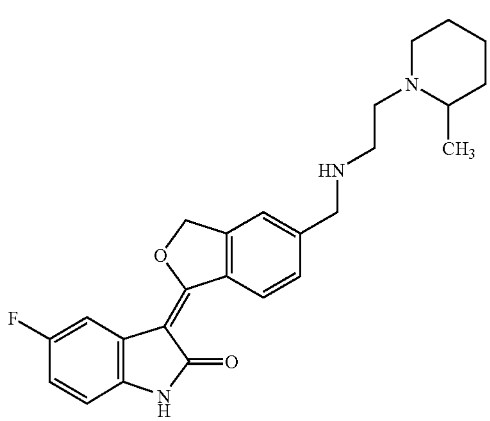 [SMILES: CC1CCCCN1CCNCc1ccc2c(c1)CO/C2=C1/C(=O)Nc2ccc(F)cc21] | 5-Fluoro-3-(5-{[2-(2-methyl-piperidin-1-yl)-ethylamino]-methyl}-3H-isobenzofuran-1-ylidene)-1,3-dihydro-indol-2-one | 421.513 | 8 |

TABLE 8-continued
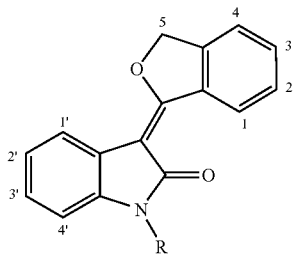
| | | | | |
|---|---|---|---|---|
| 414 | 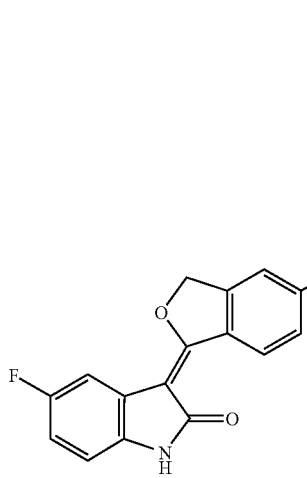 | 5-Fluoro-3-(5-{2-[2-(2-methyl-piperidin-1-yl)-ethylamino]-ethyl}-3H-isobenzofuran-1-ylidene)-1,3-dihydro-indol-2-one | 435.54 | 8 |
| 415 | 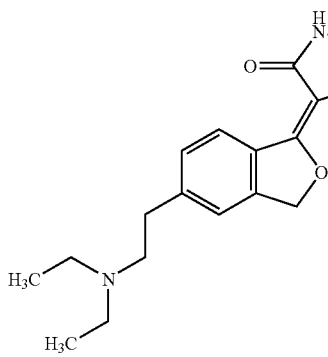 | 3-[5-(2-Diethylamino-ethyl)-3H-isobenzofuran-1-ylidene]-1,3-dihydro-indol-2-one | 348.444 | 8 |
| 416 | 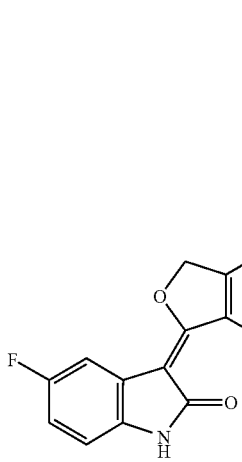 | 5-Fluoro-3-(5-{2-[4-(2-methoxy-ethyl)-piperazin-1-yl]-ethyl}-3H-isobenzofuran-1-ylidene)-1,3-dihydro-indol-2-one | 437.512 | 8 |

TABLE 8-continued
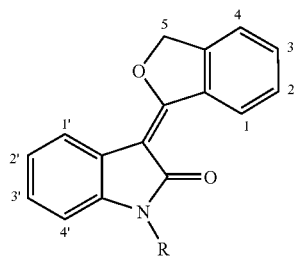
| | | | | | |
|---|---|---|---|---|---|
| 417 | 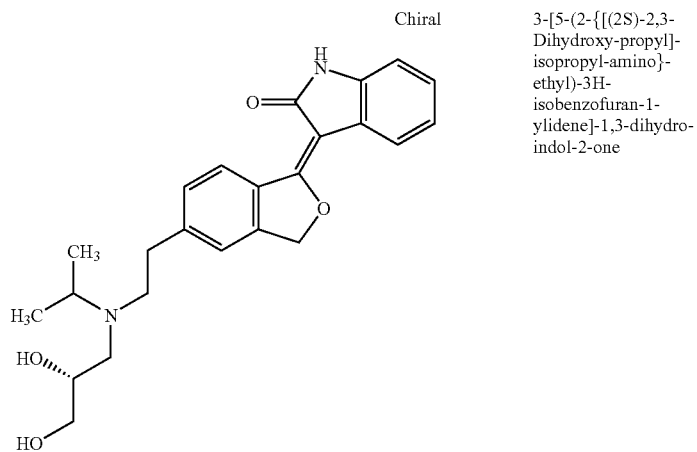 | Chiral | 3-[5-(2-{[(2S)-2,3-Dihydroxy-propyl]-isopropyl-amino}-ethyl)-3H-isobenzofuran-1-ylidene]-1,3-dihydro-indol-2-one | 408.495 | 8 |
| 418 | 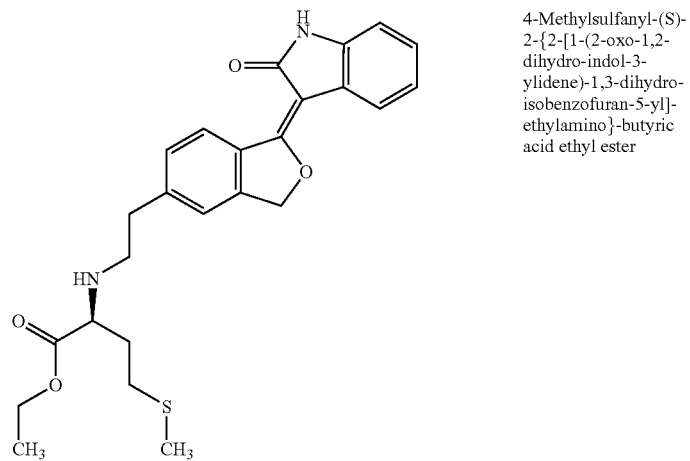 | | 4-Methylsulfanyl-(S)-2-{2-[1-(2-oxo-1,2-dihydro-indol-3-ylidene)-1,3-dihydro-isobenzofuran-5-yl]-ethylamino}-butyric acid ethyl ester | 452.572 | 8 |

TABLE 8-continued
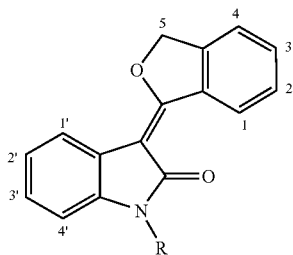
| | | | |
|---|---|---|---|
| 419 | 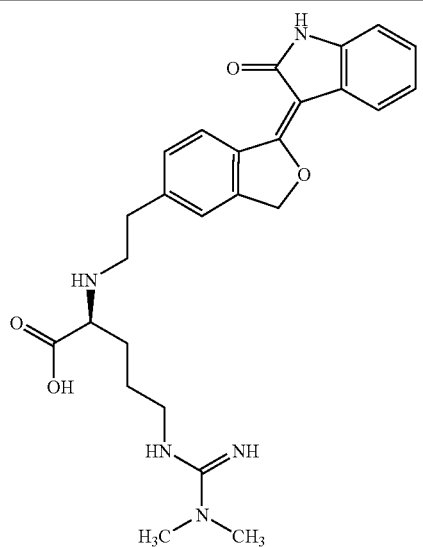 | 5-(N',N'-Dimethyl-guanidino)-(S)-2-{2-[1-(2-oxo-1,2-dihydro-indol-3-ylidene)-1,3-dihydro-isobenzofuran-5-yl]-ethylamino}-pentanoic acid | 477.562 | 8 |
| 420 | 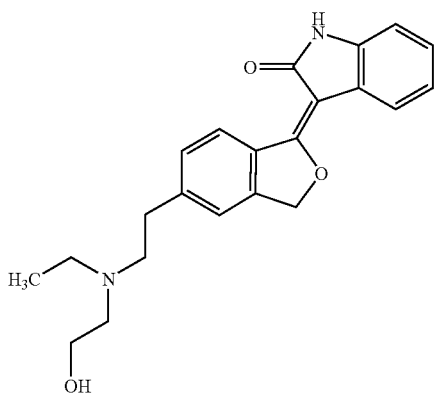 [SMILES: CCN(CCO)CCc1ccc2c(c1)CO/C2=C1/C(=O)Nc2ccccc21] | 3-(5-{2-[Ethyl-(2-hydroxy-ethyl)-amino]-ethyl}-3H-isobenzofuran-1-ylidene)-1,3-dihydro-indol-2-one | 364.443 | 8 |
| 421 | 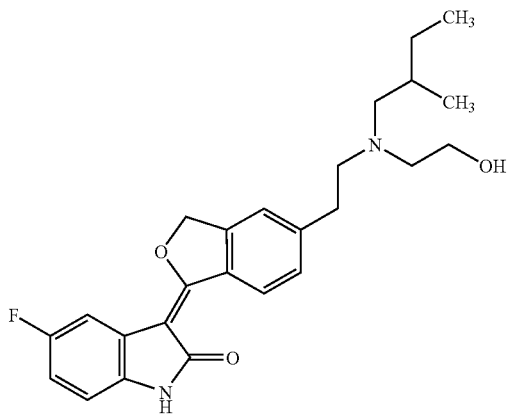 [SMILES: CCC(C)CN(CCO)CCc1ccc2c(c1)CO/C2=C1/C(=O)Nc2ccc(F)cc21] | 5-Fluoro-3-(5-{2-[(2-hydroxy-ethyl)-(2-methyl-butyl)-amino]-ethyl}-3H-isobenzofuran-1-ylidene)-1,3-dihydro-indol-2-one | 424.513 | 8 |

TABLE 8-continued

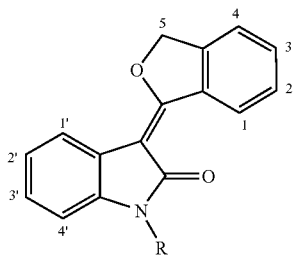

| 422 | 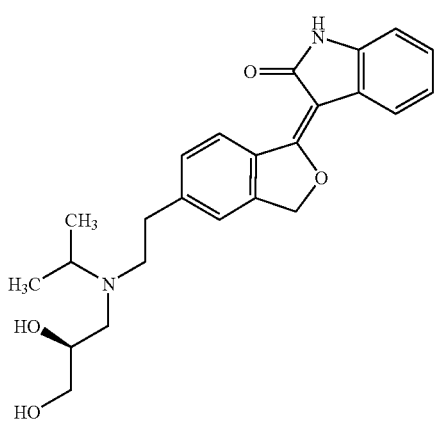 | Chiral | 3-[5-(2-{[(2R)-2,3-Dihydroxy-propyl]-isopropyl-amino}-ethyl)-3H-isobenzofuran-1-ylidene]-1,3-dihydro-indol-2-one | 408.495 | 8 |

Tables 9 through 11, which include Examples 423 through 539, are found in U.S. patent application Ser. No. 11/180,496, which is hereby incorporated by reference.

The following Examples describe the synthesis of the most preferred TKI compounds utilized in the ocular implants of this invention.

EXAMPLE 426

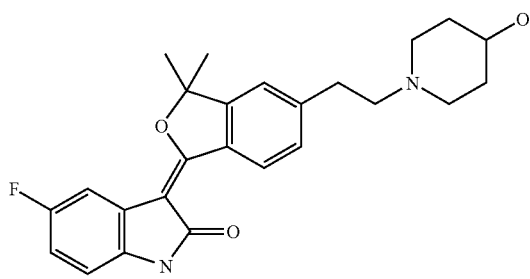 [SMILES: CC1(C)O/C(=C2/C(=O)Nc3ccc(F)cc32)c2ccc(CCN3CCC(O)CC3)cc21]

5-Fluoro-3-{5-[2-(4-hydroxy-piperidin-1-yl)-ethyl]-3,3-dimethyl-3H-isobenzofuran-1-ylidene}-1,3-dihydro-indol-2-one To a stirred solution of 5-fluorooxindole (7.86 g, 52 mmol) in anhydrous THF (60 ml) under nitrogen was added 1.0M LiHMDS/THF solution (104 ml, 104 mmol). The mixture was stirred at room temperature for 15 minutes, and then 5-[2-(4-hydroxy-piperidin-1-yl)-ethyl]-3,3-dimethyl-3H-isobenzofuran-1-one (5.0 g, 17.3 mmol) was added. After stirring at room temperature for 2 hours, the mixture was quenched with 50 ml of 2.5M $H_2SO_4$, heated at 65° C. for 30 minutes and poured into 500 ml of water. The mixture was basified with 5M NaOH to about pH=9 and continuously stirred at room temperature for 16 hours. The resulting solids were filtered, rinsed with water, dried under vacuum to give the title compound as a yellow solid (4.74 g, 65%).

$^1$H NMR (500 MHz, DMSO-$d_6$) δ ppm 1.34-1.43 (m, 2 H) 1.69-1.76 (m, 8 H) 2.10 (br. s., 2 H) 2.57 (t, J=7.32 Hz, 2 H) 2.76-2.83 (m, 2 H) 2.87 (t, J=7.32 Hz, 2 H) 3.40-3.49 (m, 1 H) 4.55 (d, J=4.39 Hz, 1 H) 6.79 (dd, J=8.30, 4.39 Hz, 1 H) 6.93 (td, J=9.03, 2.93 Hz, 1 H) 7.43 (d, J=8.30 Hz, 1 H) 7.53 (s, 1 H) 7.59 (dd, J=9.28, 2.44 Hz, 1 H) 9.47 (d, J=8.30 Hz, 1 H) 10.40 (s, 1 H)

EXAMPLE 474

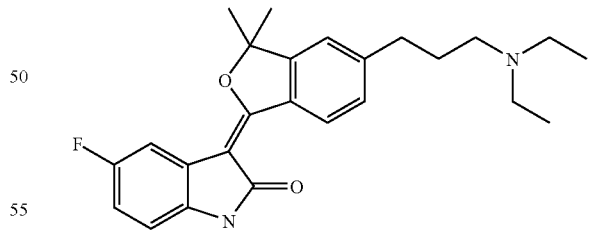

3-[5-(3-Diethylamino-propyl)-3,3-dimethyl-3H-isobenzofuran-1-ylidene]-5-fluoro-1,3-dihydro-indol-2-one A solution of methanesulfonic acid 3-[1-(5-fluoro-2-oxo-1,2-dihydro-indol-3-ylidene)-3,3-dimethyl-1,3-dihydro-isobenzofuran-5-yl]-propyl ester (170 mg, 0.39 mmol) and diethylamine (0.30 ml, 2.92 mmol) in dioxane (1.6 ml) was heated at 75° C. in a pressure tube for 36 hours. The mixture was evaporated, dissolved in EtOAc, and the EtOAc washed with H₂O and brine. The aqueous layer was also extracted with CHCl₃. The organic layers were combined, dried over anhydrous Na₂SO₄, and then evaporated to a yellow film. The sample was passed through a plug of silica gel eluting with 10% methanol in CHCl₃ to give a yellow-orange solid. The solid was dissolved in EtOAc, washed with saturated aqueous NaHCO₃, brine, dried over anhydrous Na₂SO₄, and evaporated to a yellow solid. The solid was chromatographed eluting with CHCl₃/MeOH to give the title compound as a yellow solid (88 mg, 54%).

¹H NMR (500 MHz, DMSO-d₆) δ ppm 0.93 (t, J=7.08 Hz, 6 H) 1.72 (s, 6 H) 1.77 (dt, J=14.77, 7.51 Hz, 2 H) 2.41 (t, J=6.83 Hz, 2 H) 2.47 (q, J=6.83 Hz, 4H) 2.71-2.76 (m, 2 H) 6.79 (dd, J=8.30, 4.88 Hz, 1 H) 6.92 (ddd, J=9.64, 8.42, 2.93 Hz, 1 H) 7.42 (dd, J=8.30, 1.46 Hz, 1 H) 7.53 (d, J=0.98 Hz, 1 H) 7.59 (dd, J=9.52, 2.68 Hz, 1 H) 9.48 (d, J=8.30 Hz, 1 H) 10.40 (s, 1 H).

EXAMPLE 481

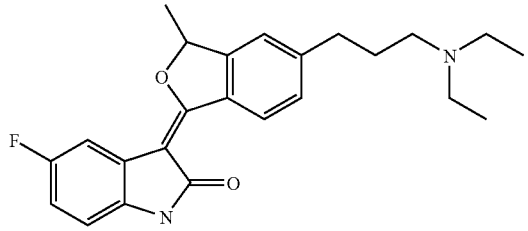

3-[5-(3-Diethylamino-propyl)-3-methyl-3H-isobenzofuran-1-ylidene]-5-fluoro-1,3-dihydro-indol-2-one Experimental procedure similar to Example 474.

¹H NMR (500 MHz, CDCl₃) δ ppm 1.04 (t, J=7.08 Hz, 6 H) 1.73 (d, J=6.83 Hz, 3 H) 1.87 (dt, J=14.16, 7.08 Hz, 2 H) 2.51 (t, J=7.32 Hz, 2 H) 2.54-2.61 (m, 4H) 2.77 (t, J=7.81 Hz, 2 H) 5.88 (q, J=6.83 Hz, 1 H) 6.76 (dd, J=8.79, 4.39 Hz, 1 H) 6.84 (td, J=8.91, 2.69 Hz, 1 H) 7.22 (s, 1 H) 7.38 (d, J=8.30 Hz, 1 H) 7.70 (dd, J=9.52, 2.68 Hz, 1H) 7.73 (s, 1 H) 9.58 (d, J=8.30 Hz, 1 H).

EXAMPLE 508

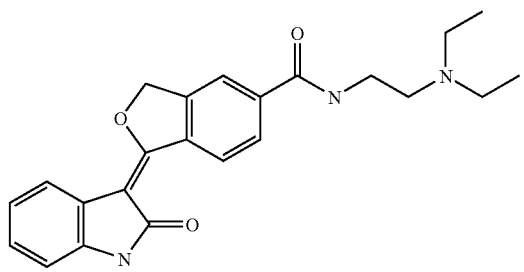 [SMILES: CCN(CC)CCNC(=O)c1ccc2c(c1)CO/C2=C1/C(=O)Nc2ccccc21]

1-(2-Oxo-1,2-dihydro-indol-3-ylidene)-1,3-dihydro-iso benzofuran-5-carboxylic acid (2-diethylamino-ethyl)-amide A mixture of 1-(2-oxo-1,2-dihydro-indol-3-ylidene)-1,3-dihydro-isobenzofuran-5-carboxylic acid (100 mg, 0.34 mmol) and 1,1'-carbonyldiimidazole (100 mg, 0.62 mmol) in THF (10 ml) was stirred at room temperature for 16 hours. N,N-diethylethylenediamine (0.25 ml, 1.76 mmol) was added. The mixture was stirred for 15 minutes and poured into water (100 ml). The precipitates were filtered, washed with water and dried under vacuum to give the title compound as a yellow powder (99 mg, 74%).

¹H NMR (500 MHz, DMSO-d₆) δ ppm 0.98 (t, J=7.08 Hz, 6 H) 2.53 (t, J=7.08 Hz, 4 H) 2.58 (t, J=7.32 Hz, 2 H) 3.36 (t, J=7.32 Hz, 2 H) 5.86 (s, 2 H) 6.84 (d, J=7.32 Hz, 1 H) 6.98 (td, J=7.69, 1.22 Hz, 1 H) 7.14 (td, J=7.57, 1.46 Hz, 1 H) 7.85 (d, J=7.32 Hz, 1 H) 7.98 (d, J=8.79 Hz, 1H) 8.05 (s, 1 H) 8.62 (t, J=5.86 Hz, 1 H) 9.68 (d, J=8.30 Hz, 1 H) 10.49 (s, 1 H)

EXAMPLE 521

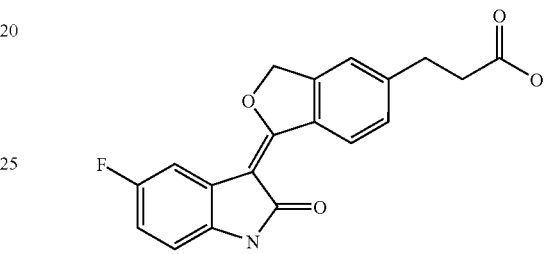

3-[1-(5-Fluoro-2-oxo-1,2-dihydro-indol-3-ylidene)-1,3-dihydro-isobenzofuran-5-yl]-propionic acid To a stirred solution of 5-fluorooxindole (218 mg, 1.44 mmol) in anhydrous THF (10 ml) under nitrogen was added 1.0M LiHMDS/THF solution (2.9 ml, 2.9 mmol). After the mixture was stirred at room temperature for 10 minutes, 3-(1-Oxo-1,3-dihydro-isobenzofuran-5-yl)-propionic acid (100 mg, 0.48 mmol) was added. After the mixture was stirred at room temperature for 2 hours, 1 M sulfuric acid solution (10 ml) was added. The mixture was heated at 60° C. for 2 hours, and then poured into 150 ml of water. The resulting solid was filtered, rinsed with water, dried in vacuo to give the title compound as a yellow solid (96 mg, 59%).

¹H NMR (500 MHz, DMSO-d₆) δ ppm 2.63 (t, J=7.57 Hz, 2 H) 2.98 (t, J=7.57 Hz, 2 H) 5.80 (s, 2 H) 6.79 (dd, J=8.54, 4.64 Hz, 1 H) 6.90-6.96 (m, 1H) 7.47 (d, J=8.30 Hz, 1H) 7.54 (s, 1 H) 7.57 (dd, J=9.76, 2.44 Hz, 1 H) 9.54 (d, J=8.30 Hz, 1 H) 10.42 (s, 1 H) 12.21 (s, 1 H)

The compounds of formula II, below, may also be utilized in preparing the ocular implants described herein.

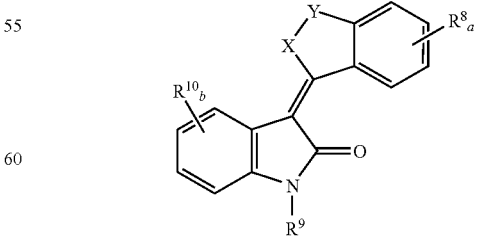

wherein X is O; Y is [C(R⁹)₂]c; R¹⁰ is selected from the group consisting of halogen, nitro, hydroxy, hydrocarbyl, substituted hydrocarbyl, amide, thioamide, amine, thioether and sulfonyl; $R^8$ is selected from the group consisting of halogen, nitro, hydroxy, hydrocarbyl, substituted hydrocarbyl, amide, thioamide, amine, thioether and sulfonyl and phosphonic acid; $R^9$ is selected from the group consisting of hydrogen, hydrocarbyl and substituted hydrocarbyl; c is an integer of from 1 to 2; b is 0 or an integer from 1 to 3; a is 0 or an integer of from 1 to 3 and pharmaceutically acceptable salts thereof. Said hydrocarbyl and/or substituted hydrocarbyl may be alkyl, alkenyl, alkynyl, aryl (including carbocyclic aryl and heterocyclic aryl) and alkaryl.

Procedures for the Preparation of TKI Ocular Implants

Powder Blending

The drug, TKI, was stored at room temperature with minimal light exposure, and polymers, utilized for the matrix, were stored at 5° C. and allowed to equilibrate to room temperature prior to use. Both the TKI and the polymer were used as received. Formulations, listed in Table 1, were blended in a stainless steel mixing capsule with two stainless steel balls and placed in a Retsch mill at 30 cps or Turbula blender at 96 rpm for 5 to 15 minutes. Depending on the starting materials, formulations underwent four to six blending cycles at five to fifteen minutes each. Between blending cycles, a stainless steel spatula was used to dislodge material from the inside surfaces of the mixing vessel.

Powder Compaction

A die with a 720 μm opening was attached to a stainless steel extrusion barrel, and the barrel was inserted into the powder compactor assembly. The powder compactor is set to 50 psi, and the powder is added to the barrel in small increments using a stainless steel powder funnel. After the addition of each increment, the pneumatic compactor was actuated to compress the added powder. This process was repeated until the extrusion barrel was full.

Extrusion

A piston extruder was set to temperature and allowed to equilibrate. The extrusion temperature was chosen based on drug-load and polymer. The extrusion temperature was adjusted for each formulation to produce smooth, uniform-looking filaments. After the extruder temperature equilibrated, the piston extrusion barrel was inserted into the extruder, and a thermocouple was inserted to measure the temperature at the surface of the barrel. After the barrel temperature equilibrated, the piston was inserted into the barrel and the piston speed was set at 0.0025 in/min. The first 2-4 inches of extrudate was discarded. Afterwards, 3-5-inch pieces were cut directly into a centrifuge tube. Samples were labeled and stored in a sealed foil pouch containing desiccant. Formulations with higher drug load required higher extrusion temperatures. Polymers with higher intrinsic viscosities required higher extrusion temperatures than polymers with lower intrinsic viscosities. Lactide-glycolide co-polymers with a higher lactide percentage (75:25) required a lower processing temperature than polymers with a lower lactide percentage (50:50). Formulation information and extrusion temperatures are listed in Table A.

TABLE A

Formulation and Extrusion Temperature for TKI Example 426, Example 474, Example 508, Example 521, and Example 481

| API | Formulation # | API Loading (%) | Polymer (s) | Extrusion Temp (Deg. C.) |
|---|---|---|---|---|
| Example 426 | 7409-007 | 50 | Purac PDL* | 80 |
|  | 7409-023 | 60 | Purac PDL | 75 |
|  | 7409-024 | 50 | Resomer RG752± | 81 |
|  | 7409-025 | 50 | Resomer RG755† | 92 |
|  | 7409-026 | 60 | Resomer RG755 | 94 |
|  | 7409-040 | 40 | Resomer RG755 | 94 |
|  | 7409-041 | 30 | Resomer RG755 | 94 |
|  | 7409-042 | 40 | Resomer RG752 | 84 |
|  | 7409-045 | 40 | Resomer RG502** | 96 |
|  | 7409-046 | 40 | Resomer RG505•• | 103 |
| Example 474 | 7409-009 | 50 | Resomer RG755 | 96 |
|  | 7409-010 | 60 | Resomer RG755 | 98 |
|  | 7409-012 | 50 | Resomer R104†† | 67 |
| Example 508 | 7409-014 | 50 | Resomer RG755 | 110 |
|  | 7409-015 | 60 | Resomer RG755 | 115 |
|  | 7409-017 | 50 | Res. RG755, Res. R104, 3:2 | 94 |
|  | 7409-021 | 50 | Resomer RG506o | 117 |
|  | 7409-022 | 50 | Resomer R104 | 71 |
|  | 7409-035 | 50 | Resomer R207‡ | 139 |
|  | 7409-043 | 40 | Resomer RG752 | 83 |
|  | 7409-044 | 40 | Resomer RG502 | 94 |
| Example 521 | 7409-027 | 50 | Resomer RG755 | 107 |
|  | 7409-028 | 60 | Resomer RG755 | 118 |
|  | 7409-029 | 50 | Purac PDL | 109 |
|  | 7409-030 | 50 | Resomer R104 | 80 |
|  | 7409-031 | 50 | Resomer RG506 | 129 |
|  | 7409-032 | 60 | Res. RG755, Res. R104, 1:1 | 100 |
|  | 7409-033 | 50 | Resomer R207‡ | 139 |
|  | 7409-034 | 60 | RG502S | 96 |
| Example 481 | 7409-070 | 60 | Resomer RG755 | 114 |
|  | 7409-071 | 40 | Resomer RG755 | 95 |
|  | 7409-072 | 60 | Resomer RG752 | 91 |
|  | 7409-073 | 40 | Resomer RG752 | 91 |
|  | 7409-074 | 60 | Resomer RG502 | 102 |

TABLE A-continued

Formulation and Extrusion Temperature for TKI Example 426, Example 474, Example 508, Example 521, and Example 481

| API | Formulation # | API Loading (%) | Polymer (s) | Extrusion Temp (Deg. C.) |
|---|---|---|---|---|
| | 7409-075 | 40 | Resomer RG502 | 93 |
| | 7409-076 | 60 | Resomer RG504• | 121 |

*Purac PDL = Purac 50:50 Poly(D,L-lactide-co-glycolide)
**Resomer RG502, RG502S = Boehringer Ingelheim 50:50 Poly(D,L-lactide-co-glycolide), IV = 0.16-0.24(dl/g)
•Resomer RG504 = Boehringer Ingelheim 50:50 Poly(D,L-lactide-co-glycolide), IV = 0.45-0.60(dl/g)
••Resomer RG505 = Boehringer Ingelheim 50:50 Poly(D,L-lactide-co-glycolide), IV = 0.7(dl/g)
∘Resomer RG506 = Boehringer Ingelheim 50:50 Poly(D,L-lactide-co-glycolide), IV = 0.8(dl/g)
±Resomer RG752 = Boehringer Ingelheim 75:25 Poly(D,L-lactide-co-glycolide), IV = 0.2(dl/g)
†Resomer RG755 = Boehringer Ingelheim 50:50 Poly(D,L-lactide-co-glycolide), IV = 0.6(dl/g)
††Resomer R104 = Poly(L-lactide), MW = 2000
‡Resomer R207 = Poly(L-lactide), IV = 1.6

In Table A, Example Number refers to the TKI prepared in the above-numbered example and utilized as the API (active pharmaceutical ingredient) in the ocular implant tested.

The polymers utilized in such ocular implants are as follows:

| Resomer | Monomer ratio | i.v. dL/g(MW) |
|---|---|---|
| RG502 | 50:50 poly (D,L-lactide-co-glycolide) | 0.2 |
| RG502H | 50:50 poly (D,L-lactide-co-glycolide) | 0.2 |
| RG504 | 50:50 poly (D,L-lactide-co-glycolide) | 0.5 |
| RG505 | 50:50 poly (D,L-lactide-co-glycolide) | 0.7 |
| RG509 | 50:50 poly (D,L-lactide-co-glycolide) | 1.6 |
| RG752 | 75:25 poly (D,L lactide-co-glycolide) | 0.2 |
| RG752S | 50:50 poly (D,L-lactide-co-glycolide) | 0.2 |
| RG755 | 50:50 poly (D,L-lactide-co-glycolide) | 0.6(40000) |
| R104 | poly (D,L-lactide) | (3500) |

The release rate was determined by the below procedure and certain of the release studies were reported in FIGS. 1 through 6.

The in vitro release study was carried out in an incubator at 37° C. shaking at 120 rpm.

The release medium was 0.02% Polysorbate 80 containing 10 mM phosphate buffered saline, pH 7.4. The medium and implants were placed in 20 mL scintillation vials. At given time points, the medium containing released drug was collected and replaced with fresh medium. The concentration of the compound in the release medium was analyzed using HPLC.

The results are reported in FIGS. 1 through 6.

All references cited herein are hereby incorporated by reference in their entirety.

The foregoing description details specific methods and compositions that can be employed to practice the present invention, and represents the best mode contemplated. However, it is apparent for one of ordinary skill in the art that further compositions with the desired pharmacological properties can be prepared in an analogous manner. Similarly, different pharmaceutical compositions may be prepared and used with substantially the same result. Thus, however detailed the foregoing may appear in text, it should not be construed as limiting the overall scope hereof.

The invention claimed is:

1. An ocular implant comprising
a tyrosine kinase inhibitor and a biodegradable polymer matrix that releases drug at a rate effective to sustain release of an amount of the tyrosine kinase inhibitor from the implant for at least about one week after the implant is placed in an eye, wherein the tyrosine kinase inhibitor is provided in an amount from about 40% by weight to about 70% by weight of the implant, and the biodegradable polymer matrix comprises a poly(lactide-co-glycolide) in an amount from about 30% by weight to about 60% by weight of the implant, wherein the implant is formed by an extrusion process, and wherein said tyrosine kinase inhibitor is a compound having the formula:

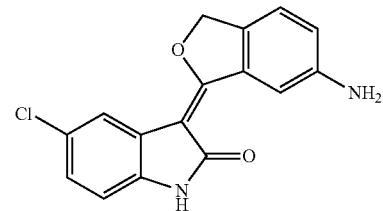 [SMILES: Nc1ccc2c(c1)/C(=C1\C(=O)Nc3ccc(Cl)cc31)OC2]

or a pharmaceutically acceptable salt thereof.

2. The implant of claim 1, wherein the implant is a biodegradable intravitreal implant.

* * * * *